(12) United States Patent
Ahrens et al.

(10) Patent No.: US 7,998,704 B2
(45) Date of Patent: Aug. 16, 2011

(54) METHODS FOR MAGNETIC RESONANCE IMAGING

(75) Inventors: Eric T. Ahrens, Pittsburgh, PA (US);
Clinton S. Robison, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 11/080,732

(22) Filed: Mar. 14, 2005

(65) Prior Publication Data

US 2006/0024662 A1 Feb. 2, 2006

Related U.S. Application Data

(63) Continuation-in-part of application No. 10/384,496, filed on Mar. 7, 2003.

(60) Provisional application No. 60/363,163, filed on Mar. 7, 2002.

(51) Int. Cl.
*C12P 21/04* (2006.01)
*C12P 21/06* (2006.01)
*C12N 15/00* (2006.01)
*C07H 21/04* (2006.01)

(52) U.S. Cl. .......... 435/69.7; 435/320.1; 435/69.6; 435/69.1; 435/4; 536/23.4

(58) Field of Classification Search .......... None
See application file for complete search history.

(56) References Cited

U.S. PATENT DOCUMENTS

| | | | |
|---|---|---|---|
| 5,707,605 A | 1/1998 | Meade et al. | |
| 6,232,295 B1 | 5/2001 | Kayyem et al. | |
| 6,315,981 B1 | 11/2001 | Unger | |
| 6,316,692 B1 | 11/2001 | Readhead et al. | |
| 6,495,355 B1 * | 12/2002 | Contag et al. | 435/189 |
| 6,511,967 B1 * | 1/2003 | Weissleder et al. | 514/44 |
| 6,812,339 B1 * | 11/2004 | Venter et al. | 536/24.31 |
| 7,097,841 B2 * | 8/2006 | Carter et al. | 424/192.1 |
| 2002/0025296 A1 | 2/2002 | Kanaus et al. | |
| 2003/0219385 A1 | 11/2003 | Ahrens | |
| 2004/0006001 A1 | 1/2004 | Carter et al. | |

FOREIGN PATENT DOCUMENTS

| | | |
|---|---|---|
| WO | WO98/29535 | 7/1998 |
| WO | WO-98/33809 | 8/1998 |
| WO | WO03075747 A2 | 9/2003 |

OTHER PUBLICATIONS

Cherry et all., 2004, Phys. Med. Biol 49:R13-R48.*
Weissleder etal., 2000, Nature Medicine 6:351-354.*
Fielden et al., 2001, Toxicological sciences 60:6-10.*
Goncalves, Bioessays, 2005, 27: 506-517.*
Lee et al., 2002, Biochem. Biophys. Res. Comm. 298: 225-229.*
Makrides., 1999, protein expression and purification 17:183-202.*
Stic Sequence search on Seq ID No. 2 (pp. 1-3).*
Vyzamal et al 2000; Cellular and Molecular Biology 46:835-842.*

(Continued)

*Primary Examiner* — Robert M Kelly
*Assistant Examiner* — Kelaginamane Hiriyanna
(74) *Attorney, Agent, or Firm* — Ropes & Gray LLP

(57) ABSTRACT

In certain aspects the present invention provides methods and compositions related to contrast agents for magnetic resonance imaging. In certain variations, contrast agents provided herein are generated in situ via genetic instructions and become potent upon sequestering available metal atoms. Exemplary contrast agents include metal-binding proteins.

6 Claims, 42 Drawing Sheets

OTHER PUBLICATIONS

Pereira et al., 1977. Biochemistry.36:7917-7927.*
Stic Sequence search on Seq ID No. 2 Feb. 3, 2011 (pp. 1-3).*
Bartzokis, G. and Tishier, T.A., "MRI Evaluation of Basal Ganglia Ferritin Iron and Neurotoxicity in Alzheimer's and Huntington's Disease," 2000 CMB 46:821.
Vymazal, 2000, Differentiation between hemosiderin- and ferritin-bound brain iron using nuclear magnetic resonance and magnetic resonance imaging, Cell Mol Biol 46:835-842.
Ponka et al., "Function and Regulation of Transferrin and Ferritin," Semin Hematol., 35:1 35-54 (1998), Abstract.
Rucker et al., "Recombinant Ferritin: Modulation of Subunit Stiochiomerty in Bacterial Expression Systems," Protein Engineering, 10:8 967-973 (1997).
Santambrogio et al., "Production and Characterization of Recombinant Heteropolymers of Human Ferritin H and L Chains," J Biol Chem. 268:17 12744-12748 (1993).
Koretsky, Nuclear Magnetic Resonance Detection of the Consequences of Transgene Expression, News Physiol. Sci. 9:197-202 (1994).
Koretsky et al, Genetic Control of MRI Contrast by Expression of the Transferrin Receptor, Int. Soc. Magn. Res. Med., New York, p. 5471 (1996).
Boyd et al., "Structural and functional relationships of human ferritin H and L chains deduced from cDNA clones," J. Biol. Chem. 260(21):11755-11761 (1985).
Dhar et al., "Sequence of a cDNA encoding the ferritin H-chain from an 11-week-old human fetal brain," Gene 126(2):275-278 (1993).
Dorner et al., "Structure of human ferritin light subunit messenger RNA: comparison with heavy subunit message and functional implications," Proc. Natl. Acad. Sci. USA 82:3139-3143 (1985).
Vymazal et al., "Magnetic resonance imaging of brain iron in health and disease," J. Neurol. Sci. 134(Suppl.):19-26 (1995).
Gottesfeld et al., "Ferritin Effect on the Transverse Relaxation of Water: NMR Microscopy at 9.4 T," MRM, 35:514-520(1996).
"*Homo sapiens* ferritin, light polypeptide, mRNA (cDNA clone MGC:24480 Image:4092360), complete cds." Database EMBL Online! (Nov. 13, 2001).
Ahrens, et al., "A model for MRI contrast enhancement using $T_1$ agents", Proc. Acad. Sci. USA, vol. 95, pp. 8443-8448, Applied Biological Sciences (1998).
Ahrens, et al., "Peripheral somatosensory fMRI in mouse at 11.7 T", NMR in Biomedicine, NMR Biomed. 14:318-324 (2001).
Ahrens, et al., "Receptor-Mediated Endocytosis of Iron-Oxide Particles Provides Efficient Labeling of Dendritic Cells for In Vivo MR Imaging", Magnetic Resonance in Medicine 49:1006-1013 (2003).
Beckmann, et al., "From Anatomy to the Target: Contributions of Magnetic Resonance Imaging to Preclinical Pharmaceutical Research". The Anatomical Record (New Anat.) 265:85-100, (2001).
Cohen, B., et al., "Gerritin as an Endogenous MRI Reporter for Noninvasive Imaging of Gene Expression in C6 Glioma Tumors," Neoplasia, 7(2): 109-117 (2005).
Corsi, et al., "Transient overexpression of human H- and L ferritin chains in COS cells", Biochem. J. (1998) 330, 315-320.
Cozzi, et al., "Overexpression of Wild Type and Mutated Human Ferritin H-chain in HeLa Cells—In Vivo Role of Ferritin Ferroxidase Activity", The Journal of Biological Chemistry, vol. 275, No. 33, pp. 25122-25129, (2000).
Donlin, et al., "Analysis of Iron in Ferritin, the Iron-Storage Protein, A General Chemistry Experiment", Journal of Chemical Education, vol. 75 No. 4, (1998).
Donlin, et al., "Ferritin Molecular-Graphics Tutorial. Iron in Biology: Study of the Iron Content in Ferritin, The Iron-storage Protein", J. Chem. Edu., 75, 437, (1998).
Epsztejn, et al., "H-Ferritin Subunit Overexpression in Erythroid Cells Reduces the Oxidative Stress Response and Induces Multidrug Resistance Properties", Blood, vol. 94, No. 10, (1999):pp. 3593-3603.
Fernandez, et al., "Gene Expression Systems: using nature for the art of expression." San Diego: Academic Press, 1999.
Fleming, et al., "Targeted mutagenesis of the murine transferrin receptor-2 gene produces hemochromatosis", PNAS, vol. 99, No. 16, pp. 10653-10658 (2002).
Fleming, et al., "Transferrin receptor 2: Continued expression in mouse liver in the face of iron overload and in hereditary hemochromatosis", PNAS, vol. 97, No. 5. pp. 2214-2219 (2000).
Genove, G., "A new transgene reporter for in vivo magnetic resonance imaging," Nature Medicine, 11(4):450-454 (2005).
Guo, et al., "Expression and Loading of Recombinant Heavy and Light Chain Homopolymers of Rat Liver Ferritin", Archives of Biochemistry and Biophysics vol. 335, No. 1, pp. 197-204 (1996).
Hamlin, Nadia. "New Use for MRT", The Scientist 14(7):28 (2000).
Harrison, et al. "The ferritins: molecular properties, iron storage function and cellular regulation". Biochimica et Biophysica Acta 1275 (1996) 161-203.
Holbrook, et al. "In Vivo Observation of Cavitation and Embolism Repair Using Magnetic Resonance Imaging1[w]". Plant Physiology, vol. 126, pp. 27-31 (2001).
Ichikawa, T., et al., "MRI of Transgene Expression: Correlation of Therapeutic Gene Expression," Neoplasia, 4(6):523-530 (2002).
Jacobs, et al., "Looking deeper into vertebrate development", trends in Cell Biology 9:73-76 (1999).
Jacobs, et al., "Towards a microMRl atlas of mouse development", Computerized Medical Imaging and Graphics 23 (1999) 15-24.
Lavaute, et al., "Targeted deletion of the gene encoding iron regulatory protein-2 causes misregulation of iron metabolism and neurodegenerative disease in mice", nature genetices, 27:209-214 (2001).
Lois, et al. "Germline Transmission and Tissue-Specific Expression of Transgenes Delivered by Lentiviral Vectors", Science, 295:868-872 (2002).
Lok, Corie., "Medical imaging techniques are being adapted to study gene expression and other cellular activities in living animals. Corie Lok talks to the pioneers who are watching cells at work in the natural habitat". Nature, 412:372-374 (2001).
Louie, et al., "In vivo visualization of gene expression using magnetic resonance imaging", Nature Biotechnology, 18:321-325 (2000).
Mathur-De, et al., "Invited review. Biophysical properties and clinical applications of magnetic resonance imaging contrast agents". The British Journal of Radiology, 1995, vol. 68, No. 807, pp. 225-247.
Miklos, et al., "Integrating molecular medicine with functional proteomics: Realities and expectations", Proteomics 2001, 1, 30-41.
Moats, et al., "A "Smart" Magnetic Resonance Imaging Agent That Reports on Specific Enzymatic Activity", Angew. Chem. Int. Ed. Engl. 1997, 36, No. 7. pp. 726-728.
Moore, A., et al., "Measuring transferrin receptor gene expression by NMR imaging," Biochimica et Biophysica Acta, 1402:239-249 (1998).
Mulvey, et al., "Induction of Ferritin Synthesis in Cells Infected with Mego Virus*", The Journal of Biological Chemistry, vol. 271, 16:9851-9857, (1996).
Narasimhan, et al., "Neuroanatomical Micromagnetic Resonance Imaging", Brain Mapping: The Methods, pp. 147-166, Academic Press (1996).
Picard, et al., "Overexpression of the Ferritin H Subunit in Cultured Erythroid Cells Changes the Intracellular Iron Distributon". Blood, vol. 87, No. 5, 1996: pp. 2057-2064.
Picard, et al., "Role of Ferritin in the Control of the Labile Iron Pool in Murine Erythroleukemia Cells", The Journal of Biological Chemistry, vol. 273, No. 25, pp. 15382-15386, 1998.
Rudin, Mark., "Target watching with a beady eye", Nature Biotechnology, vol. 18, p. 383 (2000).
Sadun, et al., "First Application of Extremely High-resolution Magnetic Resonance Imaging to Study Microscopic Features of Normal and LHON Human Optic Nerve", Ophthalmology vol. 109, No. 6, 2002. pp. 1085-1091.
Strausberg, R., Direct Submission, Database GeneEmbl. Acession No. BC016009, *Homo sapiens* (human), Oct. 29, 2001, p. 1 bridging p. 2.
Streicher, et al., "3D modelling ofgene expression patterns", Trends in Biotechnology vol. 19, No. 4, (2001). p. 145-148.

Trinder, et al., "Transferrin receptor 2. a new molecule in iron metabolism", The International Journal of Biochemistry & Cell Biology 35 (2003) p. 292-296.

Walter, G., et al., "Noninvasive measurement of gene expression in skeletal muscle," PNAS, 97(10):5151-5155 (2000).

Weissleder, et al., "Molecular Imaging", Molecular Imaging Radiology, 2001, vol. 219, No. 2. pp. 316-333.

Weissleder, R., et al., "MR Imaging and Scintigraphy of Gene Expression through Melanin Induction," Radiology, 204:425-429 (1997).

Zhou, et al., "HFE gene knockout produces mouse model of hereditary hemochromatosis", Proc. Natl. Acad. Sci. USA, vol. 95, pp. 2492-2497, 1998.

* cited by examiner

Figure 6: Human Ferritin Heavy Chain Nucleic Acid Sequence (Acc. No. BC016009) (SEQ ID NO:1)

```
  1 ggggagacgt tcttcgccga gagtcgtcgg ggtttcctgc ttcaacagtg cttggacgga
 61 acccggcgct cgttccccac cccggccggc cgcccatagc cagccctccg tcacctcttc
121 accgcaccct cggactgccc caaggccccc gccgccgctc cagcgccgcg cagccaccgc
181 cgccgccgcc gcctctcctt agtcgccgcc atgacgaccg cgtccacctc gcaggtgcgc
241 cagaactacc accaggactc agaggccgcc atcaaccgcc agatcaacct ggagctctac
301 gcctcctacg tttacctgtc catgtcttac tactttgacc gcgatgatgt ggctttgaag
361 aactttgcca aatactttct tcaccaatct catgaggaga gggaacatgc tgagaaactg
421 atgaagctgc agaaccaacg aggtggccga atcttccttc aggatatcaa gaaaccagac
481 tgtgatgact gggagagcgg gctgaatgca atggagtgtg cattacattt ggaaaaaaat
541 gtgaatcagt cactactgga actgcacaaa ctggccactg acaaaaatga cccccatttg
601 tgtgacttca ttgagacaca ttacctgaat gagcaggtga agccatcaa agaattgggt
661 gaccacgtga ccaacttgcg caagatggga gcgcccgaat ctggcttggc ggaatatctc
721 tttgacaagc acaccctggg agacagtgat aatgaaagct aagcctcggg ctaatttccc
781 catagccgtg gggtgacttc cctggtcacc aaggcagtgc atgcatgttg gggtttcctt
841 tacctttct ataagttgta ccaaaacatc cacttaagtt ctttgatttg taccattcct
901 tcaaataaag aaatttggta ccctcaaaaa aaaaaaaaaa aaaaaaaaaa aaaaa
```

Figure 7: Human Ferritin Heavy Chain Amino Acid Sequence (Acc. No. AAH16009) (SEQ ID NO:2)

```
  1  mttastsqvr qnyhqdseaa inrqinlely asyvylsmsy yfdrddvalk nfakyflhqs
 61  heerehaekl mklqnqrggr iflqdikkpd cddwesglna mecalhlekn vnqsllelhk
121  latdkndphl cdfiethyln eqvkaikelg dhvtnlrkmg apesglaeyl fdkhtlgdsd
181  nes
```

Figure 8: Human Ferritin Light Chain cDNA Sequence (Acc. No. XM_050469) (SEQ ID NO:3)

```
  1 tgcatcaaaa agctttattt ccatttggtc caaggcttgt taggatagtt aagaaagctg
 61 cctattggct ggagggagag gcttaggcag aagccctatt actttgcaag gggcccttca
121 gaagtcgctg ggctcagaag gctcttagtc gtgcttgaga gtgagccttt cgaagagata
181 ctcgcccagc ccagcctccg ggccacccag cctgtggagg ttggtcaggt ggtcacccat
241 cttcttgata agcttcactt cctcatctag gaagtgagtc tccaggaagt cacagagatg
301 ggggtccgtg cgggcagaac ccagggcatg aagatccaaa agggcctggt tcagcttttt
361 ctccagggcc atggcagctt tcatggcgtc tggggtttta ccccactcat cttcagctgg
421 cttcttgatg tcctggaaga gagcgcggcc gccacgctgg ttttgcatct tcaggagacg
481 ctcgtagccc tcgcgcttct cctcggccaa ttcgcggaag aagtggctca cgccttccag
541 agccacatca tcgcggtcga aatagaagcc cagagagagg taggtgtagg aggcctgcag
601 gtacaaattg accaggctgt tgacggctgc ctccacgtcg gtggaataat tctgacgaat
661 ctgggagctc atggttggtt ggcaagaagg agctaaccac aaaaacggtg ctggcaggtc
721 ccagaagcag gagatggccg agaagatggt cccggaggtt gcaagcggag aggaaatcgg
781 agggcggtcg gaggctggaa gagagtcccc ggatctgttc cgtccaaaca ctgttgaagc
841 aagagacaga cccgcgggac
```

Figure 9: Human Ferritin Light Chain Amino Acid Sequence (Acc. No. XP_050469) (SEQ ID NO:4)

```
  1 mgvragrtqg mkiqkglvql flqghgsfhg vwgftplifs wlldvleesa aatlvlhlqe
 61 tlvalalllg qfaeevahaf qshiiaveie aqrevgvggl qvqidqavdg clhvggiilt
121 nlgahgwlar rs
```

Figure 10: Mus musculus ferritin heavy chain cDNA sequence (Acc. No. NM_010239.1) (SEQ ID NO:5)

```
  1 cagacgttct cgcccagagt cgccgcggtt tcctgcttca acagtgcttg aacggaaccc
 61 ggtgctcgac ccctccgacc cccgccggcc gcttcgagcc tgagcccttt gcaacttcgt
121 cgttccgccg ctccagcgtc gccaccgcgc ctcgccccgc cgccaccatg accaccgcgt
181 ctccctcgca agtgcgccag aactaccacc aggacgcgga ggctgccatc aaccgccaga
241 tcaacctgga gttgtatgcc tcctacgtct atctgtctat gtcttgttat tttgaccgag
301 atgatgtggc tctgaagaac tttgccaaat actttctcca ccaatctcat gaggagaggg
361 agcatgccga gaaactgatg aagctgcaga accagcgagg tggccgaatc ttcctgcagg
421 atataaagaa accagaccgt gatgactggg agagcgggct gaatgcaatg gagtgtgcac
481 tgcacttgga aaagagtgtg aatcagtcac tactggaact gcacaaactg gctactgaca
541 agaatgatcc ccacttatgt gacttcattg agacgtatta tctgagtgaa caggtgaaat
601 ccattaaaga actgggtgac cacgtgacca acttacgcaa gatgggtgcc cctgaagctg
661 gcatggcaga atatctcttt gacaagcaca ccctgggaca cggtgatgag agctaagctg
721 acttccccaa agccacgtga cttactggt cactgaggca gtgcatgcat gtcaggctgc
781 cttcatcttt tctataagtt gcaccaaaac atctgcttaa gttctttaat ttgtaccatt
841 tcttcaaata aagaattttg gtaccc
```

Figure 11: Mus musculus ferritin heavy chain amino acid sequence (NP_034369.1) (SEQ ID NO:6)

```
  1 mttaspsqvr qnyhqdaeaa inrqinlely asyvylsmsc yfdrddvalk nfakyflhqs
 61 heerehaekl mklqnqrggr iflqdikkpd rddwesglna mecalhleks vnqsllelhk
121 latdkndphl cdfietyyls eqvksikelg dhvtnlrkmg apeagmaeyl fdkhtlghgd
181 es
```

Figure 12: Mus musculus ferritin light chain 1 cDNA sequence (NM_010240.1) (SEQ ID NO:7)

```
  1 cagcgccttg gaggtcccgt ggatctgtgt acttgcttca acagtgtttg aacggaacag
 61 acccggggat tcccactgta ctcgcttcca gccgccttta caagtctctc cagtcgcagc
121 ctccgggacc atctcctcgc tgccttcagc tcctaggacc agtctgcacc gtctcttcgc
181 ggttagctcc tactccggat cagccatgac ctctcagatt cgtcagaatt attccaccga
241 ggtggaagct gccgtgaacc gcctggtcaa cttgcacctg cgggcctcct acacctacct
301 ctctctgggc ttcttttttg atcgggatga cgtggctctg gaaggcgtag gccacttctt
361 ccgcgaattg gccgaggaga agcgcgaggg cgcggagcgt ctcctcgagt ttcagaacga
421 tcgcggggc cgtgcactct tccaggatgt gcagaagcca tctcaagatg aatggggtaa
481 aacccaggag gccatggaag ctgccttggc catggagaag aacctgaatc aggccctctt
541 ggatctgcat gccctgggtt ctgcccgcac ggaccctcat ctctgtgact tcctggaaag
601 ccactatctg gataaggagg tgaaactcat caagaagatg ggcaaccatc tgaccaacct
661 ccgcagggtg gcggggccac aaccagcgca gactggcgcg cccaggggt ctctgggcga
721 gtatctcttt gagcgcctca ctctcaagca cgactaggag gcctctgtac cttccaaggg
781 gctcccccct ctgctctgca ccagcccgcc ctgggacctc cacctgaatg aacctctcaa
841 gccactaggc agctttgtaa ccgtcctcca gcctctgtca agtcttggac caagtaaaaa
901 taaagctttt tgagaccccg
```

Figure 13: Mus musculus ferritin light chain 1 amino acid sequence (NP_034370.1) (SEQ ID NO:8)

```
  1 mtsqirqnys teveaavnrl vnlhlrasyt ylslgfffdr ddvalegvgh ffrelaeekr
 61 egaerllefq ndrggralfq dvqkpsqdew gktqeameaa lameknlnqa lldlhalgsa
121 rtdphlcdfl eshyldkevk likkmgnhlt nlrrvagpqp aqtgapqgsl geylferltl
181 khd
```

Figure 14: Mus musculus ferritin light chain 2 cDNA sequence (NM_008049.1) (SEQ ID NO:9)

```
  1 ggaagactgt aaaagtcttg tcattttgtt cagtgaagtc ccctcattca catcaccaag
 61 gatgatgaca gtctctccag tcgccgcagc ctccgggacc atctccttgc cgccttccgg
121 tcctaggacc agccagcccc gtcttcgcgg ttagctccat actccggatc agccatgacc
181 tctcagattc gtcagaatta ttccaccgaa gtggaagctg ccgtgaaccg cctggtcaac
241 ttgcacctgc gggcctctta cacctacctc tctctgggct tctttttga tcgggatgac
301 gtggctttgg aaggcgtagg ccacttcttc cgcgaattgg ccgaggagaa gcgcgagggc
361 gcggagcgtc tcctcaagtt gcagaacgaa cgcgggggcc gtgcactctt ccaggatgtg
421 cagaagccat ctcaagatga gtggggtaaa accctggagg ccatccaagc tgccttgcgc
481 ctggagaaga acctgaacca ggccctcttg gatctgcacg ccctgggctc tgcccgcaca
541 gaccctcacc tctgtgactt cttggaaagc cacttcctgg ataaggaggt gaagctcatc
601 aagaagatgg gcaaccacct gaccaacctc cgtagggtgg cagggccaca accagtgcag
661 actggcgtgg cccaggcatc tctgggcgag tatctctttg agcgcctcac tctgaagcac
721 gactaggcct ctgtgccttc caaggggctc cctcctctgc tctgcaccga ccgcctcagc
781 acctccaccc gaatgaacct ctaaagccac taggcagctt tgtaaccgcc ctggagcctc
841 tcccaagtct tggaccaagt aaaaataaa
```

Figure 15: Mus musculus ferritin light chain 2 amino acid sequence (NP_032075.1) (SEQ ID NO:10)

```
  1 mtsqirqnys teveaavnrl vnlhlrasyt ylslgfffdr ddvalegvgh ffrelaeekr
 61 egaerllklq nerggralfq dvqkpsqdew gktleaiqaa lrleknlnqa lldlhalgsa
121 rtdphlcdfl eshfldkevk likkmgnhlt nlrrvagpqp vqtgvaqasl geylferltl
181 khd
```

Figure 16: Rattus norvegicus ferritin subunit H cDNA sequence (NM_012848.1) (SEQ ID NO:11)

```
  1 cgacagtgct tgaacggaac ccggtgctcg acccctccga cccccgccgg ccgctttgag
 61 cctgagccct ttgcaacttc gtcgctccgc cgctccagcg tcgcctccgc gcctcgccca
121 gccgccatca tgaccaccgc gtctccctcg caagtgcgcc agaactacca ccaggactcg
181 gaggctgcca tcaaccgcca gatcaacctg gagttgtatg cctcctacgt ctatctgtcc
241 atgtcttgtt attttgaccg ggatgatgtg gccctgaaga actttgccaa atactttctc
301 catcaatctc atgaagagag ggaacatgct gagaaactga tgaagctgca gaaccagcga
361 ggtggacgaa tcttcctgca ggatataaag aaacctgacc gtgatgactg ggagagcggg
421 ctgaatgcaa tggagtgtgc actgcacttg gaaaagagtg tgaatcagtc actactggaa
481 cttcacaaac tggctactga caagaatgat ccccacttat gtgacttcat tgagacgcat
541 tacctgaatg agcaggtgaa atccattaaa gaactgggtg accacgtgac caacttacgc
601 aagatgggag cccctgaatc tggcatggca gaatatctct tgacaagca caccctggga
661 cacggtgatg agagctaagc tgacgtcccc aaggccatgt gactttactg gtcactgagg
721 cagtgcatgc atgtcaggct gcctttatct tttctataag ttgcaccaaa acatctgctt
781 aaaagttctt taatttgtac catttcttca aataaagaat tttggtaccc
```

Figure 17: Rattus norvegicus ferritin subunit H amino acid sequence (NP_036980.1) (SEQ ID NO:12)

```
  1 mttaspsqvr qnyhqdseaa inrqinlely asyvylsmsc yfdrddvalk nfakyflhqs
 61 heerehaekl mklqnqrggr iflqdikkpd rddwesglna mecalhleks vnqsllelhk
121 latdkndphl cdfiethyln eqvksikelg dhvtnlrkmg apesgmaeyl fdkhtlghgd
181 es
```

Figure 18: Rattus norvegicus ferritin light chain 1 cDNA sequence (NM_022500.1) (SEQ ID NO:13)

NP_071945.1

```
  1 atgacctctc agattcgtca gaattattcc accgaagtgg aagctgccgt gaaccgcctg
 61 gtcaacttgc acctgcgggc ctcttacacc tacctctctc tgggcttctt ttttgatcgg
121 gatgacgtgg ctttggaagg cgtaggccac ttcttccgcg aattggccga ggagaagcgc
181 gagggcgccg agcgtctcct caagttgcag aacgaacgcg ggggccgtgc actcttccag
241 gatgtgcaga agccatctca agatgagtgg ggtaaaaccc tggaggccat ggaagctgcc
301 ttggccctgg agaagaacct gaaccaggcc ctcttggatc tgcacgccct gggctctgcc
361 cgcacagacc ctcacctctg tgacttcttg gaaagccact tcctggataa ggaggtgaag
421 ctcatcaaga agatgggcaa ccacctgacc aacctccgta gggtgcaggg cccacaacca
481 gcgcagactg gcgtggccca ggcatctctg ggcgagtatc tctttgagcg cctcactctg
541 aagcacgact ag
```

Figure 19: Rattus norvegicus ferritin light chain 1 amino acid sequence (NP_071945.1) (SEQ ID NO:14)

```
  1 mtsqirqnys teveaavnrl vnlhlrasyt ylslgfffdr ddvalegvgh ffrelaeekr
 61 egaerllklq nerggralfq dvqkpsqdew gktleameaa laleknlnqa lldlhalgsa
121 rtdphlcdfl eshfldkevk likkmgnhlt nlrrvqgpqp aqtgvaqasl geylferltl
181 khd
```

Figure 20: Homo sapiens transferrin receptor cDNA sequence (NM_003234) (SEQ ID NO:15)

```
   1 ggcggctcgg gacggaggac gcgctagtgt gagtgcgggc ttctagaact acaccgaccc
  61 tcgtgtcctc ccttcatcct gcggggctgg ctggagcggc cgctccggtg ctgtccagca
 121 gccataggga gccgcacggg gagcgggaaa gcggtcgcgg ccccaggcgg ggcggccggg
 181 atggagcggg gccgcgagcc tgtggggaag gggctgtggc ggcgcctcga gcggctgcag
 241 gttcttctgt gtggcagttc agaatgatgg atcaagctag atcagcattc tctaacttgt
 301 ttggtggaga accattgtca tatacccggt tcagcctggc tcggcaagta gatggcgata
 361 acagtcatgt ggagatgaaa cttgctgtag atgaagaaga aaatgctgac aataacacaa
 421 aggccaatgt cacaaaacca aaaggtgta gtggaagtat ctgctatggg actattgctg
 481 tgatcgtctt tttcttgatt ggatttatga ttggctactt gggctattgt aaagggdtag
 541 aaccaaaaac tgagtgtgag agactggcag gaaccgagtc tccagtgagg gaggagccag
 601 gagaggactt ccctgcagca cgtcgcttat attgggatga cctgaagaga aagttgtcgg
 661 agaaactgga cagcacagac ttcaccagca ccatcaagct gctgaatgaa aattcatatg
 721 tccctcgtga ggctggatct caaaaagatg aaaatcttgc gttgtatgtt gaaaatcaat
 781 ttcgtgaatt taaactcagc aaagtctggc gtgatcaaca ttttgttaag attcaggtca
 841 aagacagcgc tcaaaactcg gtgatcatag ttgataagaa cggtagactt gtttacctgg
 901 tggagaatcc tgggggttat gtggcgtata gtaaggctgc aacagttact ggtaaactgg
 961 tccatgctaa ttttggtact aaaaagatt ttgaggattt atacactcct gtgaatggat
1021 ctatagtgat tgtcagagca gggaaaatca cctttgcaga aaaggttgca aatgctgaaa
1081 gcttaaatgc aattggtgtg ttgatataca tggaccagac taaatttccc attgttaacg
1141 cagaactttc attcttgga catgctcatc tggggacagg tgacccttac acacctggat
1201 tcccttcctt caatcacact cagtttccac catctcggtc atcaggattg cctaatatac
1261 ctgtccagac aatctccaga gctgctgcag aaaagctgtt tgggaatatg gaaggagact
1321 gtccctctga ctggaaaaca gactctacat gtaggatggt aacctcagaa agcaagaatg
1381 tgaagctcac tgtgagcaat gtgctgaaag agataaaaat tcttaacatc tttggagtta
1441 ttaaaggctt tgtagaacca gatcactatg ttgtagttgg ggcccagaga gatgcatggg
1501 gccctggagc tgcaaaatcc ggtgtaggca cagctctcct attgaaactt gcccagatgt
1561 tctcagatat ggtcttaaaa gatgggtttc agcccagcag aagcattatc tttgccagtt
1621 ggagtgctgg agactttgga tcggttggtg ccactgaatg gctagaggga tacctttcgt
1681 ccctgcattt aaaggctttc acttatatta tctggataa agcggttctt ggtaccagca
1741 acttcaaggt ttctgccagc ccactgttgt atacgcttat tgagaaaaca atgcaaaatg
1801 tgaagcatcc ggttactggg caatttctat atcaggacag caactgggcc agcaaagttg
1861 agaaactcac tttagacaat gctgctttcc ctttccttgc atattctgga atcccagcag
1921 tttctttctg tttttgcgag gacacagatt atccttattt gggtaccacc atggacacct
1981 ataaggaact gattgagagg attcctgagt tgaacaaagt ggcacgagca gctgcagagg
2041 tcgctggtca gttcgtgatt aaactaaccc atgatgttga attgaacctg gactatgaga
2101 ggtacaacag ccaactgctt tcatttgtga gggatctgaa ccaatacaga gcagacataa
2161 aggaaatggg cctgagttta cagtggctgt attctgctcg tggagacttc ttccgtgcta
2221 cttccagact aacaacagat ttcgggaatg ctgagaaaac agacagattt gtcatgaaga
2281 aactcaatga tcgtgtcatg agagtggagt atcacttcct ctctccctac gtatctccaa
2341 aagagtctcc tttccgacat gtcttctggg gctccggctc tcacacgctg ccagctttac
2401 tggagaactt gaaactgcgt aaacaaaata cggtgctttt aatgaaacg ctgttcagaa
2461 accagttggc tctagctact tggactattc agggagctgc aaatgccctc tctggtgacg
2521 tttgggacat tgacaatgag ttttaaatgt gatacccata gcttccatga aacagcagg
2581 gtagtctggt ttctagactt gtgctgatcg tgctaaattt tcagtagggc tacaaaacct
2641 gatgttaaaa ttccatccca tcatcttggt actactagat gtctttaggc agcagctttt
2701 aatacagggt agataacctg tacttcaagt taaagtgaat aaccacttaa aaaatgtcca
2761 tgatggaata ttcccctatc tctagaattt taagtgcttt gtaatgggaa ctgcctcttt
2821 cctgttgttg ttaatgaaaa tgtcagaaac cagttatgtg aatgatctct ctgaatccta
2881 agggctggtc tctgctgaag gttgtaagtg gttcgcttac tttgagtgat cctccaactt
2941 catttgatgc taaataggag ataccaggtt gaaagacctc tccaaatgag atctaagcct
3001 ttccataagg aatgtagcag gtttcctcat tctgaaaga aacagttaac tttcagaaga
3061 gatgggcttg ttttcttgcc aatgaggtct gaaatggagg tccttctgct ggataaaatg
3121 aggttcaact gttgattgca ggaataaggc cttaatatgt taacctcagt gtcatttatg
```

```
3181 aaaagagggg accagaagcc aaagacttag tatattttct tttcctctgt cccttccccc
3241 ataagcctcc atttagttct ttgttatttt tgtttcttcc aaagcacatt gaaagagaac
3301 cagtttcagg tgtttagttg cagactcagt ttgtcagact ttaaagaata atatgctgcc
3361 aaattttggc caaagtgtta atcttagggg agagctttct gtccttttgg cactgagata
3421 tttattgttt atttatcagt gacagagttc actataaatg gtgtttttt aatagaatat
3481 aattatcgga agcagtgcct tccataatta tgacagttat actgtcggtt ttttttaaat
3541 aaaagcagca tctgctaata aaacccaaca gatactggaa gttttgcatt tatggtcaac
3601 acttaagggt tttagaaaac agccgtcagc caaatgtaat tgaataaagt tgaagctaag
3661 atttagagat gaattaaatt taattagggg ttgctaagaa gcgagcactg accagataag
3721 aatgctggtt ttcctaaatg cagtgaattg tgaccaagtt ataaatcaat gtcacttaaa
3781 ggctgtggta gtactcctgc aaaattttat agctcagttt atccaaggtg taactctaat
3841 tcccatttgc aaaatttcca gtaccttgt cacaatccta acacattatc gggagcagtg
3901 tcttccataa tgtataaaga acaaggtagt ttttacctac cacagtgtct gtatcggaga
3961 cagtgatctc catatgttac actaagggtg taagtaatta tcgggaacag tgtttcccat
4021 aattttcttc atgcaatgac atcttcaaag cttgaagatc gttagtatct aacatgtatc
4081 ccaactccta taattcccta tcttttagtt ttagttgcag aaacattttg tggtcattaa
4141 gcattgggtg ggtaaattca accactgtaa aatgaaatta ctacaaaatt tgaaatttag
4201 cttgggtttt tgttacctt atggtttctc caggtcctct acttaatgag atagcagcat
4261 acatttataa tgtttgctat tgacaagtca ttttaattta tcacattatt tgcatgttac
4321 ctcctataaa cttagtgcgg acaagtttta atccagaatt gacctttga cttaaagcag
4381 agggactttg tatagaaggt ttgggggctg tggggaagga gagtcccctg aaggtctgac
4441 acgtctgcct acccattcgt ggtgatcaat taaatgtagg tatgaataag ttcgaagctc
4501 cgtgagtgaa ccatcatata aacgtgtagt acagctgttt gtcatagggc agttggaaac
4561 ggcctcctag ggaaaagttc atagggtctc ttcaggttct tagtgtcact tacctagatt
4621 tacagcctca cttgaatgtg tcactactca cagtctcttt aatcttcagt tttatcttta
4681 atctcctctt ttatcttgga ctgacattta gcgtagctaa gtgaaaaggt catagctgag
4741 attcctggtt cgggtgttac gcacacgtac ttaaatgaaa gcatgtggca tgttcatcgt
4801 ataacacaat atgaatacag ggcatgcatt ttgcagcagt gagtctcttc agaaaaccct
4861 tttctacagt taggggttgag ttacttccta tcaagccagt acgtgctaac aggctcaata
4921 ttcctgaatg aaatatcaga ctagtgacaa gctcctggtc ttgagatgtc ttctcgttaa
4981 ggagtagggc cttttggagg taaaggtata
```

Figure 20 con't

Figure 21: Homo sapiens transferrin receptor amino acid sequence (NP_003225) (SEQ ID NO:16)

```
  1 mmdqarsafs nlfggeplsy trfslarqvd gdnshvemkl avdeeenadn ntkanvtkpk
 61 rcsgsicygt iavivfflig fmigylgyck gvepktecer lagtespvre epgedfpaar
121 rlywddlkrk lsekldstdf tstikllnen syvpreagsq kdenlalyve nqfrefklsk
181 vwrdqhfvki qvkdsaqnsv iivdkngrlv ylvenpggyv ayskaatvtg klvhanfgtk
241 kdfedlytpv ngsivivrag kitfaekvan aeslnaigvl iymdqtkfpi vnaelsffgh
301 ahlgtgdpyt pgfpsfnhtq fppsrssglp nipvqtisra aaeklfgnme gdcpsdwktd
361 stcrmvtses knvkltvsnv lkeikilnif gvikgfvepd hyvvvgaqrd awgpgaaksg
421 vgtalllkla qmfsdmvlkd gfqpsrsiif aswsagdfgs vgatewlegy lsslhlkaft
481 yinldkavlg tsnfkvsasp llytliektm qnvkhpvtgq flyqdsnwas kvekltldna
541 afpflaysgi pavsfcfced tdypylgttm dtykelieri pelnkvaraa aevagqfvik
601 lthdvelnld yerynsqlls fvrdlnqyra dikemglslq wlysargdff ratsrlttdf
661 gnaektdrfv mkklndrvmr veyhflspyv spkespfrhv fwgsgshtlp allenlklrk
721 qnngafnetl frnqlalatw tiqgaanals gdvwdidnef
```

Figure 22: Homo sapiens transferrin receptor 2 cDNA sequence (NM_003227) (SEQ ID NO:17)

```
   1 ctgcaggctt caggagggga cacaagcatg gagcggcttt ggggtctatt ccagagagcg
  61 caacaactgt ccccaagatc ctctcagacc gtctaccagc gtgtggaagg cccccggaaa
 121 gggcacctgg aggaggaaga ggaagacggg gaggaggggg cggagacatt ggcccacttc
 181 tgccccatgg agctgagggg ccctgagccc ctgggctcta gacccaggca gccaaacctc
 241 attccctggg cggcagcagg acggagggct gcccctacc tggtcctgac ggccctgctg
 301 atcttcactg gggccttcct actgggctac gtcgccttcc gagggtcctg ccaggcgtgc
 361 ggagactctg tgttggtggt cagtgaggat gtcaactatg agcctgacct ggatttccac
 421 cagggcagac tctactggag cgacctccag gccatgttcc tgcagttcct ggggaggggg
 481 cgcctggagg acaccatcag gcaaaccagc cttcgggaac gggtggcagg ctcggccggg
 541 atggccgctc tgactcagga cattcgcgcg gcgctctccc gccagaagct ggaccacgtg
 601 tggaccgaca cgcactacgt ggggctgcaa ttcccggatc cggctcaccc caacaccctg
 661 cactgggtcg atgaggccgg aaggtcgga gagcagctgc cgctggagga ccctgacgtc
 721 tactgcccct acagcgccat cggcaacgtc acgggagagc tggtgtacgc ccactacggg
 781 cggcccgaag acctgcagga cctgcgggcc aggggcgtgg atccagtggg ccgcctgctg
 841 ctggtgcgcg tggggtgat cagcttcgcc cagaaggtga ccaatgctca ggacttcggg
 901 gctcaaggag tgctcatata cccagagcca gcggacttct cccaggaccc acccaagcca
 961 agcctgtcca gccagcaggc agtgtatgga catgtgcacc tgggaactgg agacccctac
1021 acacctggct tccttccttt caatcaaacc cagaagctca aaggccctgt ggcccccaa
1081 gaatggcagg ggagcctcct aggctcccct tatcacctgg gccccgggcc acgactgcgg
1141 ctagtggtca caatcacag gacctccacc cccatcaaca acatcttcgg ctgcatcgaa
1201 ggccgctcag agccagatca ctacgttgtc atcggggccc agagggatgc atggggccca
1261 ggagcagcta atccgctgt ggggacggct atactcctgg agctggtgcg gacctttttc
1321 tccatggtga gcaacggctt ccggccccgc agaagtctcc tcttcatcag ctgggacggt
1381 ggtgactttg aagcgtgggg ctccacggag tggctagagg gctacctcag cgtgctgcac
1441 ctcaaagccg tagtgtacgt gagcctggac aacgcagtgc tggggatga caagtttcat
1501 gccaagacca gccccttct gacaagtctc attgagagtg tcctgaagca ggtggattct
1561 cccaaccaca gtgggcagac tctctatgaa caggtggtgt tcaccaatcc cagctggat
1621 gctgaggtga tccggccct acccatggac agcagtgcct attccttcac ggcctttgtg
1681 ggagtccctg ccgtcgagtt ctcctttatg gaggacgacc aggcctaccc attcctgcac
1741 acaaaggagg acacttatga aacctgcat aaggtgctgc aaggccgcct gcccgccgtg
1801 gcccaggccg tggcccagct cgcagggcag ctcctcatcc ggctcagcca cgatcgcctg
1861 ctgccctcg acttcggccg ctacggggac gtcgtcctca ggcacatcgg aaacctcaac
1921 gagttctctg ggacctcaa ggcccgcggg ctgaccctgc agtgggtgta ctcggcgcgg
1981 ggggactaca tccgggcggc ggaaaagctg cggcaggaga tctacagctc ggaggagaga
2041 gacgagcgac tgacacgcat gtacaacgtg cgcataatgc ggatcccct ctctgcgcag
2101 gtggagttct acttcctttc ccagtacgtg tcgccagccg actccccgtt ccgccacatc
2161 ttcatgggcc gtggagacca cacgctgggc gccctgctgg accacctgcg gctgctgcgc
2221 tccaacagct ccgggacccc cggggccacc tcctccactg gcttccagga gagccgtttc
2281 cggcgtcagc tagccctgct cacctggacg ctgcaagggg cagccaatgc gcttagcggg
2341 gatgtctgga acattgataa caacttctga ggccctgggg atcctcacat ccccgtcccc
2401 cagtcaagag ctcctctgct cctcgcttga atgattcagg gtcagggagg tggctcagag
2461 tccacctctc attgctgatc aatttctcat taccctaca catctctcca cgg
```

Figure 23: Homo sapiens transferrin receptor 2 amino acid sequence (NM_003218) (SEQ ID NO:18)

```
  1 merlwglfqr aqqlsprssq tvyqrvegpr kghleeeeed geegaetlah fcpmelrgpe
 61 plgsrprqpn lipwaaagrr aapylvltal liftgafllg yvafrgscqa cgdsvlvvse
121 dvnyepdldf hqgrlywsdl qamflqflge grledtirqt slrervagsa gmaaltqdir
181 aalsrqkldh vwtdthyvgl qfpdpahpnt lhwvdeagkv geqlpledpd vycpysaign
241 vtgelvyahy grpedlqdlr argvdpvgrl llvrvgvisf aqkvtnaqdf gaqgvliype
301 padfsqdppk pslssqqavy ghvhlgtgdp ytpgfpsfnq tqklkgpvap qewqgsllgs
361 pyhlgpgprl rlvvnnhrts tpinnifgci egrsepdhyv vigaqrdawg pgaaksavgt
421 aillelvrtf ssmvsngfrp rrsllfiswd ggdfgsvgst ewlegylsvl hlkavvyvsl
481 dnavlgddkf haktspllts liesvlkqvd spnhsgqtly eqvvftnpsw daevirplpm
541 dssaysftaf vgvpavefsf meddqaypfl htkedtyenl hkvlqgrlpa vaqavaqlag
601 qllirlshdr llpldfgryg dvvlrhignl nefsgdlkar gltlqwvysa rgdyiraaek
661 lrqeiyssee rderltrmyn vrimriplsa qvefyflsqy vspadspfrh ifmgrgdhtl
721 galldhlrll rsnssgtpga tsstgfqesr frrqlalltw tlqgaanals gdvwnidnnf
```

Figure 24: Mus musculus transferrin receptor coding sequence (NM_011638) (SEQ ID NO:19)

```
   1 atgatggatc aagccagatc agcattctct aacttgtttg gtggggaacc attgtcatac
  61 acccggttta gccttgctcg gcaagtagat ggagataaca gtcatgtgga gatgaaactg
 121 gctgcagatg aagaagaaaa tgccgacaat aacatgaagg ctagtgtcag aaaacccaag
 181 aggtttaatg aagactctg  ctttgcagct attgcactag tcatttctct cttgattgga
 241 ttcatgagtg gctacctggg ctattgtaag cgtgtagaac aaaaagagga gtgtgtgaaa
 301 ctggctgaaa cggaggagac agacaagtca gaaaccatgg aaacagagga tgttcctaca
 361 tcatctcgct tatattgggc agacctcaaa acactgttgt cagagaagtt gaactccata
 421 gagtttgctg acaccatcaa gcagctgagc cagaatacat acactcctcg tgaggctgga
 481 tctcaaaaag atgaaagtct tgcctattat attgaaaatc agttccatga atttaaattc
 541 agcaaagtct ggcgagatga acactatgtg aagattcaag tgaaaagcag cattggtcaa
 601 aacatggtga ccatagtgca gtcaaatggt aacttagacc cagtggagtc tcccgagggt
 661 tatgtggcat tcagtaaacc tacagaagtt tctggtaaac tggtccatgc taattttggc
 721 actaaaaagg actttgaaga actaagttat tctgtgaatg gatctttagt gattgttaga
 781 gcagggaaa  ttacttttgc agaaaaggtt gcaaatgccc aaagctttaa tgcaattggt
 841 gtcctcatat acatggacaa gaataaattc cccgttgttg aggcagacct tgcactcttt
 901 ggacatgctc atctaggaac tggtgatcca tacacacctg gctttccttc tttcaatcat
 961 actcagtttc cgccatctca gtcatcaggg ttgcctaata tacctgtgca acaatctca
1021 agagctgctg cagaaaagct atttggaaaa atggaaggaa gctgtcctgc tagatggaac
1081 atagattctt catgtaagct ggaactttca cagaatcaaa atgtgaagct cattgtgaaa
1141 aacgtactga agaaagaag  aatacttaac atctttggag ttattaaagg ttatgaggaa
1201 ccagaccgtt atgttgtagt aggagcccag agagacgctt tgggtgctgg tgttgcggcg
1261 aagtccagtg tgggaacagg tcttctgttg aaacttgccc aagtattctc agatatgatt
1321 tcaaaagatg gatttagacc cagcagaagt ataatctttg ccagctggac tgcaggcgac
1381 tttggagctg ttggtgccac tgagtggttg gagggatacc tttcatcttt gcatttaaaa
1441 gctttcactt atattaattt ggataaagtt gtccttggta ctagtaactt caaagtttct
1501 gccagcccct tattatatac acttatggga aagataatgc aagatgtaaa gcatccagtt
1561 gatggaaaat ctctatatag agacagcaat tggattagca agttgagaa  acttttcctt
1621 gacaatgctg catatcctt  ccttgcatat tctggaatcc agcagtttc  ttttgtttt
1681 tgtgaggatg cagactatcc ttatttgggc actagattgg atacctatga ggcattgact
1741 cagaaagttc ctcagctcaa ccaaatggtt cgtacagcag cggaagtggc tggtcagctc
1801 attattaaac ttacccatga cgttgaattg aacctggact atgagatgta acagcaaa
1861 ctactgtcat ttatgaagga tctgaaccag ttcaaaacag atatcaggga tatgggtcta
1921 agtctacagt ggctgtattc cgctcgtgga gactacttcc gtgctacttc tagactaaca
1981 actgattttc ataatgctga gaaacaaac  agatttgtca tgagggaaat caatgatcgt
2041 attatgaaag tggagtatca cttcctgtcg ccctatgtat ctccaagaga gtctcctttc
2101 cgacatatct tctgggctc  tggctctcac actctctcag ctttagtgga gaacttgaag
2161 cttcgtcaaa aaatattac  tgcttttaat gaaaccctct tcagaaacca gttggccctg
2221 gctacttgga ctattcaggg agtcgcaaat gccctctctg gtgacatttg gaatattgac
2281 aatgagtttt aa
```

Figure 25: Mus musculus transferrin receptor amino acid sequence (NP_035768) (SEQ ID NO:20)

```
  1 mmdqarsafs nlfggeplsy trfslarqvd gdnshvemkl aadeeenadn nmkasvrkpk
 61 rfngrlcfaa ialvifflig fmsgylgyck rveqkeecvk laeteetdks etmetedvpt
121 ssrlywadlk tllseklnsi efadtikqls qntytpreag sqkdeslayy ienqfhefkf
181 skvwrdehyv kiqvkssigq nmvtivqsng nldpvespeg yvafskptev sgklvhanfg
241 tkkdfeelsy svngslvivr ageitfaekv anaqsfnaig vliymdknkf pvveadlalf
301 ghahlgtgdp ytpgfpsfnh tqfppsqssg lpnipvqtis raaaeklfgk megscparwn
361 idsscklels qnqnvklivk nvlkerriln ifgvikgyee pdryvvvgaq rdalgagvaa
421 kssvgtglll klaqvfsdmi skdgfrpsrs iifaswtagd fgavgatewl egylsslhlk
481 aftyinldkv vlgtsnfkvs aspllytlmg kimqdvkhpv dgkslyrdsn wiskveklsf
541 dnaaypflay sgipavsfcf cedadypylg trldtyealt qkvpqlnqmv rtaaevagql
601 iiklthdvel nldyemynsk llsfmkdlnq fktdirdmgl slqwlysarg dyfratsrlt
661 tdfhnaektn rfvmreindr imkveyhfls pyvsprespf rhifwgsgsh tlsalvenlk
721 lrqknitafn etlfrnqlal atwtiqgvan alsgdiwnid nef
```

Figure 26: Mus musculus transferrin receptor 2 nucleic acid sequence (NM_015799) (SEQ ID NO:21)

```
   1 aaaaaaaaaa attgattgtt ttgcagtctg cccgcaacag tggggtttgt ggaaagattg
  61 agttcaggag ggggcacaag catggagcaa cgttggggtc tacttcggag agtgcaacag
 121 tggtccccaa gaccctctca gaccatctac agacgcgtgg aaggccctca gctggagcac
 181 ctggaggagg aagacaggga ggaaggggcg gagcttcctg cccagttctg ccccatggaa
 241 ctcaaaggcc ctgagcactt aggctcctgt cccgggaggt caattcccat accctgggct
 301 gcagcaggtc gaaaggctgc cccctatctg gtcctgatca ccctgctaat cttcactggg
 361 gccttcctcc taggctacgt ggcctttcga gggtcctgcc aggcgtgtgg ggactccgtg
 421 ttggtggtcg atgaagatgt caaccctgag gactccggcc ggaccacgtt gtactggagc
 481 gacctccagg ccatgtttct ccggttcctt ggggagggc gcatggaaga caccatcagg
 541 ctgaccagcc tccgggaacg cgtggctggc tcagccagaa tggccaccct ggtccaagat
 601 atcctcgata agctctcgcg ccagaagctg gaccacgtgt ggactgacac gcactacgtg
 661 ggacttcagt tcccagatcc ggctcacgct aacaccctgc actgggtgga tgcagacggg
 721 agcgtccagg agcagctacc gctggaggat ccggaagtct actgtcccta cagcgccacc
 781 ggcaacgcca cgggcaagct ggtgtaccgc cactacgggc ggtcggagga cctacaggac
 841 ctaaaagcca agggcgtgga gctggccggc agcctcctgc tagtgcgagt tggaattact
 901 agcttcgccc agaaggtagc cgttgcccag gactttgggg ctcaaggagt gctgatatac
 961 cctgacccat cagacttctc ccaggatccc acaagccag gcctgtctag ccaccaggct
1021 gtgtacggac atgtgcacct gggaactgga gacccttaca cacctggctt cccgtccttc
1081 aatcaaaccc agttccctcc agtagaatca tcaggccttc ccagcatccc cgcccagccc
1141 atcagtgctg acattgctga tcaattgctc aggaaactca caggccccgt ggctccccag
1201 gagtggaaag gtcacctctc aggctctcct tatcggctgg gacctgggcc cgacttacgc
1261 cttgtggtca acaaccacag agtctctacc cccatcagta acatctttgc gtgcatcgag
1321 ggctttgcag agccagatca ctatgttgtc attggggccc agagggatgc atggggccca
1381 ggagcagcca agtctgcagt ggggactgcc atcctgctgg agctggttcg gaccttctct
1441 tccatggtca gcaatgggtt cagacctcga agaagtcttt tgttcattag ctgggacgga
1501 ggtgactttg gcagcgttgg gagccacagag tggttggagg gctacctcag cgtgctacac
1561 ctcaaagctg ttgtgtacgt gagcctggac aactccgtgt tgggagatgg caaattccat
1621 gctaagacca gcccccttct cgtcagcctc attgagaata tcttgaagca ggtggactcc
1681 cctaaccata gtggacagac cctctatgaa caagtggcac tcacccaccc cagctgggat
1741 gctgaagtga ttcagcccct gccatggac agcagtgcat attccttcac agcctttgcg
1801 ggggtcccag ctgtggagtt ctccttcatg gaggatgatc gggtgtaccc attcctgcac
1861 acggaggagg acacatatga gaatctgcac aagatgctgc gaggtcgcct gcccgccgtg
1921 gtccaggcag tggctcagct cgcgggccag ctcctcatcc gactgagcca cgatcaccta
1981 ctgccgctag acttcggccg ctatggagac gtggttctca ggcacatcgg caacctcaat
2041 gagttctctg ggacctcaa ggagcgcggg ctgaccctgc agtgggtgta ctctgcaagg
2101 ggggactaca tccgtgcggc ggaaaagctg cggaaggaga tctacagctc ggagcggaac
2161 gatgagcgtc tgatgcgcat gtacaacgtg cgcatcatga gggtggagtt ctacttcctg
2221 tcccagtatg tgtcgccagc cgactcccca ttccgccaca ttttcctagg ccaaggcgac
2281 cacactttgg gtgccctggt agaccacctg cggatgctgc gcgccgatgg ctcaggagcc
2341 gcctcttccc ggttgacagc aggtctgggc ttccaggaga gtcgcttccg gcgccagctg
2401 gcgctgctca cctggacact gcaggggca gccaacgctc tcagtggcga cgtttggaac
2461 attgacaata acttttgaag ccaaaagccc tccatgggcc ccacgtgatt ctcctttctc
2521 cctctttgag tggtgcaggc aaaggaggtg cctgagattg taacctattc ttaacaccct
2581 tggtcctgca atgctggtgc gccatatttt ctcagtgtgg ttgtcatgcc gttgcttacc
2641 cagaaagcgg tttcttccc atcacaggcc cttctgtctt caggagcaaa gttccccata
2701 tctagagact atctagatgc tgggatctga tcagctctct tagagagtga gatggacagc
2761 gtcattattt tatgacacat gagctacggt atgtgagcag cccaaggga ttagatgtca
2821 ataaccaat tgtaacccca aaaaaaaaaa aaaaaaaa
```

Figure 27: Mus musculus transferrin receptor 2 amino acid sequence (NP_056614) (SEQ ID NO:22)

```
  1 meqrwgllrr vqqwsprpsq tiyrrvegpq lehleeedre egaelpaqfc pmelkgpehl
 61 gscpgrsipi pwaaagrkaa pylvlitlli ftgafllgyv afrgscqacg dsvlvvdedv
121 npedsgrttl ywsdlqamfl rflgegrmed tirltslrer vagsarmatl vqdildklsr
181 qkldhvwtdt hyvglqfpdp ahantlhwvd adgsvqeqlp ledpevycpy satgnatgkl
241 vyahygrsed lqdlkakgve lagslllvrv gitsfaqkva vaqdfgaqgv liypdpsdfs
301 qdphkpglss hqavyghvhl gtgdpytpgf psfnqtqfpp vessglpsip aqpisadiad
361 qllrkltgpv apqewkghls gspyrlgpgp dlrlvvnnhr vstpisnifa ciegfaepdh
421 yvvigaqrda wgpgaaksav gtaillelvr tfssmvsngf rprrsllfis wdggdfgsvg
481 atewlegyls vlhlkavvyv sldnsvlgdg kfhaktspll vslienilkq vdspnhsgqt
541 lyeqvalthp swdaeviqpl pmdssaysft afagvpavef sfmeddrvyp flhteedtye
601 nlhkmlrgrl pavvqavaql agqllirlsh dhllpldfgr ygdvvlrhig nlnefsgdlk
661 ergltlqwvy sargdyiraa eklrkeiyss ernderlmrm ynvrimrvef yflsqyvspa
721 dspfrhiflg qgdhtlgalv dhlrmlradg sgaassrlta glgfqesrfr rqlalltwtl
781 qgaanalsgd vwnidnnf
```

Figure 36
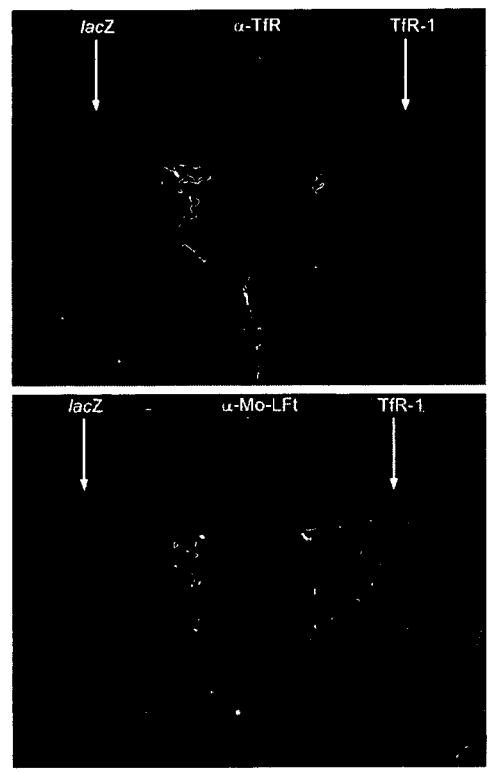

METHODS FOR MAGNETIC RESONANCE IMAGING

RELATED APPLICATIONS

This application is a continuation-in-part of U.S. patent application Ser. No. 10/384,496, filed Mar. 7, 2003, which claims the benefit of the filing date of U.S. Provisional Patent Application No. 60/363,163, filed on Mar. 7, 2002. The teachings of these applications are incorporated by reference herein.

BACKGROUND

Tools that enable one to visualize gene expression in vivo are of fundamental importance to the future of medicine and the biological sciences. The emerging field of genetic medicine requires non-invasive imaging methods that can indicate where, when and if therapeutic genes have been delivered and whether the desired protein has been expressed. In the realm of basic biological research, the ability to image the timing and location of gene expression in vivo is a fundamental need.

Scientists typically monitor gene expression by incorporating a marker gene that is expressed along with the gene of interest, often as either a transcriptional or translational fusion. Detection of the marker gene products is most often achieved using histological preparations (e.g. using a β-galactosidase assay), or by using fluorescence microscopy (e.g. using green fluorescent protein, or GFP). Neither of these methods permit non-invasive imaging of tissues or other macroscopic assemblies of cells. Markers that require histological preparation cannot be detected without sacrificing the subject material. Fluorescent markers can be imaged in living cells, but even with the most sophisticated optical technologies available, it is not possible to image at tissue depths exceeding approximately 500 μm. Other methods such as PET (positron emission tomography), gamma cameras, and SPECT (single-photon emission computed tomography) have been used to detect gene expression in vivo, but all of these suffer from limited spatial resolution, which is on the order of cubic millimeters or larger.

MRI is a widely used clinical diagnostic tool that allows non-invasive imaging of optically opaque subjects and provides contrast among soft tissues at high spatial resolution. In the majority of clinical applications, the MRI signal is derived from protons of the water molecules present in the materials being imaged. The image intensity of tissues is determined by a number of factors. The physical properties of a specific tissue, such as the proton density, spin lattice relaxation time (T1), and the spin-spin relaxation time (T2) often determine the amount of signal available.

A number of compositions termed "contrast agents" have been developed to provide enhanced contrast between different tissues. Contrast agents commonly affect T1, T2 or both. In general, contrast agents are made potent by incorporating metals with unpaired d or f electrons. For example, T1 contrast agents often include a lanthanide metal ion, usually $Gd^{3+}$, that is chelated to a low molecular-weight molecule in order to limit toxicity. T2-agents often consist of small particles of magnetite ($FeO$—$Fe_2O_3$) that are coated with dextran. Both types of agents interact with mobile water in tissue to produce contrast; the details of this microscopic interaction differ depending on the agent type.

Most widely used contrast agents are exogenous, meaning that the contrast agent is produced externally and then delivered to the tissue or cells to be imaged. Exogenous contrast agents are generally delivered through the vascular system, typically have a nonselective distribution, and are physiologically inert. The exogenous contrast agents are used to highlight anatomy with poor intrinsic contrast, as well as to visualize various pathologies that disrupt normal vascular flow or cause a break in the blood-brain-barrier. None of these agents cross cellular membranes easily and therefore the existing technology is difficult to adapt for the analysis of intracellular events.

A new generation of MRI contrast agents is required to adapt this powerful imaging technology to the needs of molecular medicine and biological research.

SUMMARY OF THE INVENTION

In certain aspects, the invention relates to contrast agents for magnetic resonance imaging that are synthesized in a subject material as directed by a nucleic acid sequence. The contrast agents are made potent by sequestering available metal atoms, typically iron atoms. In certain aspects, the nucleic acid sequence encodes a metal binding protein that acts, directly or indirectly, to impart a contrast effect on the cell in which it is produced. The invention further relates to methods of generating and employing the subject contrast agents.

In certain embodiments, the invention relates to methods of generating an image of a subject material by imaging a subject material comprising a plurality of cells wherein a subset of the cells contain an MRI-detectable amount of contrast protein. Preferably, the subject material has been manipulated, such as by introduction of a recombinant nucleic acid, so as to produce amounts of contrast protein in excess of that which is normally produced by the subject material. For example, the contrast protein may be recombinant protein expressed from a recombinant nucleic acid. As another example, the contrast protein may be produced by an endogenous gene, the expression of which is increased by exogenous manipulation. In preferred embodiments, the amount of contrast protein present in different cells is distinguishable, and optionally, cells comprising measurable amounts of contrast protein are distinguishable from cells or other components of the material that do not comprise the measurable amount of contrast protein.

In another embodiment, methods of the invention comprise detecting gene expression by imaging a cell comprising a recombinant nucleic acid encoding a contrast agent. Preferably, detection of the contrast protein by magnetic resonance imaging indicates that the nucleic acid encoding the contrast protein is and/or has been expressed. Optionally, the contrast agent is a protein, preferably a metal-binding protein. Exemplary classes of metal binding proteins include ferritin proteins; transferrin receptor proteins; iron regulatory proteins; iron scavenger proteins and the divalent metal transporter (DMT-1 or Nramp-2). Exemplary metal binding proteins of the invention include metal binding proteins that are at least 60%, optionally at least 70%, 80%, 90%, 95%, 99% or 100% identical to a sequence as shown in any of SEQ ID Nos: 2, 4, 6, 8, 10, 12, and 14. Alternatively, the protein is at least 60%, optionally at least 70%, 80%, 90%, 95%, 99% or 100% identical to a sequence as shown in any of SEQ ID Nos: 16, 18, 20 or 22. As shown herein, a combined expression of transferrin receptor with the light and heavy subunits of ferritin provides a particularly potent contrast signal.

Methods described herein may be used with essentially any material capable of generating the contrast agent in situ. For example, the subject material may be a cell, optionally a cell that is part of a cell culture, part of an in vitro tissue or part of a multicellular organism, such as, for example, a fungus, a plant, or an animal. In preferred embodiments, the subject material is a living mammal such as a mouse or a human.

In further aspects, the invention provides vectors for transfection of a multicellular organism comprising a recombinant nucleic acid encoding a contrast agent. In certain embodiments, the contrast agent is a metal-binding protein. Optionally, the vector is a viral vector derived from a virus selected from the group: an adenovirus, an adenovirus-associated virus, a herpes simplex virus, a retrovirus, an alphavirus, a poxvirus, an arena virus, a vaccinia virus, an influenza virus, a polio virus and a hybrid of any of the foregoing.

In additional aspects, the invention includes delivery systems for introducing nucleic acids of the invention into subject material. In certain embodiments, the invention provides viral particles suitable for transfecting a mammalian cell, comprising a nucleic acid comprising a coding sequence for a contrast agent, such as a contrast agent described above. Optionally, the viral particle is derived from one or more of the following: an adenovirus, an adenovirus-associated virus, a herpes simplex virus, a retrovirus, an alphavirus, a poxvirus, an arena virus, a vaccinia virus, an influenza virus and a polio virus. In additional embodiments, the invention provides colloidal suspensions suitable for transfecting a mammalian cell comprising a nucleic acid comprising a coding sequence for a contrast agent, such as a contrast agent described above. Optional types of colloidal suspensions include one or more of the following: a macromolecule complex, a nanocapsule, a microsphere, a bead, an oil-in-water emulsions, a micelle, a mixed micelle, and a liposomes.

In yet further aspects, the invention provides cells, cell cultures, organized cell cultures, tissues, organs and non-human organisms comprising a recombinant nucleic acid comprising a coding sequence for a contrast agent, such as a contrast agent described above. In certain embodiments, the organism is selected from the group consisting of: a mouse, a rat, a dog, a monkey, a pig, a fruit fly, a nematode worm and a fish, or alternatively a plant or fungus. In further embodiments, the cells, cell cultures, organized cell cultures, tissues, organs and non-human organisms may comprise a vector as described above.

In another aspect, the invention provides methods and compostions for screening or evaluating test compounds, such as, for example, candidate pharmaceutical compounds. Such methods may be employed in a cell-based or organism-based testing system. As a general concept, test compounds may elicit changes in the gene expression pattern of a cell or organism, and such changes may be monitored by use of contrast agents disclosed herein. Features of a test compound that may be of greatest interest may include, for example, effectiveness (e.g., therapeutic effectiveness in the case of a candidate pharmaceutical, lethality to target organism in the case of an herbicide or insecticide, and others characteristics of effectiveness depending on the intended use of the test compound), safety and toxicity. For each feature of interest, a contrast protein system may be designed to monitor expression of one or more informative genes. With respect to safety and toxicity in mammals or other organisms, one may monitor changes in gene expression of various factors involved in toxicity such as, for example, genes involved in drug metabolism, stress response, heat shock, cell cycle regulation, inflammation, apoptosis, DNA damage repair, or cell proliferation. Where a lead compound is known or expected to have certain undesirable side effects, the lead compound, as well as structurally related variants, may be tested in a cell or organism having a contrast agent system that provides information about the undesirable side effect, so as to identify lead compounds or variants thereof with reduced side effects. Combinations of test compounds may be similarly tested to identify combinations and doses thereof that provide desirable features. Levels of gene expression upon exposure to one or more test compounds or conditions may be monitored using MRI to determine any changes over time and/or spatial location of expression.

In still another aspect, the methods and compositions described herein may be used in association with a variety of applications in plants. For example, the contrast agents as described herein may be used to facilitate monitoring expression of transgenes introduced into plants for various commercial purposes. Additionally, the expression level of a variety of genes may be monitored upon exposure of a plant to environmental conditions or test compounds.

The practice of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

The claims provided below are hereby incorporated into this section by reference.

BRIEF DESCRIPTION OF THE DRAWINGS

FIG. 6. Human ferritin heavy chain cDNA sequence (BC016009) (SEQ ID NO:1). The coding region is underlined.

FIG. 7. Human ferritin heavy chain amino acid sequence (AAH16009) (SEQ ID NO:2).

FIG. 8. Human ferritin light chain cDNA sequence (XM_050469) (SEQ ID NO:3) The coding region is underlined.

FIG. 9. Human ferritin light chain amino acid sequence (XP_050469) (SEQ ID NO:4).

FIG. 10. *Mus musculus* ferritin heavy chain cDNA sequence (NM_010239.1) (SEQ ID NO:5). The coding region is underlined.

FIG. 11. *Mus musculus* ferritin heavy chain amino acid sequence (NP_034369.1) (SEQ ID NO:6).

FIG. 12. *Mus musculus* ferritin light chain 1 cDNA sequence (NM_010240.1) (SEQ ID NO:7). The coding region is underlined.

FIG. 13. *Mus musculus* ferritin light chain 1 amino acid sequence (NP_034370.1) (SEQ ID NO:8)

FIG. 14. *Mus musculus* ferritin light chain 2 cDNA sequence (NM_008049.1) (SEQ ID NO:9). The coding region is underlined.

FIG. 15. *Mus musculus* ferritin light chain 2 amino acid sequence (NP_032075.1) (SEQ ID NO:10)

FIG. 16. *Rattus norvegicus* ferritin subunit H cDNA sequence (NM_012848.1) (SEQ ID NO: 11). The coding region is underlined.

FIG. 17. *Rattus norvegicus* ferritin subunit H amino acid sequence (NP_036980.1) (SEQ ID NO:12)

FIG. 18. *Rattus norvegicus* ferritin light chain 1 cDNA sequence (NM_022500.1) (SEQ ID NO: 13). The coding region is underlined.

FIG. 19. *Rattus norvegicus* ferritin light chain 1 amino acid sequence (NP_071945.1) (SEQ ID NO:14).

FIG. 20. *Homo sapiens* transferrin receptor cDNA sequence (NM_003234) (SEQ ID NO: 15). The coding region is underlined.

FIG. 21. *Homo sapiens* transferrin receptor amino acid sequence (NP_003225) (SEQ ID NO:16).

FIG. 22. *Homo sapiens* transferrin receptor 2 cDNA sequence (NM_003227) (SEQ ID NO:17). The coding region is underlined.

FIG. 23. *Homo sapiens* transferrin receptor 2 amino acid sequence (NM_003218) (SEQ ID NO:18).

FIG. 24. *Mus musculus* transferrin receptor coding sequence (NM_011638) (SEQ ID NO:19).

FIG. 25. *Mus musculus* transferrin receptor amino acid sequence (NP_035768) (SEQ ID NO:20).

FIG. 26. *Mus musculus* transferrin receptor 2 nucleic acid sequence (NM_015799) (SEQ ID NO:21). The coding region is underlined.

FIG. 27. *Mus musculus* transferrin receptor 2 amino acid sequence (NP_056614) (SEQ ID NO:22).

FIG. 36. In vivo application of transferrin receptor-based MRI reporter in the brain.

DETAILED DESCRIPTION OF THE INVENTION

1. Definitions

Figure 1:
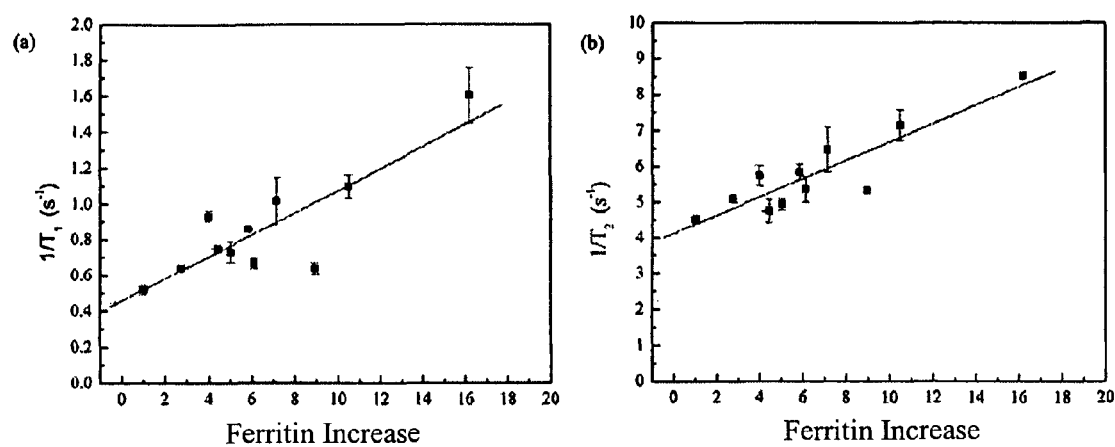
FIG. 1. Correlation between ferritin increase and $1/T_1$ (a) and $1/T_2$ (b) in simulated tumors. The solid line is least-squares fit through the data (guide for the eye). The values are normalized to give the ferritin increase over the mean baseline value of the control pellet, which is 1.5 mg/ml of ferritin; the experimental samples were incubated with various concentration of ferric ammonium citrate (FAC) and the control samples were incubated in the absence of FAC. The error bars represent the standard deviation for N=4 experimental runs.

"Coding sequence" is used herein to refer to the portion of a nucleic acid that encodes a particular protein. A coding region may be interrupted by introns and other non-coding sequences that are ultimately removed prior to translation.

"Colloidal suspension" is used herein to refer to a colloidal suspension that comprises one or more nucleic acids for delivery to cells. The material in a colloidal suspension is generally designed so as to protect nucleic acids and facilitate the delivery of nucleic acids across cell membranes. Exemplary colloidal suspensions include, but are not limited to, lipid micelles, tubes, rafts, sandwiches and other lipid structures, often comprising cationic lipids. Other colloidal suspensions include nanocapsules, microbeads and small, nucleic acid-binding polymeric structures, etc.

The term "contrast agent" is used herein to refer to a molecule that generates a contrasting effect in vivo, whether the effect is direct or indirect or both. In exemplary embodiments, "contrast agent" is used interchangeably with "contrast protein" or "contrast polypeptide." In the case of a direct effector, the contrast protein will typically form a complex that affects the relaxation times T1, T2 or T2*. Often direct contrast proteins form metalloprotein complexes. Exemplary categories of contrast proteins include, for example, metal binding proteins and/or agents that stimulate production of one or more metal-binding proteins, etc. Indirect effectors include molecules that cause a cell to produce a direct contrast protein and/or modulate a functional, biochemical, and/or biophysical characteristic of a direct contrast protein, thereby creating a contrast effect. Exemplary categories of indirect effectors include, for example, proteins and/or nucleic acids that affect expression of a direct contrast protein, modulate the activity of a direct contrast protein, modulate metal binding to a metal-binding protein, modulate expression of an iron regulatory protein, and/or modulate the activity of an iron regulatory protein, etc.

The term "contrast effect", as used herein with respect to MRI, includes any alteration in the MRI signal that renders one cell or tissue detectably different from another. A contrast effect may involve effects on T1, T2 and/or T2*. In MRI, a subject containing mobile water is generally placed in a large static magnetic field. The field tends to align some of the magnetic moments (spins) of the hydrogen nuclei in the water along the field direction. The spin lattice relaxation time (T1) is the time constant for a population of nuclei placed in a magnetic field to equilibrate along the magnetic field direction. T1 is the time constant for the transfer of energy from the spin system to the environment (the lattice). The spin-spin relaxation time (T2) is the time constant for nuclei precessing at the Larmor frequency to remain in phase with each other. Alternatively, T2 is called the spin-phase memory time. This loss of phase coherence is attributed to low-frequency fluctuations of the magnetic field that are commonly due to interactions among spins. The relaxation time T2* is defined as $1/T2^* = 1/T2 + \gamma \Delta B$, where $\gamma$ is the nuclear gyromagnetic ratio and $\Delta B$ is the static external magnetic field inhomogeneity.

The terms "contrast gene" or "contrast nucleic acid" are used interchangeably herein to refer to a nucleic acid comprising a coding sequence for a contrast protein.

An "externally regulated promoter" is a nucleic acid that affects transcription in response to conditions that may be provided in a controlled manner by one of skill in the art. Externally regulated promoters may be regulated by specific chemicals, such as tetracycline or IPTG, or by other conditions such as temperature, pH, oxidation state etc. that are readily controlled external to the site of transcription.

The term "Ferritin protein" is intended to include any of a group of diiron-carboxylate proteins characterized by the tendency to form a multimeric structure with bound iron and having a helix-bundle structure comprising an iron-coordinating Glu residue in a first helix and a Glu-X-X-His motif in a second. Certain ferritins maintain bound iron in a primarily Fe(III) state. Bacterioferritins tend to be haem proteins. Vertebrate ferritins tend to be assembled from two or more subunits, and mammalian ferritins are often assembled from a heavy chain and a light chain. Many ferritins form hollow structures with an iron-rich aggregate in the interior. Exemplary ferritins are presented in Table 2 below.

"Homology" or "identity" or "similarity" refers to sequence similarity between two polypeptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present invention.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) J Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used. See http://www.ncbi.nlm.nih.gov.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990).

The term "iron binding protein" as used herein is intended to include proteins that bind to iron under physiologically relevant conditions. Certain iron binding proteins interact with iron through a cofactor such as heme. Many other exemplary cofactors are also described herein. Other iron binding proteins form an iron binding site with the appropriate amino acids, including but not limited to, histidine, aspartate, glutamate, asparagine and glutamine. Although iron binding proteins of the invention bind iron, they are also likely to bind to other metals. Accordingly, "iron binding protein" as used herein is not meant to indicate that the protein binds iron exclusively, or even that the protein binds iron more tightly than other metals.

An "iron regulatory protein" refers to a protein that is involved in iron utilization, processing, and/or accumulation in a cell. Iron regulatory proteins include, for example, proteins that regulate iron homeostasis, proteins that regulate iron trafficking into or out of a cell, proteins involved in regulating the production of iron related elements, such as, for example, ferritin and transferring, etc. Iron regulatory proteins may or may not bind iron directly.

The terms "modulation" or "modulates", when used in reference to expression of a polypeptide, refers to the capacity to either up regulate gene expression (e.g., increase expression by activation or stimulation) or down regulate gene expression (e.g., decrease expression by inhibition or suppression).

As used herein, the term "nucleic acid" refers to polynucleotides such as deoxyribonucleic acid (DNA), and, where appropriate, ribonucleic acid (RNA). The term should also be understood to include analogs of either RNA or DNA made from nucleotide analogs (including analogs with respect to the base and/or the backbone, for example, peptide nucleic acids, locked nucleic acids, mannitol nucleic acids etc.), and, as applicable to the embodiment being described, single-stranded (such as sense or antisense), double-stranded or higher order polynucleotides.

The term "operably linked" is used herein to refer to the relationship between a regulatory sequence and a gene. If the regulatory sequence is positioned relative to the gene such that the regulatory sequence is able to exert a measurable effect on the amount of gene product produced, then the regulatory sequence is operably linked to the gene.

The term "plant" refers to whole plants, plant organs (e.g., leaves, stems, roots, etc.), seeds and plant cells and progeny of the same. The term "plant cell" is meant to encompass seeds, suspension cultures, embryos, meristematic regions, callus tissue, leaves, roots, shoots, gametophytes, sporophytes, pollen, and microspores. Both monocotyledonous and dicotyledonous plants may used in accordance with the compositions and methods described herein.

The term "plant expression cassette" refers to DNA constructs that are capable of resulting in the expression of a protein from an open reading frame in a plant cell. Expression cassettes typically contain a promoter and a coding sequence. Expression cassettes may optionally also contain one or more of the following sequences: (i) a 3' untranslated region or (ii) a 'signal sequence' or 'leader sequence' to facilitate co-translational or post-translational transport of a peptide to certain intracellular structures such as the chloroplast (or other plastid), endoplasmic reticulum, or Golgi apparatus.

The term "plant transformation vector" refers to DNA constructs that are capable of efficient transformation of a plant cell. Such constructs may consist of one or more plant expression cassettes, and may be organized into more than one 'vector' DNA molecule. For example, binary vectors are plant transformation vectors that utilize two non-contiguous DNA vectors to encode all requisite cis- and trans-acting functions for transformation of plant cells (Hellens and Mullineaux (2000) Trends in Plant Science 5:446-451).

A "polylinker" is a nucleic acid comprising at least two, and preferably three, four or more restriction sites for cleavage by one or more restriction enzymes. The restriction sites may be overlapping. Each restriction sites is preferably five, six, seven, eight or more nucleotides in length.

A "recombinant helper nucleic acid" or more simply "helper nucleic acid" is a nucleic acid which encodes functional components that allow a second nucleic acid to be encapsidated in a capsid. Typically, in the context of the present invention, the helper plasmid, or other nucleic acid, encodes viral functions and structural proteins which allow a recombinant viral vector to be encapsidated into a capsid. In one preferred embodiment, a recombinant adeno-associated virus (AAV) helper nucleic acid is a plasmid encoding AAV polypeptides, and lacking the AAV ITR regions. For example, in one embodiment, the helper plasmid encodes the AAV genome, with the exception of the AAV ITR regions, which are replaced with adenovirus ITR sequences. This permits replication and encapsidation of the AAV replication defective recombinant vector, while preventing generation of wild-type AAV virus, e.g., by recombination.

A "regulatory nucleic acid" or "regulatory sequence" includes any nucleic acid that can exert an effect on the transcription of an operably linked open reading frame. A regulatory nucleic acid may be a core promoter, an enhancer or repressor element, a complete transcriptional regulatory region or a functional portion of any of the preceding. Mutant versions of the preceding may also be considered regulatory nucleic acids.

The term "small molecule" refers to a compound, which has a molecular weight of less than about 5 kD, less than about 2.5 kD, less than about 1.5 kD, or less than about 0.9 kD. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened using any of the methods described herein. The term "small organic molecule" refers to a small molecule that is often identified as being an organic or medicinal compound, and does not include molecules that are exclusively nucleic acids, peptides or polypeptides.

The term "test compound" refers to a molecule to be tested by one or more screening method(s) as a putative modulator of gene expression. The term "control test compound" refers to a compound having a known effect on gene expression from a given nucleic acid construct. For example, a control test compound may activate gene expression from a given promoter, inhibit gene expression from a given promoter, or have no effect on gene expression from a given promoter. In certain embodiments, various predetermined concentrations of test compounds are used for screening such as 0.01 µM, 0.1 µM, 1.0 µM and 10.0 µM. Examples of test compounds include, but are not limited to, peptides, nucleic acids, carbohydrates, and small molecules.

The term "toxicity marker gene promoter" refers to the upstream regulatory region of a gene that exhibits a modulation in expression upon exposure of a cell or organism to an environmental stress and/or toxic substance. Examples of toxicity marker genes include, for example, genes that encode proteins involved in drug metabolism (e.g., CYP450s, acyltransferases, sulfotransferases, etc.), growth factors and receptors (e.g., IGFs, interleukins, NGFs, TGFs, VEGF, etc.), kinases and phosphatases (e.g., lipid kinases, MAPKs, stress-activated kinases, etc.), nuclear receptors (e.g., retinoic acid, retinoid X, PPARs, etc.), transcription factors (e.g., oncogenes, stats, NF-kappa B, zinc-finger proteins, etc.), DNA damage repair proteins (e.g., polymerases, topoisomerases, GADDs, RAG, etc.), apoptosis proteins (e.g., BCL-2 family, Bad, Bax, Caspases, Fas, etc.), stress response proteins (e.g., drug transporters, heat shock proteins, etc.), membrane proteins (e.g., gap-junction proteins, Na+/K+-ATPase, selectins, etc.), cell-cycle regulators (e.g., cyclins and associated proteins), and proteins involved in inflammation (e.g., chemokines, cytokines, chemokine receptors, cytokine receptors, interleukins, interleukin receptors, TNF ligands, TNF ligand receptors, etc.). Specific examples of mouse and human genes for the various functional categories listed above are shown in Table 1. The nucleotide sequences for the genes shown in Table 1 and their regulatory regions may be found in publicly available databases, such as, for example, GenBank (world wide web at ncbi.nlm.nih.gov). A "toxic substance" is meant to include a substance, or amount thereof, that is considered unsafe for administration to an organism. For example, a toxic substance includes any substance that would not be approved by the FDA for clinical administration to a human for reasons of safety and/or toxicity.

A "transcriptional fusion" is a nucleic acid construct that causes the expression of an mRNA comprising at least two coding regions. In other words, two or more open reading frames may be organized into a transcriptional fusion such that both open reading frames will be expressed as part of a single mRNA and then give rise, as specified by the host cell, to separate polypeptides. The open reading frames in a transcriptional fusion tend to be subject to the same transcriptional regulation, but the encoded polypeptides may be subject to distinct post-translational fates (eg. degradation, etc.). A "transcriptional fusion" may be contrasted with a "translational fusion" in which two or more open reading frames are connected so as to give rise to a single polypeptide. The fused polypeptides in a "translational fusion" tend to experience similar transcriptional, translational and post-translational regulation.

As used herein, the term "transfection" means the introduction of a nucleic acid, e.g., an expression vector, into a recipient cell, and is intended to include commonly used terms such as "infect" with respect to a virus or viral vector. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

The terms "transformed plant" or "modified plant" refer to plants comprising plant cells that contain an exogenous DNA construct, such as, for example, a coding sequence for a contrast protein. The term includes, but is not limited to, plants produced by nuclear transformation, i.e., where the transformed gene is expressed from the nuclear genome (transgenic plants), and plants produced by plastid transformation, i.e., where the transformed gene is expressed from the plastid genome (transplastomic plants). Transformed plants include plant seedlings and plant progeny that are produced via sexual or asexual reproduction.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, partly or entirely heterologous, i.e., foreign, to the transgenic animal or cell into which it is introduced. Optionally, a transgene-encoded polypeptide may be homologous to an endogenous gene of the transgenic animal or cell into which it is introduced, but may be designed to be inserted, or is inserted, into the genome in such a way as to alter the genome of the cell into which it is inserted (e.g., it is inserted at a location which differs from that of the natural gene). Alternatively, a transgene can also be present in an episome. A transgene can include one or more transcriptional regulatory sequences and any other nucleic acid, (e.g. intron), that may be necessary for optimal expression of a selected coding sequence. A transgene may also contain no polypeptide coding region, but in such cases will generally direct expression of a functionally active RNA, such as an rRNA, tRNA, ribozyme, etc. A "therapeutic transgene" is a transgene that is introduced into a cell, tissue and/or organism for the purpose of altering a biological function in a manner that is beneficial to a subject.

"Transient transfection" refers to cases where exogenous nucleic acid is retained for a relatively short period of time, often when the nucleic acid does not integrate into the genome of a transfected cell, e.g., where episomal DNA is transcribed into mRNA and translated into protein. A cell has been "stably transfected" with a nucleic acid construct comprising viral coding regions when the nucleic acid construct has been introduced inside the cell membrane and the viral coding regions are capable of being inherited by daughter cells.

"Viral particle" is an assemblage of at least one nucleic acid and a coat comprising at least one viral protein. In general, viral particles for use in delivering nucleic acids to cells will retain the ability to insert the nucleic acid into a cell, but may be defective for many other functions, such as self-replication.

2. Exemplary Methods

In some aspects, the invention relates to methods for performing MRI using an intracellular contrast agent that is generated in situ via genetic instructions and made potent by the sequestering of metal atoms. The sequestered metal atoms are preferably endogenous metal atoms such as, for example, iron atoms. In certain embodiments, methods of the invention comprise contacting subject material with a nucleic acid encoding instructions for the synthesis of an intracellular contrast agent, such as a metal binding protein. In such an embodiment, upon internalization by an appropriate cell, the nucleic acid directs production of the metal binding protein which becomes potent as a contrast agent by binding to available metal atoms. In another embodiment, the methods of the invention comprise contacting subject material with a protein or nucleic acid that indirectly affects contrast, for example, by increasing the amount of metal in the cell or by affecting the expression and/or activity of a metal binding protein. Intracellular contrast agents described herein may be employed in the imaging of essentially any biological material that is capable of producing such an agent, including but not limited to: cultured cells, tissues, and living organisms ranging from unicellular organisms to multicellular organisms (e.g. humans, non-human mammals, other vertebrates, higher plants, insects, nematodes, fungi etc.). While most biological systems contain a variety of metals that have potent contrast effects, it is understood that iron is generally the only such metal that is sufficiently concentrated to be useful in rendering an intracellular contrast agent potent. However, if desired, material to be imaged may be supplemented with exogenous metal atoms, and such protocols will preferably be optimized to reduce deleterious effects caused by the exogenous metal atoms.

In certain embodiments, the novel contrast technology described herein may be employed to investigate the regulation of gene expression in situ. For example, a nucleic acid encoding a contrast protein may be introduced into a cell, tissue, and/or subject of interest. Those cells having appropriate intracellular conditions for expression of the contrast protein may be distinguished by MRI from cells that do not produce the contrast protein. In certain embodiments, the nucleic acid encoding the contrast protein is operably linked to a constitutively active regulatory sequence. In further embodiments, the contrast protein is operably linked to a regulatory sequence so that production of the contrast protein may be regulated by application of one or more exogenously controlled conditions, such as temperature changes, concentration of an inducer or repressor, etc. In yet another embodiment, the activity of the regulatory sequence is at least partially unknown. In a further embodiment, the nucleic acid encoding a contrast protein is not operably linked to a regulatory sequence (or is operably linked to a weak promoter). This type of "promoterless" construct may be used to identify endogenous sequences that supply regulatory activity in a manner analogous to an "enhancer trap".

In certain exemplary embodiments, methods and compositions of the invention are used to monitor the expression of a transgene of interest, such as a therapeutic transgene. Subject material is contacted with both a transgene of interest, such as a therapeutic transgene, and a nucleic acid construct comprising the coding sequence for a contrast protein that is operably linked to a regulatory sequence. In one variation, production of the transgene of interest and production of the contrast protein are both modulated by functionally similar (optionally identical) regulatory sequences. For example, if subject material has been contacted with a transgene under direction of a strong constitutive promoter, such as certain viral terminal repeat promoters, then expression of the gene encoding the contrast protein should also be under direction of the same promoter or a promoter designed to have a similar expression pattern. In some variations, the transgene of interest is introduced first, and then at a later time the nucleic acid encoding the contrast protein is introduced. In other variations, the nucleic acid encoding the contrast protein is introduced at the same time as the transgene of interest, and optionally the contrast nucleic acid and the transgene of interest are located on the same vector. In certain embodiments, the contrast nucleic acid is expressed as a transcriptional fusion with the transgene of interest. In further embodiments, the contrast gene and the transgene of interest (or a second copy thereof) may be expressed as a fusion protein. The fusion protein approach may be desirable where it is thought that the effectiveness of the therapeutic transgene is influenced by post-transcriptional regulation. Subject material may be imaged by MRI, and cells having the contrast protein may be detected and distinguished from cells that do not have the contrast protein. In preferred embodiments, the level of contrast detected by MRI will correlate with, or be indicative of, the level of expression of the transgene of interest.

In further exemplary embodiments, methods and compositions of the invention may be used to investigate the in situ regulatory activity of a regulatory sequence of interest. Subject material is contacted with a nucleic acid encoding a contrast protein, where the nucleic acid is operably linked to the regulatory sequence of interest. Once internalized within an appropriate cell, the contrast gene is expressed at a level that is regulated by the regulatory sequence of interest. In preferred embodiments, the level of contrast detected by MRI will be correlated with the level of activity of the regulatory sequence of interest. The regulatory sequence of interest may be essentially any regulatory sequence, including but not limited to a promoter, an enhancer, an entire promoter/enhancer region, a mutated or altered form of the preceding, or one or more portions of the preceding.

In further exemplary embodiments, the methods described herein may be used to determine whether a physiologically important regulatory sequence is active in situ. For example, the p53 protein is a widely recognized regulator of cell proliferation and apoptosis that exerts its regulatory influences partly in response to DNA damage. Therefore, a construct comprising a p53-responsive regulatory sequence operably linked to a nucleic acid encoding a contrast protein would permit detection of cells, in situ, in which the p53 regulatory pathway has been activated. Similarly, methods of the invention may be employed to investigate, for example, the status of pro-proliferative signaling pathways (e.g. to identify cancerous or pre-cancerous cells), or to assess the status of inflammatory pathways (e.g. in host and/or donor tissues in or near transplanted organs), or to non-invasively image promoter activation during the course of development, etc. In view of this disclosure, one of skill in the art will be able to develop myriad related methods.

An analogy may be drawn between the traditional reporter gene assays routinely performed by biologists, such as assays employing β-galactosidase (β-Gal) or green fluorescent protein (GFP), and certain embodiments of the present invention. Accordingly, certain methods of the invention may be used as an alternative for other commonly used cell-screening methods. For example, a method for assessing candidate pharmaceuticals may traditionally involve contacting the candidate pharmaceutical with a cell carrying an informative reporter gene construct. Now, the standard reporter gene may be replaced with a contrast gene, and the standard detection system may be replaced with an MRI system. While certain embodiments of the present invention may be used to substitute for traditional reporter gene assays, these traditional assays are far more limited in their utility. For example, traditional assays use optically-based readout technologies that are ineffective in visualizing gene expression deep within intact tissue, and often require histological processing of the biological materials. By contrast, certain embodiments of the present invention employ an MRI contrast agent as a reporter gene, allowing signal readout deep within optically opaque tissues by MRI and, if desired, readouts may be obtained with little or no disruption of the biological function of the subject material.

In another embodiment, methods for evaluating the safety and/or toxicity of a test compound are provided. Gene expression analysis applied to toxicology studies, also referred to as toxicogenomics, is rapidly being embraced by the pharmaceutical industry as a useful tool to identify safer drugs in a quicker, more cost-effective manner. Studies have demonstrated the utility of applying gene expression profiling towards drug safety evaluation, both for identifying mechanisms underlying toxicity, as well as for providing a means to identify safety liabilities early in the drug discovery process. Toxicogenomics has the potential to better identify and assess adverse drug reactions of new drug candidates or marketed products in humans. Hepatotoxicity and nephrotoxicity are often of greatest concern, however risks associated with other tissue toxicities and with mutagenic toxicity are also of interest. Particularly in the liver, toxicogenomic studies have focused on the expression of toxicity marker genes associated with AhR-, PXR- and PPAR-signaling, as well as the Phase I, Phase II and Phase III drug metabolizing enzymes, including nearly all of the major cytochrome p450 isozymes. The contrast agents disclosed herein may be used in toxicogenomic studies, and, because the detection methodology is non-invasive, the contrast agents will allow time series of gene expression in a single animal. For example, a cell comprising a nucleic acid construct comprising a toxicity marker gene operably linked to a coding region for a contrast protein may be contacted with a test compound. The effect of the test compound on the level of expression from the toxicity marker gene promoter may then be determined using MRI. The level of contrast detected by MRI will correlate with, or be indicative of, the level of expression from the toxicity marker gene promoter. Any change in the level of gene expression in the presence of the test compound will indicate that the test compound may have a toxic effect on the cell. In certain embodiments, an increase in the level of expression of the contrast protein may be indicative of toxicity (e.g., when the contrast protein is operably linked to a promoter from a gene known to show an increase in expression in response to contact with a toxic substance) or, alternatively, a decrease in the level of expression of the contrast protein may be indicative of toxicity (e.g., when the contrast protein is operably linked to a promoter from a gene known to show a decrease in expression in response to contact with a toxic substance). This method may be used to evaluate test compounds that directly or indirectly (e.g., the test compound modulates the level of expression and/or activity of a protein that effects transcription from the toxicity marker gene promoter) effect expression from the toxicity marker gene promoter. In an exemplary embodiment, the level of toxicity of a test compound is evaluated in a non-human multicellular organism, such as, for example, a mouse, rat, dog, monkey, pig, fruit fly, nematode worm, or fish. Such organisms may be transgenic (e.g., wherein the germline of the organism has been modified to contain a nucleic acid construct comprising a toxicity marker gene promoter operably linked to the coding sequence for a contrast protein) or may contain a subset of cells that have been transfected with a nucleic acid construction comprising a toxicity marker gene promoter operably linked to the coding sequence for a contrast protein (such as, for example, using a viral vector, etc.). When testing toxicity in an organism it may be useful to evaluate any changes in expression from the toxicity marker gene promoter throughout the entire organism, in one or more specific locations within the organism (e.g., a specific tissue or organ, such as, for example, the kidney or liver), over time in one or more locations, etc. In an exemplary embodiment, a transgenic animal containing a nucleic acid construct comprising one or more toxicity marker gene promoters operably linked to the coding sequence for a contrast protein is contacted with a candidate pharmaceutical compound for purposes of pre-clinical evaluation of the safety and/or toxicity of the candidate compound. In certain embodiments, it may be useful to screen the candidate compound against a panel of transgenic animals each containing a coding sequence for a contrast agent operably linked to a different toxicity marker gene promoter. In another embodiment, a single transgenic animal may contain multiple contrast agent reporter constructs (e.g., a coding sequence for a contrast protein operably linked to a variety of toxicity marker gene promoters). In such an embodiment, further screening, for example, using western blots or northern blots, may be used to further evaluate the toxicity marker (e.g., each construct may contain a unique tag for identification of the specific construct that exhibited a change in expression upon exposure to the test compound). Alternatively, expression of the various transgene constructs could be targeted to different specified locations within the animal using the techniques described further herein. In this manner, expression of different toxicity genes could be determined in the same animal based on determination of the location of the transgene expression by MRI imaging.

A large number of marker genes for toxicity have been identified, and regulatory elements of virtually any of such genes may be operably linked to a gene encoding a contrast protein to generate a toxicity-responsive contrast gene. Examples of toxicity marker genes are provided in Table 1, and additional toxicity marker genes will, upon review of this specification, be apparent to those practicing in the field.

TABLE 1

Toxicity Marker Genes

| Function | Mouse | Human |
|---|---|---|
| Induction of apoptosis | Atm, Bax, Gpx1, Il18, Mlh1, Myc, Tnf | BAX, CASP10, CDKN1A, IL18, LTA, TNFSF10, TNFSF6, TP53, TRADD |
| Anti-apoptosis | Bcl2, Bcl2l1, Hspa1a, Prdx2 | AKT1, BAG1, BCL2, BCL2L1, BCL2L2, IGF1R, IL1A, NFKB1, TNF |
| Regulation of apoptosis | Bcl2l2, Brca1, Casp1, Casp8, Ddit3, Mgmt | |
| Other apoptosis genes | Ahr, Akt1, Bag1, Dnaja3, E2f1, Gadd45b, Nfkb1, Tnfrsf1a, Tnfsf10, Tnfsf6, Trp53 | AHR, BRCA1, CASP1, CASP8, CLU, DNAJA3, E2F1, GADD45A, GADD45B, IL1B, NFKBIA, TNFRSF1A |
| Cell cycle arrest & checkpoint | Cdkn1a, Cdkn1b, Cdkn2a, Ddit3, Gadd45a, Msh2 | BRCA1, CDKN1A, CDKN1B, CDKN2A, CDKN2D, DDIT3, GADD45A, MYC, RB1, TP53 |
| Negative regulation of cell cycle | Apc, Atm, Brca1, Cdkn2d, Trp53 | APC, ATM, BAX, BRCA1, CDKN2A, CDKN2D, MLH1, MSH2, RB1, TP53 |
| Regulation of cell cycle | Abl1, Bcr, Brca2, Ccnd1, Ccne1, Cdk4, E2f1, Fgf2, Gadd45b, Il1a, Il1b, Mdm2 | |
| Other cell cycle genes | Ahr, Ccnc, Ccng1, Cdk2, Chek2, Cryaa, Itgb1, Mlh1, Pcna, Rad51 | ABL1, AHR, BCL2, BRCA2, CCNC, CCND1, CCNE1, CCNG1, CCT2, CCT4, CCT7, CDK2, CDK4, CHEK2, DNAJA2, E2F1, FGF2, IGF1R, IL1A, IL1B, PCNA, RB1 |
| Chemokines & cytokines | Ccl3, Ccl4, Csf2, Cxcl10, Gdf15, Il18, Il1a, Il1b, Il6, Lta, Mif, Tnf, Tnfsf10, Tnfsf6 | CCL21, CCL3, CCL4, CSF2, CXCL10, GDF15, IL18, IL1A, IL1B, IL6, LTA, MIF, TNF, TNFSF10, TNFSF6 |
| Growth factors and receptors | Ahr, Ar, Arnt, Egfr, Erbb2, Erbb3, Erbb4, Esr1, Esr2, Fgf2, Igf1r, Igf2r, Met, Tnfrsf11a, Tnfrsf1a | EGFR, ERBB2, ERBB3, ERBB4, FGF2, IGF1R, IGF2R, MET |
| Genes negatively regulating cell growth and proliferation | | BCL2, CDKN1A, CDKN1B, CDKN2A, CDKN2D, ESR2, IGFBP6, IL1A, IL1B, IL6, MDM2, MT3 |
| Genes positively regulating cell growth and proliferation | | CDK2, CXCL10, DNAJA2, FGF2, IGF1R, IL18, IL6, NOS2A, TNFRSF11A |
| Other genes involved in growth/ proliferation | Abl1, Brca1, Cdk4, Cdkn1a, Cdkn1b, Fos, Mdm2, Mt3, Myc, Nfkbia, Ppard, Trp53 | ABL1, AR, BCR, BRCA1, CCND1, CDK4, DDIT3, E2F1, ESR1, FOS, IGFBP6, MYC, NFKB2, PCNA, PRDX1, RARA, RARB, TOP1 |
| Drug related Transporters | Abcb1b, Abcb4, Abcc1, Abcc2, Abcc3, Abcc5, Abcc6, Abcg2, Ap1s1, Crabp1, Crat, Dpyd, Egfr, Grp58, Igf2r, Mt3, Nos2, Nr1i3, Por, Rad50, Xdh | ABCB1, ABCB4, ABCC1, ABCC2, ABCC3, ABCC5, ABCC6, ABCG2, AP1S1, AR, CRABP1, IGF2R, RAD50, TPMT |
| Cell adhesion molecules | Calr, Canx, Chst4, Itga6, Itga7, Itgae, Itgb1, Itgb2, Itgb5 | |

TABLE 1-continued

Toxicity Marker Genes

| Function | Mouse | Human |
|---|---|---|
| Chaperones & heat shock proteins | Bag1, Calr, Canx, Ccl3, Ccl4, Cct2, Cct3, Cct4, Cct5, Cct7, Cct8, Cxcl10, Dnaja1, Dnaja2, Dnaja3, Dnaja4, Dnajb1, Dnajb10, Dnajb11, Dnajb4, Dnajb5, Dnajb6, Dnajb9, Dnajc4, Dnajc5, Hspa1a, Hspa8, Hspa9a, Hspca, Hspcb, Hspd1, Hspe1, Serpinh1, St13, Tcp1, Tra1 | BAG1, CALR, CANX, CCT2, CCT3, CCT4, CCT5, CCT7, CCT8, CRYAA, CRYAB, DNAJA1, DNAJA2, DNAJA3, DNAJA4, DNAJB1, DNAJB11, DNAJB2, DNAJB4, DNAJB5, DNAJB9, DNAJC4, DNAJC5, DNAJC7, DNAJC8, HSF1, HSPA1A, HSPA1L, HSPA2, HSPA4, HSPA6, HSPA8, HSPA9B, HSPB1, HSPB2, HSPB3, HSPCA, HSPCB, HSPD1, HSPE1, HSPH1, HYOU1, SERPINH1, ST13, TCP1, TRA1 |
| Response to stress | DNA repair genes: Atm, Brca1, Brca2, Ercc1, Ercc3, Mgmt, Mlh1, Msh2, Rad23a, Rad50, Rad51, Srd5a2, Ung, Xpa, Xpc, Xrcc1, Xrcc2 | Response to drug: ABCB1, ABCB4, ABCC1, ABCC6, ABCG2, CTPS, MVP, NAT8; Response to DNA damage stimulus: ATM, BRCA1, CHEK2, DDIT3, GADD45A, RAD23A, XRCC; Response to oxidative stress: CAT, GPX1, GPX2, NUDT1, PRDX2, SOD1, SOD2; Response to other stresses: AHR, AKT1, CCL4, CES1, DNAJB4, DNAJB5, EPHX1, EPHX2, ERCC1, GADD45B, GSR, GSTA3, GSTA4, GSTT1, HIF1A, HSPB2, HYOU1, MT1X, MT3, NFKB1, NFKBIA, NQO1, PON3, PPARG, PPARGC1A, RAD51, SERPINH1, TNF, TRA1 |
| Transcription factors/regulators | Nuclear receptors: Ahr, Ar, Esr1, Esr2, Nr1i2, Nr1i3, Ppard, Pparg, Rara, Rarb, Rarg, Rxra, Rxrb, Rxrg; Other: Arnt, Brca1, Brca2, Ccnc, Cdk2, Cdk4, Cdkn2a, Ddit3, E2f1, Egr1, Elk1, Ercc3, Fos, Hif1a, Hod, Hsf1, Myc, Myst2, Myst4, Nfkb1, Nfkb2, Ppargc1a, Relb, Trp53 | Ligand dependent nuclear receptors: AHR, ESR1, ESR2, NR1I2, NR1I3, PPARD, PPARG, PPARGC1A, RARA, RARB, RARG, RXRA, RXRB, RXRG; Other: ABL1, AR, ARNT, BRCA1, BRCA2, CALR, CCNC, DDIT3, E2F1, EGR1, ELK1, ERCC3, FOS, HIF1A, HOP, HSF1, MYC, MYST2, MYST4, NFKB1, NFKB2, NFKBIA, NFKBIB, RB1, RELB, SAFB, TNF, TP53 |
| Acyltransferases | Acat1, Chat, Cml3, Crat, Dlat, Myst4, Nat1, Nat2, Nat5 | ACAT1, CHAT, CRAT, DLAT, HAT1, NAT1, NAT2, NAT5 |
| Methyltransferases | Comt, Hnmt, Mgmt, Nnmt, Srd5a2, Tpmt, Tyms | COMT, HNMT, MGMT, NNMT, TPMT, TYMS |
| Sulfotransferases | Chst1, Chst10, Chst2, Chst3, Chst4, Chst5, Chst7, Chst8, Gal3st1, Sult1a1, Sult1a2, Sult1b1, Sult1c1, Sult1e1, Sult2a2, Sult2b1, Sult4a1, Tpst1, Tpst2 | CHST1, CHST10, CHST2, CHST3, CHST4, CHST5, CHST6, CHST7, CHST8, GAL3ST1, SULT1A1, SULT1B1, SULT1C1, SULT1C2, SULT1E1, SULT2A1, SULT2B1, SULT4A1, TPST1, TPST2 |
| Isomerase | Grp58, Lta4h, Mif, Tbxas1, Top1, Top2a, Top2b | |
| Oxidoreductases | Acadsb, Cat, Cyp11a1, Cyp1a1, Cyp1a2, Cyp1b1, Cyp20a1, Cyp24a1, Cyp2a12, Cyp2a4, Cyp2c29, Cyp2c38, Cyp2c40, Cyp2c65, Cyp2c70, Cyp2d13, Cyp2d22, Cyp2e1, Cyp2f2, Cyp4a12, Cyp4b1, Cyp4f18, Cyp7a1, Cyp7b1, Cyp8b1, Dhfr, Dia1, Dpyd, Fmo1, Fmo4, Fmo5, Gpx1, Gpx2, Gsr, Hmox1, Hmox2, Nos2, Nqo1, Por, Prdx1, Prdx2, Ptgs1, Ptgs2, Sod1, Sod2, Srd5a2, Tbxas1, Xdh | ACADSB, CAT, CYP11A1, CYP11B2, CYP1A1, CYP1A2, CYP1B1, CYP20A1, CYP24A1, CYP26B1, CYP2A6, CYP2B6, CYP2C8, CYP2C9, CYP2D6, CYP2E1, CYP2F1, CYP3A4, CYP3A5, CYP4A11, CYP4B1, CYP4F3, CYP7A1, CYP7B1, CYP8B1, DHFR, DIA1, DPYD, FMO1, FMO4, FMO5, GPX1, GPX2, GSR, HMOX1, HMOX2, MAOA, MAOB, NOS2A, NQO1, POR, PRDX1, PRDX2, PTGS1, PTGS2, SOD1, SOD2, SRD5A2, TBXAS1, XDH |
| Glutathione peroxidases | Gpx1, Gpx2, Gsta2, Gsta3, Gsta4, Gstm1, Gstm2, Gstm3, Gstm5, Gsto1, Gstp2, Gstt1, Gstt2, Mgst1 | GPX1, GPX2, GSTA3, GSTA4, GSTM1, GSTM2, GSTM3, GSTM5, GSTO1, GSTP1, GSTT1, GSTT2, MGST1, MGST2, MGST3 |

TABLE 1-continued

Toxicity Marker Genes

| Function | Mouse | Human |
|---|---|---|
| Other Drug Metabolizing enzymes | Bche, Blmh, Ces1, Ctps, Cyp26b1, Ephx1, Ephx2, Hat1, Hspa5, Hyou1, Maoa, Mgst3, Mvp, Nudt1, Pon3, Serpine1, Ugt1a6, Ugt2a1 | |
| Chemokines and cytokines Involved in Inflammation | Ccl1, Ccl11, Ccl12, Ccl17, Ccl19, Ccl2, Ccl20, Ccl21a, Ccl22, Ccl24, Ccl25, Ccl3, Ccl4, Ccl5, Ccl6, Ccl7, Ccl8, Ccl9, Cx3cl1, Cxcl1, Cxcl10, Cxcl11, Cxcl12, Cxcl13, Cxcl14, Cxcl15, Cxcl2, Cxcl4, Cxcl5, Cxcl9, Ifna2, Ifng, Il10, Il11, Il12a, Il12b, Il13, Il15, Il16, Il17, Il17b, Il17e, Il18, Il1a, Il1b, Il2, Il20, Il22, Il3, Il4, Il5, Il6, Il9, Lta, Ltb, Mif, Scye1, Spp1, Tnf, Tnfsf5, Xcl1 | C5, CCL1, CCL11, CCL13, CCL15, CCL16, CCL17, CCL18, CCL19, CCL2, CCL20, CCL21, CCL23, CCL24, CCL25, CCL26, CCL3, CCL4, CCL5, CCL7, CCL8, CX3CL1, CXCL1, CXCL10, CXCL11, CXCL12, CXCL13, CXCL14, CXCL2, CXCL3, CXCL5, CXCL6, CXCL9, IFNA2, IFNG, IL10, IL11, IL12A, IL12B, IL13, IL15, IL16, IL17, IL17C, IL18, IL1A, IL1B, IL2, IL20, IL21, IL22, IL3, IL4, IL5, IL6, IL8, IL9, LTA, LTB, MIF, PF4, SCYE1, SPP1, TNF, TNFSF5, XCL1 |
| Chemokine Receptors and Cytokine Receptors Involved in Inflammation | Blr1, Ccr1, Ccr2, Ccr3, Ccr4, Ccr5, Ccr6, Ccr7, Ccr8, Ccr9, Cx3cr1, Cxcr3, Gpr2, Il10ra, Il10rb, Il12rb2, Il13ral, Il1r1, Il2rb, Il2rg, Il5ra, Il6ra, Il6st, Il9r, Xcr1 | BLR1, CCR1, CCR2, CCR3, CCR4, CCR5, CCR6, CCR7, CCR8, CCR9, CX3CR1, CXCR4, IL10RA, IL10RB, IL11RA, IL12RB1, IL12RB2, IL13RA1, IL13RA2, IL15RA, IL17R, IL18R1, IL1R1, IL1R2, IL1RN, IL2RA, IL2RB, IL2RG, IL5RA, IL6R, IL6ST, IL8RA, IL8RB, IL9R, XCR1 |
| Interleukins & Receptors Involved in Inflammation | Il10, Il10rb, Il12a, Il12b, Il13, Il18, Il8ra, Il8rb, Il1a, Il1b, Il1r1, Il1r2, Il1rn, Il2, Il20, Il3, Il4, Il5, Il6, Il9, Tollip | IL10, IL10RA, IL10RB, IL11, IL11RA, IL12A, IL12B, IL12RB1, IL12RB2, IL13, IL13RA1, IL13RA2, IL15, IL15RA, IL16, IL17, IL17C, IL17R, IL18, IL18R1, IL1A, IL1B, IL1R1, IL1R2, IL1RN, IL2, IL20, IL21, IL22, IL2RA, IL2RB, IL2RG, IL3, IL4, IL5, IL5RA, IL6, IL6R, IL6ST, IL8, IL8RA, IL8RB, IL9, IL9R, TOLLIP |
| TNF Ligands & Receptors Involved in Inflammation | Lta, Ltb, Tnf, Tnfrsf1a, Tnfrsf1b, Tnfsf5 | LTA, LTB, TNF, TNFRSF1A, TNFRSF1B, TNFSF5 |
| Other factors involved in Inflammatory Response Involved in Inflammation | C3, Fcer1g, Fcgr1, Igh-4, Itgam, Itgb2, Nos2, Prkca, Rac1, Tgfb1, Tlr1, Tlr2, Tlr3, Tlr4, Tlr5, Tlr6, Tlr7, Tlr8, Tlr9 | ABCF1, BCL6, C3, C4A, CEBPB, CRP, EDG3, ICEBERG, LTB4R |

In yet another exemplary embodiment, methods and compositions of the invention may be used to assess the distribution of a vector that has been administered to subject material. For example, a vector designed to transfect an organism may include a nucleic acid encoding a contrast protein operably linked to a suitable promoter. Optionally, a promoter will be selected to provide detectable levels of expression in a wide range of tissue types. For example, a strong constitutive promoter might be selected. The transfected biological material is imaged by MRI to identify cells that have been transfected with the vector. This exemplary method may be coupled with numerous different methods of administering the vector (e.g. introduction into an anatomical region or organ of particular interest, introduction into the circulatory system, the lymph system, etc.), and may be used to compare vector distribution and transcription levels obtained with each of these approaches. In the case of delivery systems that are targeted to a particular tissue, the exemplary methodology may be used to confirm or optimize tissue specificity. As another illustration, the present methods may be employed to optimize or develop a gene therapy protocol by allowing an investigator to determine the location and optionally the level of gene expression obtained after administration of a particular gene therapy system.

Many embodiments of the invention pertain to the generation of an artificially induced intracellular contrast agent. In many of the preceding embodiments, production of the intracellular contrast agent is achieved by introducing a nucleic acid encoding a direct contrast protein. Generally, production of the contrast agent may be achieved by alternative methods. For example, in situ production of an intracellular contrast agent may be stimulated by introducing a nucleic acid encoding an indirect contrast agent. An indirect contrast agent may be, for example, a protein or nucleic acid that regulates iron homeostasis, regulates expression of an endogenous gene coding for a direct contrast agent, and/or regulates the activity of an endogenous protein that may act as a direct contrast agent, such as, for example, ferritin. As another example, production of the contrast agent may be provoked by contacting the subject material with a composition that elicits production of the contrast agent. For example, cells may be contacted with an agent, such as an iron source, that causes cells to produce ferritin, which is an effective contrast agent. Accordingly, it is understood that the invention encompasses agents that are not direct contrast agents and may be neither nucleic acid nor protein but which nonetheless are useful for inducing in situ production of an intracellular contrast agent.

In certain aspects, nucleic acids of the invention may be introduced into biological material by using any of a variety of vectors, whether general or organism/tissue/cell-type specific, and in combination with any of a variety of delivery systems, such as for example, liposomes, viral particles, electroporation, etc. In additional aspects, proteins of the invention may also be administered directly to cells in a variety of ways, such as liposome fusion, electroporation, attachment to a moiety that is internalized by cells, etc.

In certain embodiments where a nucleic acid encoding a contrast protein is introduced into cells, it may be desirable to have that gene active or present in the cells for only a short period of time, or optionally for a regulated period of time. If desired, a transient transfection system may be used, and preferably a vector that permits expression for, on average, fewer than one or two days. Alternatively, or in conjunction, gene expression may be controlled by using an externally regulated promoter, or as a further example, the contrast gene or a portion thereof may be situated with respect to one or more recombination sites such that activation of a recombinase causes inactivation (or, if preferred, activation) of the nucleic acid encoding the contrast protein.

Specific sets of promoters can be used as markers to examine differential cellular activity in tissues. For example, the immediate early genes (IEGs), including c-fos, c-jun, and egr-1, encode for transcription factors that are transcriptionally regulated by an array of intracellular signaling pathways, and effect the transcriptional activity of downstream late genes. A variety of extracellular or physiological stimuli provide the switch that activates these cell signaling pathways. The activation of these IEGs results in a transcriptional cascade activating downstream genes that comprises the genetic circuitry for cells to respond to signals in their environment. For example, these signals may be induced in neurons by hormonal stimuli, sensory stimuli, stimulation of the motor cortex or other motor behaviors, and by various drugs and toxins that act on a variety of neurotransmitter systems. Because the IEGs can be transiently activated in an elegant tissue-specific manner, the transcriptional promoters of the IEGs used in conjunction with MRI reporters are ideal systems for studying the metabolic activation of tissues at the cellular level.

Many embodiments of the invention involve the use of nucleic acids encoding multiple contrast proteins, such as, for example, nucleic acids encoding heavy and light chains of a mammalian ferritin, or nucleic acids encoding a ferritin and a transferrin receptor.

In certain embodiments, the intracellular contrast agent will be chosen for safety in the subject material, and where the subject is a human subject, the intracellular contrast agent is preferably safe for use in humans.

3. Contrast Agents

In many aspects, as described above, methods of the invention will employ one or more contrast proteins that generate MRI contrast in vivo. The contrast protein will impart MRI contrast directly, or indirectly, by causing the cell to produce a secondary protein(s) that imparts MRI contrast. In the case of the direct effector, the contrast protein will typically form a complex that creates a change in at least one of relaxation times T1, T2, and/or T2*, where the change leads to a contrast effect during MRI. Often direct contrast proteins form metalloprotein complexes. In the case of indirect effectors, the contrast agent may be, for example, a protein or nucleic acid that regulates iron homeostasis, regulates expression of an endogenous gene coding for a direct contrast agent, and/or regulates the activity of an endogenous protein that may act as a direct contrast agent, thereby producing a contrast effect. In certain embodiments, the methods described herein may involve both direct and indirect contrast agents. In an exemplary embodiment, the methods and/or compositions described herein comprises an indirect contrast agent that affects iron homeostasis and a direct contrast agent, such as a metal binding protein.

In aspects of the invention employing a metal-binding polypeptide as a direct contrast agent, the metal-binding protein will preferably bind to one or more metals that provide effective contrasting. A variety of metals are effective as elements of a contrasting agent, particularly those with unpaired electrons in the d or f orbitals, such as, for example, iron (Fe), cobalt (Co), manganese (Mn), nickel (Ni), gadolinium (Gd), etc. As noted above, iron is of particular interest because it is present at relatively high levels in mammals and most other organisms, and therefore, detectable accumulations of iron may be generated without the aid of exogenous iron supplementation. Accordingly, preferred metal-binding proteins of the invention are iron-binding proteins. In those embodiments employing a T2 contrast agent, the geometry of metal binding is not important, but the contrast will tend to be greater when larger amounts of metal are concentrated together. In certain preferred embodiments, the effective metal should be bound into a metal-rich aggregate, optionally a crystal-like aggregate, greater than 10 picometers in diameter, optionally greater than 100 picometers, greater than 1 nanometer, greater than 10 nanometers or greater than 100 nanometers in diameter. Alternatively the metal-rich aggregate should be in the range of 1-100 nanometers in diameter within the polypeptide complex. In a particularly preferred embodiment, the metal-rich aggregate exhibits properties of superparamagnetism. When an iron-binding polypeptide is used, it is preferable if the polypeptide retains the iron in the nontoxic Fe(III) oxidation state. Fe(II) is also an effective contrasting agent, but Fe(II) may participate in the iron-catalyzed Fenton reaction that yields potentially damaging hydroxyl radicals.

In a preferred embodiment, a direct contrast protein of the invention has the following properties: rapid intracellular protein assembly and metal loading, the tendency to promote formation of a metal-rich aggregate that has a large paramagnetic susceptibility, and the ability to retain the metal in a relatively non-toxic form (e.g. in the case of iron, the Fe(III) state).

In certain aspects, metal-binding polypeptides may also change the contrast properties of a cell by perturbing metal metabolism and stimulating the expression of endogenous metal-binding polypeptides that have contrast effects. This may also lead to an accumulation or depletion of a particular metal in the cell. For example, transient expression of high affinity iron-binding proteins may create a temporary decrease in the intracellular labile iron pool and stimulate production of transferrin receptor, thereby increasing the net iron uptake into the cell.

Although the exact binding affinity of a metal-binding protein for different metals is not critical, it is generally expected that polypeptides with a sub-nanomolar affinity for one or more effective metals may be useful, and optionally the polypeptide will have a dissociation constant less than $10^{-15}$ M, $10^{-20}$ M, or less for one or more effective metals. It is understood that many metal binding proteins will bind to more than one type of metal. For example, lactoferrin will form complexes with metals such as manganese and zinc. Ferritin-iron complexes are generally expected to contain some small (perhaps infinitesimal) amounts of other metals. In general, iron binding proteins are likely to bind to metals such as manganese, cobalt, zinc and chromium, although in vivo the concentration and abundance of iron is so much higher than these other metals that an iron binding protein will be primarily associated with iron.

Several exemplary metal-binding polypeptides of the invention are provided. This is in no way intended to be an exhaustive list, and, in view of the teachings herein, one of skill in the art will be able to identify or design other useful metal-binding polypeptides.

In certain exemplary embodiments, one or more ferritins may be used as a contrast protein. Ferritins of the invention include any of the group of diiron-carboxylate proteins characterized by the tendency to form a dimeric or multimeric structure with bound iron and having a helix-bundle structure comprising an iron-coordinating Glu residue in a first helix and a Glu-X-X-His motif in a second. Certain ferritins maintain bound iron in a primarily Fe(III) form. A list of exemplary ferritins is provided in Table 2. This list is intended to provide examples and is not intended to be comprehensive. Many known ferritins are not included, and it is understood that most vertebrate species will have a form of ferritin that can be used as a contrast agent. In view of this specification, one of ordinary skill in the art will be able to identify additional ferritin homologs. In certain embodiments, a ferritin for use as a contrasting agent should have at least 50% identity with the amino acid sequence of SEQ ID NO:2 and/or SEQ ID NO:4, and optionally at least 60%, 70%, 80%, 90%, 95%, 98%, 99% or 100% identity with the amino acid sequence of SEQ ID NO:2 and/or SEQ ID NO:4.

In many embodiments, methodologies of the invention will employ a vertebrate ferritin as a contrast agent. Vertebrate ferritins typically form a large complex that assembles in a shell to delimit a cavity where iron is accumulated in a mineral and compact form. Most mammalian ferritins are composed of two subunit types, the H- and L-chains. Typically the endogenous mRNAs for the two chains have nearly identical iron-responsive elements (IREs) close to the 5' termini that regulate ferritin translation by binding to iron-regulatory proteins (IRPs). When designing nucleic acid constructs for the ectopic expression of ferritins, it will often be desirable to omit or otherwise disrupt the IRE sequences. Contacting cultured cells with an elevated iron concentration typically causes a strong up-regulation of both the L- and H-chains, whereas treatment with iron chelating agents, such as desferrioxamine, suppresses ferritin production. Preferred ferritins of the invention catalyze both an iron oxidation step from the Fe(II) form to the Fe(III) form and also catalyze the nucleation and growth of an iron mineral core. In the case of ferritins composed of multiple subunits, it will typically be desirable to express all subunits at a stoichiometry approximating that found in the native complexes. However, it is notable that a wide range of subunit ratios will typically be effective. For example, human H chain is capable of forming a homopolymer that binds iron. Excess ferritin resulting from overexpression is typically degraded inside the cell, and the primary decay product is hemosiderin deposits; these are also effective as contrast agents.

TABLE 2

Exemplary Ferritin Proteins and Nucleic Acids

| Name | Amino Acid Sequence (Acc. No.) | Nucleic Acid Sequence (Acc. No.) |
|---|---|---|
| ferritin, heavy polypeptide 1 [Homo sapiens] | AAH16009.1 | BC016009.1 |
| ferritin, light polypeptide [Homo sapiens] | XP_050469.1 | XM_050469.1 |
| ferritin heavy chain [Mus musculus] | NP_034369.1 | NM_010239.1 |
| ferritin light chain 1 [Mus musculus] | NP_034370.1 | NM_010240.1 |
| ferritin light chain 2 [Mus musculus] | NP_032075.1 | NM_008049.1 |
| ferritin subunit H [Rattus norvegicus] | NP_036980.1 | NM_012848.1 |
| ferritin light chain 1 [Rattus norvegicus] | NP_071945.1 | NM_022500.1 |
| ferritin heavy chain [Cavia porcellus] | BAB70615.1 | AB073371.1 |
| ferritin light chain [Cavia porcellus] | AAF36408.1 | AF233445_1 |
| ferritin heavy chain [rabbit] | P25915 | |
| ferritin light chain [rabbit] | S01239 | |
| ferritin H subunit [Bos taurus] | BAA24818.1 | AB003093.1 |
| ferritin L subunit [Bos taurus] | BAA24819.1 | AB003094.1 |
| ferritin heavy chain [Gallus gallus] | A26886 | |
| ferritin [Canis familiaris] | AAK82992.1 | AF285177.1 |
| ferritin H chain [Macaca mulatta] | AAF98711.1 | AF162481_1 |
| ferritin heavy chain [Xenopus laevis] | FRXL | |
| ferritin heavy chain [Danio rerio] | AAG37837.1 | AF295373_1 |
| yolk ferritin [Paragonimus westermani] | AAG17056.1 | AF188720_1 |
| ferritin [Taenia saginata] | CAA65097.1 | |
| 26 kDa ferritin subunit [Galleria mellonella] | AAG41120.1 | AF142340.1 |
| nonheme iron-containing ferritin (pfr) [Helicobacter pylori 26695] | NP_207447.1 | NC_000915.1 |
| ferritin [Glycine max] | AAL09920.1 | AY049920.1 |

In certain embodiments, H and L ferritin subunits may be expressed as fusion proteins. These single chain chimeric ferritins ("sc-Ft") have a fixed stoichiometry of the subunits (e.g., 1:1 ratio, although ratios such as 2:1 or 1:2 may also be selected) when expressed in cells. The subunits may be in essentially any order and the subunits may be fused directly to each other, or there may be a linker between subunits. Preferably the linker is flexible so as to facilitate folding of the subunits with respect to each other. The linker polypeptide may be designed so as to impart a variety of functions to the sc-Ft. For example, a linker could encode a unique epitope tag (e.g., the HA-epitope, YPYDVPDYA; His, HHHHHH; c-MYC, EQKLISEEDL; VSV-G, YTDIEMNRLGK; HSV, QPELAPEDPED; V5 GKPIPNPLLGLDST). Such epitope tags can easily be detected using immunohistochemistry using highly selective antibodies, thus facilitating histological examination of the cells and tissues expressing the sc-Ft reporter, for example, after MRI examination. Alternatively, these epitope tags can be used to biochemically isolate the recombinant sc-Ft proteins from a cell lysate using immunopurification or other affinity reagents. Additionally, functional markers such as fluorescent proteins (examples are variants of GFP or DS-red) or enzymes (such as β-galactosidase, GST or HRP) could also be incorporated into the linker and thereby simultaneously linking and labeling the two FT subunits; the linker can then be detected using fluorescence microscopy, histology, or biochemistry techniques. Furthermore, the linker polypeptide can be designed to target specific proteins within the cell, i.e., the linker may contain subcellular localization signals. For example, the linker may provide signals for modification by ubiquitinating enzymes, which in turn could be used to promote cellular degradation of the sc-Ft reporter. In this way one could designate a degradation pathway for the reporter, which might be a useful feature when rapid turn-on and turn-off kinetics of the MRI reporter activity are desirable, or if the MRI reporter is not naturally cleared at an adequate rate in a particular cell type.

The linker polypeptide can also be used to modify the MRI contrasting function and stability of the sc-Ft reporter. The final structure of the ferritin shell formed from single chain chimeric duplex molecules can depend on the flexibility, length, chemical properties (e.g., hydrobicity and charge distribution) and steric filling of the linker polypeptide. Thus via linker design one can engineer new ferritin molecules with modified structures, stabilities in vivo, and enhanced functional properties (i.e., enhanced NMR relaxivity). For example, increasing the steric volume, length, or rigidity of the linker polypeptide may increase the overall size of the fully formed ferritin shell and consequently facilitate greater iron loading capacity. Additionally, other changes in structure may increase iron loading kinetics into the shells. Furthermore, the linker may modify the shell's structure in such a way that its stability and turnover rate in the cell is affected, and this can be used as an additional means to control MRI reporter turn-on and turn-off in cells.

In a further embodiment, a metal binding protein of the invention is a metal scavenger, defined as a protein that binds metal with very high affinity through a siderophore. Such proteins may be used as contrast agents. While not wishing to be bound to a mechanism, it is expected that such proteins will act primarily as indirect contrast agents. For example, iron scavenging proteins expressed in a cell may scavenge and tightly bind iron from the labile iron pool within the intracellular space. Thus MRI contrast may be enhanced by a combination of the iron-bound chelate itself and the additional iron that is sequestered and stored as a result of the cell's own iron regulation mechanisms. Exemplary siderophores that may be present in metal scavenging proteins include hemoglobin, and any other agent that provides an octahederal coordination sphere for the iron, usually formed by six oxygen atoms. In general these fall into two categories: (a) catechols such as enterobactin which comprises a cyclic structure composed of three molecules of 2,3-dihydroxy-N-benzoyl serine. Further examples include agents wherein the serine is substituted with either a glycine or a threonine. Also included herein are catechol siderophores having linear rather than cyclic structures such as pseudobactin; (b) Hydroxamates comprise a large and variable group having either cyclic or linear peptides containing various types of hydroxamic acids. Common examples include ferrichrome, ferrioxamine, and aerobactin. Further examples include plant siderophores such as phytosiderophore. Exemplary metal scavenging proteins include ferric binding proteins of the siderophilin family, such as mammalian transferrins, ovotransferin, lactoferrins, melanotransferrin, sertoli transferrin, neurotransferrin, mucosal transferrin, and bacterial transferrins, such as those found in *Haemophilus influenzae, Neisseria gonorrhoeae*, and *Neisseria meningitidis.*

In further embodiments, an iron regulatory protein (IRP) may be used as a contrast protein. IRPs are iron-regulating RNA binding proteins that modulate synthesis of proteins that function in the uptake (e.g. transferrin receptor), utilization (e.g. erythroid 5-aminolevulinate synthase) or storage (e.g. H-ferritin and L-ferritin) of iron. Proteins regulated by IRPs are encoded by mRNAs that include one or more stem-loop motifs, termed an Iron Responsive Element (IRE). Under low iron conditions, IRPs bind to IREs and modulate the stability or translation of the affected mRNA. In general, when an IRE is positioned in the 5' UTR region of an mRNA (e.g. the ferritins), the IRP blocks translation, causing decreased protein production in low iron conditions. When an IRE is positioned in the 3'UTR (e.g. transferrin receptor), the IRP typically stabilizes the mRNA, thereby increasing production of the gene product in response to low iron conditions. Mice having a targeted deletion of the gene encoding IRP2 show significant accumulations of iron in neural tissues (LaVaute et al., 2001, *Nat. Genet.* 27(2):209-14). Accordingly, manipulation of IRPs by, for example, antisense or RNAi methodologies may provide contrast effects. IRPs of the invention will typically have the ability to bind to IREs in an iron-regulated manner. Preferred IRPs of the invention will be vertebrate IRPs such as: human IRP1 (Acc. Nos. P21399 and Z11559), human IRP2 (Acc. Nos. AAA69901 and M58511), rat IRE-BP1 (Acc. Nos. Q63270 and L23874), mouse IRE-BP1 (Acc. Nos. P28271 and X61147), chicken IRE-BP (Acc. No. Q90875 and D16150), etc. In general, it will be desirable to employ an IRP that binds to the IREs of the subject biological material, and in certain embodiments, this may be accomplished by using an IRP that is derived from the subject species. In certain aspects of the invention, a contrast protein comprises an amino acid sequence at least 60% identical to that of human IRP1 and/or IRP2, and optionally at least 70%, 80%, 90%, 95%, 98%, 99% or 100% identical.

In further aspects, a contrast protein of the invention may be one that perturbs cellular iron homeostasis. For example, a transferrin receptor protein, and/or a molecule that regulates the expression and/or function of a transferrin receptor protein, may be used as a contrast agent. Transferrin receptor mediates the receptor mediated endocytosis of the iron-carrying protein transferrin and thereby mediates cellular iron uptake. Therefore, in one embodiment of the invention, the level and/or activity of a transferrin receptor in targeted cells may be modulated so as to produce an increase in cellular iron uptake thereby causing the cell to produce ferritin. The end result will be an accumulation of excess ferritin that will yield MRI contrast. Exemplary transferrin receptors include SEQ ID Nos: 16, 18, 20 and 22. In certain aspects of the invention, a contrast protein comprises an amino acid sequence at least 60% identical to that of human transferrin receptor 1 ("TfR-1") and/or human transferrin receptor 2 ("TfR-2"), and optionally at least 70%, 80%, 90%, 95%, 98%, 99% or 100% identical, and preferably retains transferrin receptor activity. As noted in the examples below, the combined expression of a transferrin receptor and the ferritin L and H subunits may provide a desirable contrast signal.

In a further embodiment, a contrast protein is a divalent metal transporter, such as DMT-1 or Nramp-2. Recently, the divalent metal transporter protein, DMT-1 isoform II, has been shown to co-localize with the recycling TfR-1. DMT-1 mediates the transport of iron across the membrane from the lumen of the late endosome into the cytoplasm where the labile iron is sequestered by ferritin. These may be coexpressed with other proteins to achieve enhanced contrast effects. The major carrier of iron in the body is transferrin, and transferrin-iron complexes are taken up into cells by the transferrin receptor (TfR) dependent pathway, predominantly via TfR-1. The primary transporter responsible for metal transport by most cell types in the body is the divalent metal transporter (DMT-1), which transports the iron carried into the cell by TfR-1 from the endosomal system into the cytoplasm where it may be used or stored into FT. Upregulating TfR-1 and/or DMT-1 along with FT transgenes may be used to enhance Fe transport into target cells under normal physiological conditions, boost iron loading into FT, and enhance NMR relaxation rates (i.e. image contrast). Overexpression of TfR and/or DMT-1 alone without the FT transgenes may also boost the LIP and lead to endogenous FT upregulation, which in turn will produce MRI contrast. See for example, Canonne-Hergaux, F., J. E. Levy, M. D. Fleming, L. K. Montross, N. C. Andrews, and P. Gros, Expression of the DMT1 (NRAMP2/DCT1) iron transporter in mice with genetic iron overload disorders. Blood, 97(4): p. 1138-1140 (2001); Moos, T., D. Trinder, and E. H. Morgan, Effect of iron status on DMT1 expression in duodenal enterocytes from beta(2)-microglobulin knockout mice. Am J Physiol Gastrointest Liver Physiol, 283(3): p. G687-G694 (2002); Picard, V., G. Govoni, N. Jabado, and P. Gros, Nramp 2 (DCT1/DMT1) expressed at the plasma membrane transports iron and other divalent cations into a calcein-accessible cytoplasmic pool. J Biol Chem, 275(46): p. 35738-35745 (2000).

Recently a mammalian intron-less gene encoding for a mitochondrial ferritin homolog, Mt-FT, has been described. [see, for example, Levi, S., B. Corsi, M. Bosisio, R. Invemizzi, A. Volz, D. Sanford, P. Arosio, and J. Drysdale, A human mitochondrial ferritin encoded by an intronless gene. J Biol Chem, 276(27): p. 24437-24440 (2001)]. Mt-FT is an attractive candidate for use as a primary MRI reporter because (i) it is encoded on a single, small, intron-less gene, (ii) it can assemble functional shells as a homopolymeric FT, (iii) its expression can be retargeted to the cell cytoplasm, and (iv) it exhibits the capacity to scavenge iron efficiently. Modified versions of Mt-FT may also be employed. Such modifications may be designed to incorporate a unique epitope tag and/or optionally other modifications such that expression will be targeted to the cytoplasm by replacement of 5' sequences and elimination of the native mitochondrial signaling sequence.

Other potential metalloprotein reporters comprise FT homologs derived from bacteria (prokaryotic ferritins, or "Pk-FTs"). The Pk-FTs can be divided into three classes: (i) those containing heme called bacterioferritins; (ii) those lacking heme coordination sites, called bacterial ferritins [reviewed by Carrondo, M. A., Ferritins, iron uptake and storage from the bacterioferritin viewpoint. Embo J, 22(9): p. 1959-1968 (2003); Andrews, S. C., Iron storage in bacteria. Adv Microb Physiol, 40: p. 281-351 (1998)]; and (iii) those having a similar physical structure but assembled from 12 subunits, called dodecameric ferritin-like molecules [Ilari, A., P. Ceci, D. Ferrari, G. L. Rossi, and E. Chiancone, Iron incorporation into *Escherichia coli* Dps gives rise to a ferritin-like microcrystalline core. J Biol Chem, 277(40): p. 37619-37623 (2002)]. Two classes of genes derive from a common laboratory strain of *E. coli* (Ec). Ec BFr [See Abdul-Tehrani, H., A. J. Hudson, Y. S. Chang, A. R. Timms, C. Hawkins, J. M. Williams, P. M. Harrison, J. R. Guest, and S. C. Andrews, Ferritin mutants of *Escherichia coli* are iron deficient and growth impaired, and fur mutants are iron deficient. J Bacteriol, 181(5): p. 1415-1428 (1999); Andrews, S. C., P. M. Harrison, and J. R. Guest, Cloning, sequencing, and mapping of the bacterioferritin gene (bfr) of *Escherichia coli* K-12. J Bacteriol, 171(7): p. 3940-3947 (1989); Hudson, A. J., S. C. Andrews, C. Hawkins, J. M. Williams, M. Izuhara, F. C. Meldrum, S. Mann, P. M. Harrison, and J. R. Guest, Overproduction, purification and characterization of the *Escherichia coli* ferritin. Eur J Biochem, 218(3): p. 985-995 (1993).], and the Ec FtnA [Stillman, T. J., P. D. Hempstead, P. J. Artymiuk, S. C. Andrews, A. J. Hudson, A. Treffry, J. R. Guest, and P. M. Harrison, The high-resolution X-ray crystallographic structure of the ferritin (EcFtnA) of *Escherichia coli*; comparison with human H ferritin (HuHF) and the structures of the Fe(3+) and Zn(2+) derivatives. J Mol Biol, 307(2): p. 587-603 (2001)] proteins may be expressed in mammalian cells as MRI reporters. These sequences may be modified to contain epitope tags.

A set of exemplary constructs for expressing contrast proteins is shown in Table 3, below.

TABLE 3

Examples of constructs for expression of contrast proteins and combinations of transgenes.

| cDNA | Name | Combination with |
|---|---|---|
| Sc-FT | single-chain FT chimeric duplex | TfR-1 and/or DMT-1 |
| Mt-FT | cytoplasmic-targeted mitochondrial FT | TfR-1 and/or DMT-1 |
| Pk-FT | prokaryotic FT homologs | TfR-1 and/or DMT-1 |
| TfR-1 | transferrin receptor-1 | Sc-FT, Mt-FT, Pk-FT |
| DMT-1 | divalent metal transporter | Sc-FT, Mt-FT, Pk-FT |

In further embodiments, contrast proteins of the invention may be engineered, by for example, employing techniques of molecular biology. For example, it is possible to modify the structure of the subject contrast proteins for such purposes as enhancing contrast efficacy, stability (e.g., increased or decreased resistance to proteolytic degradation in vivo), antigenicity, or safety, among other characteristics. Such modified proteins can be produced, for instance, by amino acid substitution, deletion, or addition. In addition, simple variants of any of the proteins discussed herein may be obtained by conservative substitution. For instance, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W.H. Freeman and Co., 1981).

This invention further contemplates methods of generating sets of combinatorial mutants of the subject contrast proteins, as well as functional truncation mutants. The purpose of screening such combinatorial libraries is to generate, for example, engineered contrast proteins with any number of desirable qualities such as those mentioned above.

There are many ways by which the library of potential engineered contrast proteins can be generated. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential contrast protein sequences. Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, engineered contrast proteins can be generated and isolated from a library by screening using, for example, alanine scanning mutagenesis and the like (see e.g. Ruf et al., (1994) Biochemistry 33:1565-1572; Wang et al., (1994) J. Biol. Chem. 269:3095-3099; Balint et al., (1993), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34).

Whether a change in the amino acid sequence of a polypeptide results in a functional homologue can be readily determined by assessing the ability of the variant polypeptide to, for example, bind the desired metal, produce sufficient MRI contrast in cells, and produce reduced cell toxicity.

In further aspects, any combination of contrast proteins may employed to obtain the desired contrast effects.

4. Constructs and Vectors

In certain aspects, the invention provides vectors and nucleic acid constructs comprising nucleic acids encoding one or more contrast agents. Other features of the vector or construct will generally be designed to supply desirable characteristics depending on how the contrast agent is to be generated and used. Exemplary desirable characteristics include but are not limited to, gene expression at a desired level, gene expression that is reflective of the expression of a different gene, easy clonability, transient or stable gene expression in subject cells, etc.

In certain aspects, it is desirable to use a vector that provides transient expression of the contrast agent. Such vectors will generally be unstable inside a cell, such that the nucleic acids necessary for expression of the contrast agent are lost after a relatively short period of time. Optionally, transient expression may be effected by stable repression. Exemplary transient expression vectors may be designed to provide gene expression for an average time of hours, days, weeks, or perhaps months. Often transient expression vectors do not recombine to integrate with the stable genome of the host. Exemplary transient expression vectors include: adenovirus-derived vectors, adeno-associated viruses, herpes simplex derived vectors, hybrid adeno-associated/herpes simplex viral vectors, influenza viral vectors, especially those based on the influenza A virus, and alphaviruses, for example the Sinbis and semliki forest viruses.

In some aspects the invention provides a vector or construct comprising a readily clonable nucleic acid encoding a contrast protein. For example, the coding sequence may be flanked by a polylinker on one or both sides. Polylinkers are useful for allowing one of skill in the art to readily insert the coding sequence in a variety of different vectors and constructs as required. In another example, the coding sequence may be flanked by one or more recombination sites. A variety of commercially available cloning systems use recombination sites to facilitate movement of the desired nucleic acid into different vectors. For example, the Invitrogen Gateway™ technology utilizes a phage lambda recombinase enzyme to recombine target nucleic acids with a second nucleic acid. Each nucleic acid is flanked with appropriate lambda recognition sequence, such as attL or attb. In other variations, a recombinase such as topoisomerase I may be used with nucleic acids flanked by the appropriate recognition sites. For example, the Vaccinia virus topoisomerase I protein recognizes a (C/T)CCTT sequence. These recombination systems permit rapid shuffling of flanked cassettes from one vector to another as needed. A construct or vector may include both flanking polylinkers and flanking recombination sites, as desired.

In certain aspects, the contrast gene is operably linked to a promoter. The promoter may for example, be a strong or constitutive promoter, such as the early and late promoters of SV40, or adenovirus or cytomegalovirus immediate early promoter. Optionally it may be desirable to use an externally regulated promoter, such as a tet promoter, IPTG-regulated promoters (GAL4, Plac), or the trp system. In view of this specification, one of skill in the art will readily identify other useful promoters depending on the downstream use. For example, the invention may utilize exemplary promoters such as the T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. In addition, as noted above, it may be desirable to have a contrast gene operably linked to a promoter that provides useful information about the condition of the cell in which it is situated. In certain embodiments, it is anticipated that it will be desirable to achieve a concentration of contrast protein within target cells that permits detection above background noise, and with certain detection systems this will translate into a protein concentration of at least 1 nM or at least 10 nM.

Vectors of the invention may be essentially any nucleic acid designed to introduce and/or maintain a contrast gene in a cell or virus. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) may be used. Other vector systems suitable for gene therapy are described below.

5. Cells, Organized Cell Cultures, and Tissues

In many aspects, the invention provides cells, organized cell cultures, and tissues comprising a nucleic acid that encodes a contrast agent. Methods for generating transformed or transfected cells are widely known in the art, and it is anticipated that methods described herein may be used with essentially any cell type of interest, including but not limited to bacterial, fungal, plant and animal cells. Preferred embodiments of the invention employ mammalian cells. Cells of particular interest may include transformed cells or other cells that either are part of a tumor or are useful as a model for cancer in vitro, stem or progenitor cells, and cells prepared for a cell therapy for a patient. Cells of the invention may be cultured cells, cell lines, cells situated in tissues and/or cells that are part of an organism.

It is further anticipated that cells may be used to generate organized cell cultures (i.e. cell cultures developing a non-random structure) and to generate organs or organ-like structures for transplant into subjects. It may be useful to non-invasively monitor some aspect of gene expression in such cells, or to otherwise provide MRI contrast in such cells. For example, muscle progenitor cells may be used to develop muscle-like organs for administration to injured muscle or for administration as a packet of cells that produce a therapeutic protein (see e.g. U.S. Pat. Nos. 5,399,346; 6,207,451; 5,538,722). Other cell culture methods have been used to produce neural, pancreatic, liver and many other organ types for transplant (see e.g. U.S. Pat. Nos. 6,146,889; 6,001,647; 5,888,705; 5,851,832 and PCT publication nos. WO 00/36091; WO 01/53461; WO 01/21767). Cells of this nature may be stably transfected with a contrast gene at an early stage of culture, or the organized culture may be transiently or stably transfected at a later point in culture to assess some aspect of cell function. Transfected cells may be administered to subjects in order to deliver a gene product, and this methodology is effective as an ex vivo gene therapy or cell therapy method. A nucleic acid encoding a contrast protein may be introduced into such cells and administered to a subject in order to monitor gene expression or viability of the administered cells. Cells transfected with the gene adenosine deaminase have been delivered to patients as an ex vivo gene therapy cure for Severe Combined Immunodeficiency Syndrome (SCID) (Cavazzana-Calvo et al., 2000, *Science* 288(5466):669-72).

6. Nucleic Acids for Delivery to Organisms and in vitro Tissues

Instead of ex vivo modification of cells, in many situations one may wish to modify cells in vivo. For this purpose, various techniques have been developed for modification of target tissue and cells in vivo. A number of viral vectors have been developed, such as described above, which allow for transfection and, in some cases, integration of the virus into the host. See, for example, Dubensky et al. (1984) Proc. Natl. Acad. Sci. USA 81, 7529-7533; Kaneda et al., (1989) Science 243, 375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used. Generally, in human subjects, it will be preferable to design the nucleic acid and/or the delivery system to provide transient expression of the nucleic acid encoding the contrast agent.

In general, the manner of introducing the nucleic acid will depend on the nature of the tissue, the efficiency of cellular modification required, the number of opportunities to modify the particular cells, the accessibility of the tissue to the nucleic acid composition to be introduced, and the like. The DNA introduction need not result in integration. In fact, non-integration often results in transient expression of the introduced DNA, and transient expression is often sufficient or even preferred.

Any means for the introduction of polynucleotides into mammals, human or non-human, may be adapted to the practice of this invention for the delivery of the various constructs of the invention into the intended recipient. In one embodiment of the invention, the nucleic acid constructs are delivered to cells by transfection, i.e., by delivery of "naked" nucleic acid or in a complex with a colloidal dispersion system. A colloidal system includes macromolecule complexes, nanocapsules, microspheres, beads, and lipid-based systems including oil-in-water emulsions, micelles, mixed micelles, and liposomes. An exemplary colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

Optionally, liposomes or other colloidal dispersion systems are targeted. Targeting can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. A certain level of targeting may be achieved through the mode of administration selected.

In certain variants of the invention, the nucleic acid constructs are delivered to cells, and particularly cells in an organism or a cultured tissue, using viral vectors. The transgene may be incorporated into any of a variety of viral vectors useful in gene therapy, such as recombinant retroviruses, adenovirus, adeno-associated virus (AAV), herpes simplex derived vectors, hybrid adeno-associated/herpes simplex viral vectors, influenza viral vectors, especially those based on the influenza A virus, and alphaviruses, for example the Sinbis and semliki forest viruses, or recombinant bacterial or eukaryotic plasmids. The following additional guidance on the choice and use of viral vectors may be helpful to the practitioner. As described in greater detail below, such embodiments of the subject expression constructs are specifically contemplated for use in various in vivo and ex vivo gene therapy protocols.

A. Herpes Virus Systems

A variety of herpes virus-based vectors have been developed for introduction of genes into mammals. For example, herpes simplex virus type 1 (HSV-1) is a human neurotropic virus of particular interest for the transfer of genes to the nervous system. After infection of target cells, herpes viruses often follow either a lytic life cycle or a latent life cycle, persisting as an intranuclear episome. In most cases, latently infected cells are not rejected by the immune system. For example, neurons latently infected with HSV-1 function normally and are not rejected. Some herpes viruses possess cell-type specific promoters that are expressed even when the virus is in a latent form.

A typical herpes virus genome is a linear double stranded DNA molecule ranging from 100 to 250 kb. HSV-1 has a 152 kb genome. The genome may include long and short regions (termed UL and US, respectively) which are linked in either orientation by internal repeat sequences (IRL and IRS). At the non-linker end of the unique regions are terminal repeats (TRL and TRS). In HSV-1, roughly half of the 80-90 genes are non-essential, and deletion of non-essential genes creates space for roughly 40-50 kb of foreign DNA (Glorioso et al, 1995). Two latency active promoters which drive expression of latency activated transcripts have been identified and may prove useful for vector transgene expression (Marconi et al, 1996).

HSV-1 vectors are available in amplicons and recombinant HSV-1 virus forms. Amplicons are bacterially produced plasmids containing OriC, an *Escherichia coli* origin of replication, OriS (the HSV-1 origin of replication), HSV-1 packaging sequence, the transgene under control of an immediate-early promoter & a selectable marker (Federoff et al, 1992). The amplicon is transfected into a cell line containing a helper virus (a temperature sensitive mutant) which provides all the missing structural and regulatory genes in trans. More recent amplicons include an Epstein-Barr virus derived sequence for plasmid episomal maintenance (Wang & Vos, 1996). Recombinant viruses are made replication deficient by deletion of one the immediate-early genes e.g. ICP4, which is provided in trans. Deletion of a number of immediate-early genes substantially reduces cytotoxicity and allows expression from promoters that would be silenced in the wild type latent virus. These promoters may be of use in directing long term gene expression. Replication-conditional mutants replicate in permissive cell lines. Permissive cell lines supply a cellular enzyme to complement for a viral deficiency. Mutants include thymidine kinase (During et al, 1994), ribonuclease reductase (Kramm et al, 1997), UTPase, or the neurovirulence factor g34.5 (Kesari et al, 1995). These mutants are particularly useful for the treatment of cancers, killing the neoplastic cells which proliferate faster than other cell types (Andreansky et al, 1996, 1997). A replication-restricted HSV-1 vector has been used to treat human malignant mesothelioma (Kucharizuk et al, 1997). In addition to neurons, wild type HSV-1 can infect other non-neuronal cell types, such as skin (Al-Saadi et al, 1983), and HSV-derived vectors may be useful for delivering transgenes to a wide array of cell types. Other examples of herpes virus vectors are known in the art (U.S. Pat. No. 5,631,236 and WO 00/08191).

B. Adenoviral Vectors

A viral gene delivery system useful in the present invention utilizes adenovirus-derived vectors. Knowledge of the genetic organization of adenovirus, a 36 kB, linear and double-stranded DNA virus, allows substitution of a large piece of adenoviral DNA with foreign sequences up to 8 kB. In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. In addition, adenoviral vector-mediated transfection of cells is often a transient event. A combination of immune response and promoter silencing appears to limit the time over which a transgene introduced on an adenovirus vector is expressed.

Adenovirus is particularly suitable for use as a gene transfer vector because of its mid-sized genome, ease of manipulation, high titer, wide target-cell range, and high infectivity. The virus particle is relatively stable and amenable to purification and concentration, and as above, can be modified so as to affect the spectrum of infectivity. Additionally, adenovirus is easy to grow and manipulate and exhibits broad host range in vitro and in vivo. This group of viruses can be obtained in high titers, e.g., $10^9$-$10^{11}$ plaque-forming unit (PFU)/ml, and they are highly infective. Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109-127). Expression of the inserted polynucleotide of the invention can be under control of, for example, the E1A promoter, the major late promoter (MLP) and associated leader sequences, the viral E3 promoter, or exogenously added promoter sequences.

The genome of an adenovirus can be manipulated such that it encodes a gene product of interest, but is inactivated in terms of its ability to replicate in a normal lytic viral life cycle (see, for example, Berkner et al., (1988) BioTechniques 6:616; Rosenfeld et al., (1991) Science 252:431-434; and Rosenfeld et al., (1992) Cell 68:143-155). Suitable adenoviral vectors derived from the adenovirus strain Ad type 5 dl324 or other strains of adenovirus (e.g., Ad2, Ad3, Ad7 etc.) are well known to those skilled in the art.

Adenoviruses can be cell type specific, i.e., infect only restricted types of cells and/or express a transgene only in restricted types of cells. For example, the viruses may be engineered to comprise a gene under the transcriptional control of a transcription initiation region specifically regulated by target host cells, as described e.g., in U.S. Pat. No. 5,698,443, by Henderson and Schuur, issued Dec. 16, 1997. Thus, replication competent adenoviruses can be restricted to certain cells by, e.g., inserting a cell specific response element to regulate a synthesis of a protein necessary for replication, e.g., E1A or E1B.

DNA sequences of a number of adenovirus types are available from Genbank. For example, human adenovirus type 5 has GenBank Accession No. M73260. The adenovirus DNA sequences may be obtained from any of the 42 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by restriction digest, linker ligation or filling in of ends, and ligation.

Adenovirus producer cell lines can include one or more of the adenoviral genes E1, E2a, and E4 DNA sequence, for packaging adenovirus vectors in which one or more of these genes have been mutated or deleted are described, e.g., in PCT/US95/15947 (WO 96/18418) by Kadan et al.; PCT/US95/07341 (WO 95/346671) by Kovesdi et al.; PCT/FR94/00624 (WO94/28152) by Imler et al.; PCT/FR94/00851 (WO 95/02697) by Perrocaudet et al., PCT/US95/14793 (WO96/14061) by Wang et al.

C. AAV Vectors

Yet another viral vector system useful for delivery of the subject polynucleotides is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97-129).

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector.

AAV is also one of the few viruses that may integrate its DNA into non-dividing cells, e.g., pulmonary epithelial cells, and exhibits a high frequency of stable integration (see for example Flotte et al., (1992) Am. J. Respir. Cell. Mol. Biol. 7:349-356; Samulski et al., (1989) J. Virol. 63:3822-3828; and McLaughlin et al., (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251-3260 can be used to introduce DNA into cells. A variety of nucleic acids have been introduced into different cell types using AAV vectors (see for example Hermonat et al., (1984) PNAS USA 81:6466-6470; Tratschin et al., (1985) Mol. Cell. Biol. 4:2072-2081; Wondisford et al., (1988) Mol. Endocrinol. 2:32-39; Tratschin et al., (1984) J. Virol. 51:611-619; and Flotte et al., (1993) J. Biol. Chem. 268:3781-3790).

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is usually about 4.4 kb (Kotin, R. M., Human Gene Therapy 5:793-801, 1994 and Flotte, et al. J. Biol. Chem. 268:3781-3790, 1993).

AAV stocks can be produced as described in Hermonat and Muzyczka (1984) PNAS 81:6466, modified by using the pAAV/Ad described by Samulski et al. (1989) J. Virol. 63:3822. Concentration and purification of the virus can be achieved by reported methods such as banding in cesium chloride gradients, as was used for the initial report of AAV vector expression in vivo (Flotte, et al. J. Biol. Chem. 268: 3781-3790, 1993) or chromatographic purification, as described in O'Riordan et al., WO97/08298. Methods for in vitro packaging AAV vectors are also available and have the advantage that there is no size limitation of the DNA packaged into the particles (see, U.S. Pat. No. 5,688,676, by Zhou et al., issued Nov. 18, 1997). This procedure involves the preparation of cell free packaging extracts.

D. Hybrid Adenovirus-AAV Vectors

Hybrid Adenovirus-AAV vectors have been generated and are typically represented by an adenovirus capsid containing a nucleic acid comprising a portion of an adenovirus, and 5' and 3' inverted terminal repeat sequences from an AAV which flank a selected transgene under the control of a promoter. See e.g. Wilson et al, International Patent Application Publication No. WO 96/13598. This hybrid vector is characterized by high titer transgene delivery to a host cell and the ability to stably integrate the transgene into the host cell chromosome in the presence of the rep gene. This virus is capable of infecting virtually all cell types (conferred by its adenovirus sequences) and stable long term transgene integration into the host cell genome (conferred by its AAV sequences).

The adenovirus nucleic acid sequences employed in this vector can range from a minimum sequence amount, which requires the use of a helper virus to produce the hybrid virus particle, to only selected deletions of adenovirus genes, which deleted gene products can be supplied in the hybrid viral process by a packaging cell. For example, a hybrid virus can comprise the 5' and 3' inverted terminal repeat (ITR) sequences of an adenovirus (which function as origins of replication). The left terminal sequence (5') sequence of the Ad5 genome that can be used spans bp 1 to about 360 of the conventional adenovirus genome (also referred to as map units 0-1) and includes the 5' ITR and the packaging/enhancer domain. The 3' adenovirus sequences of the hybrid virus include the right terminal 3' ITR sequence which is about 580 nucleotides (about bp 35,353—end of the adenovirus, referred to as about map units 98.4-100).

For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

E. Retroviruses

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33:153). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas and Rubenstein (1988) "Retroviral Vectors", In: Rodriguez and Denhardt ed. Vectors: A Survey of Molecular Cloning Vectors and their Uses. Stoneham:Butterworth; Temin, (1986) "Retrovirus Vectors for Gene Transfer: Efficient Integration into and Expression of Exogenous DNA in Vertebrate Cell Genome", In: Kucherlapati ed. Gene Transfer. New York: Plenum Press; Mann et al., 1983, supra). The media containing the recombinant retroviruses is then collected, optionally concentrated, and used for gene transfer. Retroviral vectors are able to infect a broad variety of cell types. Integration and stable expression require the division of host cells (Paskind et al. (1975) Virology 67:242). This aspect is particularly relevant for the treatment of PVR, since these vectors allow selective targeting of cells which proliferate, i.e., selective targeting of the cells in the epiretinal membrane, since these are the only ones proliferating in eyes of PVR subjects.

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a protein of the present invention, e.g., a transcriptional activator, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals. Examples of suitable retroviruses include pLJ, pZIP, pWE and pEM which are well known to those skilled in the art. A preferred retroviral vector is a pSR MSVtkNeo (Muller et al. (1991) Mol. Cell Biol. 11:1785 and pSR MSV(XbaI) (Sawyers et al. (1995) J. Exp. Med. 181: 307) and derivatives thereof. For example, the unique BamHI sites in both of these vectors can be removed by digesting the vectors with BamHI, filling in with Klenow and religating to produce pSMTN2 and pSMTX2, respectively, as described in PCT/US96/09948 by Clackson et al. Examples of suitable packaging virus lines for preparing both ecotropic and amphotropic retroviral systems include Crip, Cre, 2 and Am.

Retroviruses, including lentiviruses, have been used to introduce a variety of genes into many different cell types, including neural cells, epithelial cells, retinal cells, endothelial cells, lymphocytes, myoblasts, hepatocytes, bone marrow cells, in vitro and/or in vivo (see for example, review by Federico (1999) Curr. Opin. Biotechnol. 10:448; Eglitis et al., (1985) Science 230:1395-1398; Danos and Mulligan, (1988) PNAS USA 85:6460-6464; Wilson et al., (1988) PNAS USA 85:3014-3018; Armentano et al., (1990) PNAS USA 87:6141-6145; Huber et al., (1991) PNAS USA 88:8039-8043; Ferry et al., (1991) PNAS USA 88:8377-8381; Chowdhury et al., (1991) Science 254:1802-1805; van Beusechem et al., (1992) PNAS USA 89:7640-7644; Kay et al., (1992) Human Gene Therapy 3:641-647; Dai et al., (1992) PNAS USA 89:10892-10895; Hwu et al., (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079-9083; Julan et al., (1992) J. Gen Virol 73:3251-3255; and Goud et al., (1983) Virology 163:251-254); or coupling cell surface ligands to the viral env proteins (Neda et al., (1991) J. Biol. Chem. 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

F. Other Viral Systems

Other viral vector systems that can be used to deliver a polynucleotide of the invention have been derived from vaccinia virus, alphavirus, poxvirus, arena virus, polio virus, and the like. Such vectors offer several attractive features for various mammalian cells. (Ridgeway (1988) In: Rodriguez R L, Denhardt D T, ed. Vectors: A survey of molecular cloning vectors and their uses. Stoneham: Butterworth; Baichwal and Sugden (1986) In: Kucherlapati R, ed. Gene transfer. New York: Plenum Press; Coupar et al. (1988) Gene, 68:1-10; Walther and Stein (2000) Drugs 60:249-71; Timiryasova et al. (2001) J Gene Med 3:468-77; Schlesinger (2001) Expert Opin Biol Ther 1:177-91; Khromykh (2000) Curr Opin Mol Ther 2:555-69; Friedmann (1989) Science, 244:1275-1281; Ridgeway, 1988, supra; Baichwal and Sugden, 1986, supra; Coupar et al., 1988; Horwich et al. (1990) J. Virol., 64:642-650).

7. Transgenic Animals

While the techniques described herein may be used to deliver nucleic acids to human or animal subjects, other methods are available to generate non-human transgenic animals incorporating a recombinant nucleic acid encoding a contrast protein.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains such as C57BL/6 or DBA/1 may be selected. The line(s) used to practice this invention may themselves be transgenics, and/or may be knockouts (i.e., obtained from animals which have one or more genes partially or completely suppressed).

In one embodiment, the construct comprising a nucleic acid encoding a contrast protein is introduced into a single stage embryo. The zygote is the best target for microinjection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) PNAS 82:4438-4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents. Alternatively, MRI can be used to visualize transgene expression.

An alternative method for generating transgenic animals involves the in vivo or ex vivo (in vitro) transfection of male animal germ cells with a desired nucleic acid (see e.g., U.S. Pat. No. 6,316,692). In one approach, the nucleic acid is delivered in situ to the gonad of the animal (in vivo transfection). The transfected germ cells are allowed to differentiate in their own milieu, and then animals exhibiting integration of the nucleic acid into the germ cells are selected. The selected animals may be mated, or their sperm utilized for insemination or in vitro fertilization to produce transgenic progeny. The selection may take place after biopsy of one or both gonads, or after examination of the animal's ejaculate to confirm the incorporation of the desired nucleic acid sequence. Alternatively, male germ cells may be isolated from a donor animal and transfected, or genetically altered in vitro. Following this genetic manipulation, transfected germ cells are selected and transferred to the testis of a suitable recipient animal. Before transfer of the germ cells, the recipient testis are generally treated in one, or a combination, of a number of ways to inactivate or destroy endogenous germ cells, including by gamma irradiation, by chemical treatment, by means of infectious agents such as viruses, or by autoimmune depletion or by combinations thereof. This treatment facilitates the colonization of the recipient testis by the altered donor cells. Animals that carry suitably modified sperm cells may be allowed to mate naturally, or alternatively their spermatozoa are used for insemination or in vitro fertilization.

In an exemplary embodiment, a transgenic animal may be produced by in vitro infection of a single-cell embryo with a lentiviral vector. See e.g., Lois et al., Science 295: 868-872 (2002).

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A fourth type of target cell for transgene introduction is the embryonal stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83: 9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

In general, progeny of transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material encoding a contrast agent. Further, the sequence will preferably be attached to a regulatory sequence that allows the expression of the transgene. Contrast agent produced in situ may be visualized by MRI.

8. Methods and Compositions Relating to Plants

The methods and compositions described herein may be used in a variety of applications in plants, including for example, monitoring expression of a transgene of interest or for monitoring the effects of a plant's interaction with the environment or various test compounds. A plant may be contacted with a transgene of interest and a nucleic acid construct comprising the coding sequence for a contrast protein that is operably linked to a regulatory sequence. In various embodiments, the transgene may be provided as a transcriptional fusion with sequences encoding the contrast protein, the transgene and the contrast protein sequences may be provided separately on the same or different nucleic acid constructs, the transgene and the contrast protein sequences may be administered to the plant at the same or different times, the transgene and contrast protein sequences may be provided under the control of the same or different promoter sequences, etc. Based on the teachings herein, one of skill in the art will be able to utilize the appropriate compositions and methods for a desired result. In one embodiment, a plant may contacted with a transgene of interest and a nucleic acid construct comprising the coding sequence for a contrast protein that is operably linked to a regulatory sequence. MRI imaging may then be used to monitor the expression of the transgene to determine the timing and/or localization of expression of the transgene in the plant. In another embodiment, a plant may be transformed with a coding sequence for a contrast protein operably linked to a promoter for a gene of interest. The plant may then be exposed to different environmental conditions and/or contacted with one or more test compounds. MRI imaging may be used to monitor gene expression driven by the promoter because the level of contrast detected by MRI will correlate with, or be indicative of, the level of expression from the promoter. Any changes in the level of expression of the contrast protein will be useful in evaluating the effects of environmental conditions and/or test compounds on expression of genes controlled by the promoter.

Transgenes of interest may be reflective of the commercial markets and interests of those involved in the development of a crop, including, for example, genes encoding agronomic traits, insect resistance, disease resistance, herbicide resistance, sterility, grain characteristics, commercial products, genes involved in oil, starch, carbohydrate, or nutrient metabolism, genes affecting kernel size, sucrose loading, and the like, and genes involved in grain quality such as levels and types of oils, saturated and unsaturated, quality and quantity of essential amino acids, and levels of cellulose.

A variety of regulatory elements may be used to drive expression from a plant expression vectors. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224:838-843); or heat shock promoters, e.g., soybean hsp17.5-E or hsp17.3-B (Gurley et al., 1986, Mol. Cell. Biol. 6:559-565) may be used. These constructs can be introduced into plant cells using Ti plasmids, Ri plasmids, plant virus vectors, direct DNA transformation, biolistics/particle bombardment, microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9. As used herein, regulatory elements include but are not limited to inducible and non-inducible promoters, enhancers, operators and other elements known to those skilled in the art that drive and regulate expression.

In certain embodiments, the promoter may be capable of directing expression in a particular tissue of the plant and/or at particular stages of development of the plant, such as, for example, the CHS promoter, the PATATIN promoter, etc. The promoter may be heterologous or homologous to the plant. For example, the promoter may be able to direct expression to the fruit or leaves which is useful when trying to develop therapeutic agents to be delivered to humans through ingestion of the plant material. Alternatively, the promoter may direct expression to the endosperm of the plant seed or to the roots or tuber of the plant, such as, for example, the promoter from the high molecular weight glutenin (HMWG) gene of wheat. Other suitable promoters will be known to the skilled artisan, such as, for example, the promoters of gliadin, branching enzyme, ADPG pyrophosphorylase, starch synthase and actin. In still another embodiment, externally regulatable promoters may be used, such as, for example, promoters responsive to chemical exposure, temperature, or developmental signals.

In other embodiments, strong and non tissue- or developmental-specific plant promoters (e.g., a promoter that strongly expresses in many or all plant tissue types) may be used in accordance with the methods and compositions described herein. Examples of such strong, "constitutive" promoters include, but are not limited to, the CaMV 35S promoter (Odell et al., 1985, Nature 313:810-812), the T-DNA mannopine synthetase promoter, and their various derivatives. In another embodiment, an inducible or repressible promoter may be used, such as, for example, a tet operator promoter as described in Weinmann et al., 1994, Plant J. 5:559-569; or a glucocorticoid-inducible promoter as described in McNellis et al., 1998, Plant J. 14:247-257; or an ethanol inducible promoter as described in Caddick et al., 1998, Nature Biotechnology 16:177-180. See, also, Gatz, 1995, Methods in Cell Biology 50:411-424, which describes inducible and repressible gene expression systems for plants. For plastid transformation, strong promoters such as the promoter (PpsbA) of psbA, the plastid gene encoding the photosystem II 32 kD protein, may be used.

Plants and plant cells may be transformed using any method known in the art. In one embodiment, Agrobacterium is employed to introduce the gene construct into plants. Such transformation typically uses binary Agrobacterium T-DNA vectors (Bevan, 1984, Nuc. Acid Res. 12:8711-8721), and the co-cultivation procedure (Horsch et al., 1985, Science 227: 1229-1231). Generally, the Agrobacterium transformation system is used to engineer dicotyledonous plants (Bevan et al., 1982, Ann. Rev. Genet 16:357-384; Rogers et al., 1986, Methods Enzymol. 118:627-641). The Agrobacterium transformation system may also be used to transform, as well as transfer, DNA to monocotyledonous plants and plant cells. (see Hernalsteen et al., 1984, EMBO J 3:3039-3041; Hooykaas-Van Slogteren et al., 1984, Nature 311:763-764; Grimsley et al., 1987, Nature 325:1677-179; Boulton et al., 1989, Plant Mol. Biol. 12:31-40; and Gould et al., 1991, Plant Physiol. 95:426-434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, particle gun bombardment (biolistics), protoplast transformation through calcium-, polyethylene glycol (PEG)- or electroporation-mediated uptake of naked DNA (see Paszkowski et al., 1984, EMBO J 3:2717-2722, Potrykus et al., 1985, Molec. Gen. Genet. 199:169-177; Fromm et al., 1985, Proc. Nat. Acad. Sci. USA 82:5824-5828; and Shimamoto, 1989, Nature 338: 274-276) and electroporation of plant tissues (D'Halluin et al., 1992, Plant Cell 4:1495-1505). Additional methods for plant cell transformation include microinjection, silicon carbide mediated DNA uptake (Kaeppler et al., 1990, Plant Cell Reporter 9:415-418), and microprojectile bombardment (see Klein et al., 1988, Proc. Nat. Acad. Sci. USA 85:4305-4309; and Gordon-Kamm et al., 1990, Plant Cell 2:603-618). In various methods, selectable markers may be used, at least initially, in order to determine whether transformation has actually occurred. Useful selectable markers include enzymes which confer resistance to an antibiotic, such as gentamycin, hygromycin, kanamycin and the like. Alternatively, markers which provide a compound identifiable by a color change, such as GUS, or luminescence, such as luciferase, may be used. For plastid transformation, biolistics according the method of Svab and Maliga (Svab et al., 1993, Proc. Natl. Acad. Sci. USA 90: 913-917) is preferred. In an exemplary embodiment, MRI imaging may be used to detect expression of a contrast agent thereby selecting successfully transformed plants or plant cells.

The methods and compositions described herein may be practiced with any plant. Such plants include but are not limited to, monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*, tobacco).

9. MRI Methodologies

In general, contrast agents of the invention are designed for use in MRI detection systems. In the most common implementation of MRI, one observes the hydrogen nucleus (proton) in molecules of mobile water contained in subject materials. The subject material is placed in a large static magnetic field. The field tends to align the magnetic moment associated with the hydrogen nuclei in water along the field direction. The nuclei are perturbed from equilibrium by pulsed radiofrequency (RF) radiation set at the Larmor frequency, which is a characteristic frequency proportional to the magnetic field strength where protons resonantly absorb energy. Upon removing the RF, the nuclei induce a transient voltage in a receiver antenna; this transient voltage constitutes the nuclear magnetic resonance (NMR) signal. Spatial information is encoded in both the frequency and/or phase of the NMR signal by selective application of magnetic field gradients that are superimposed onto the large static field. The transient voltages are generally digitized, and then these signals may be processed by, for example, using a computer to yield images.

The invention now being generally described, it will be more readily understood by reference to the following examples, which are included merely for purposes of illustration of certain aspects and embodiments of the present invention, and are not intended to limit the invention.

EXAMPLES

Example 1

NMR of K562 Cells Over-Expressing Ferritin: Simulated Tumor Studies

We describe data showing the feasibility of using of an over-expression of intra-cellular metal-binding polypeptides as a potent MRI contrast agent. These initial results focus on ferritin in living human myeloid leukemia (K562) cells.

To investigate the sensitivity of ferritin in modulating the NMR properties of K562 cells, we synthesized simulated "tumor" samples. These consisted of K562 cells that were stimulated to produce varying amounts of excess intra-cellular ferritin in vitro. Cells were then suspended in low-melting point agarose to form small pellets. The spin-lattice relaxation rate ($1/T_1$) and the spin-spin relaxation rate ($1/T_2$) were measured in the pellets to quantify the impact of ferritin. (Modulation of these relaxation times give rise to image contrast in MRI.) In the same cells used for the samples, we assayed the total ferritin content using ELISA (Enzyme Linked Immuno-Sorbent Assay).

For the experiment, samples consisted of K562 cells that were stimulated to over-express ferritin by a 16 hour incubation with varying concentrations of ferric ammonium citrate (FAC) in RPMI culture media supplemented with 2% fetal calf serum. After incubation, cells were washed. For each FAC concentration, $10^7$ cells were counted for the NMR sample and $10^6$ cells we set aside for the ELISA assay (Alpha Diagnostics Int. Inc., San Antonio, Tex.)). Cells used for the NMR samples were re-suspended in 50 µl of low melting point agarose in a small plastic tube. The $1/T_1$ and $1/T_2$ measurements were performed at room temperature using a Bruker Minispec relaxometer (Bruker Instruments, Billerica, Mass.). Cells used for the ELISA were treated with lysis buffer and the consistency of the total amount of released protein was confirmed using a bicinchoninic acid protein quantitation assay (Pierce Inc., Rockford, Ill.). Ferritin concentration was calculated as an average over the cell pellet volume.

The correlation between the NMR changes and ferritin content is shown in FIG. 1. The results show substantial changes in the relaxation times with modest increases in ferritin expression over background; these changes are easily observed using MRI (below). These simulated tumors have a cell density of 200 cells/nl.

Example 2

Toxicity Studies

Figure 2:
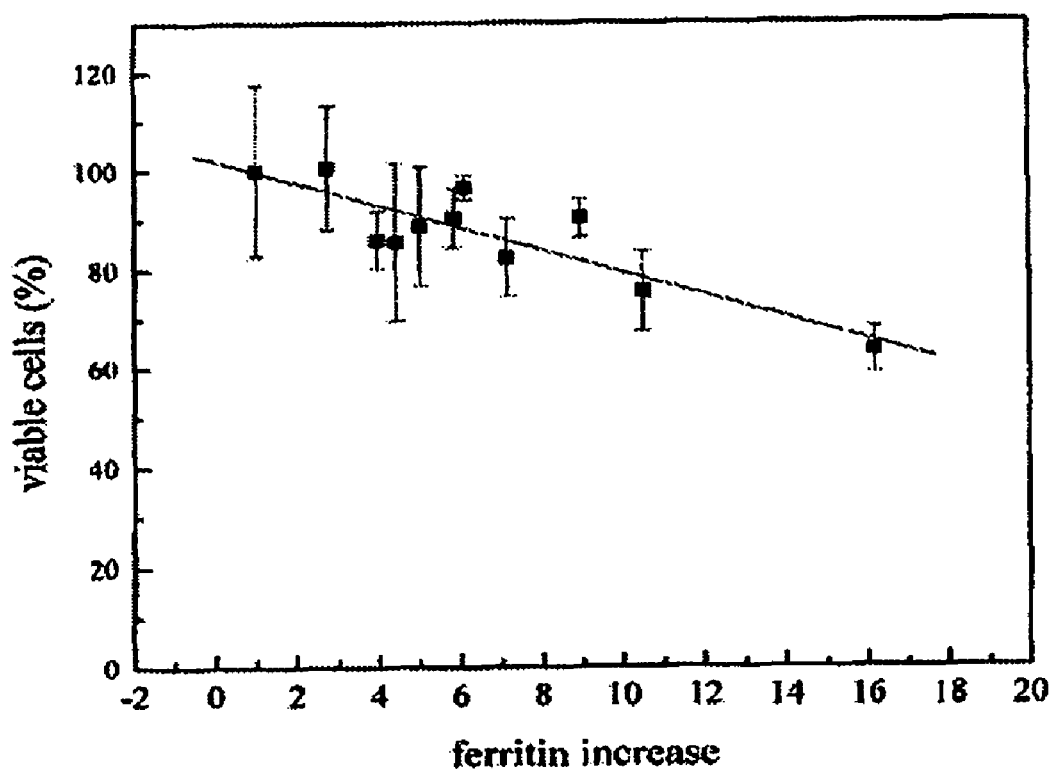
FIG. 2. Data showing the percent of the total number cells remaining after the 16 hour period of ferritin loading. For each FAC concentration (and control), cells before and after the incubation period were counted 3-times using a hemocytometer and the results were averaged. The error bars represent the standard deviation for the separate (N=4) incubation experiments.

The ferritin synthesis temporarily perturbs the cell's iron metabolism. Although the adverse effects of this on the cell's long-term health have yet to be fully determined in vivo, indications from various in vitro experiments have shown that ferritin overexpression is not harmful in a variety of cell lines, especially for transient expression. This was confirmed in our experiments in K562 cells described in Example 1 above. For each FAC concentration (and control), cells before and after the incubation period were counted 3-times using a hemocytometer and the results were averaged. FIG. 2 shows the percent cells remaining after the 16 hour period of ferritin loading. In the simulated tumors, ferritin increases of greater than 10-times over baseline levels only resulted in a cell loss of order 20%. The ferritin increase required to provide observable MRI contrast is only of order 2-4.

Example 3

MRI of Simulated Tumors

Figure 3:
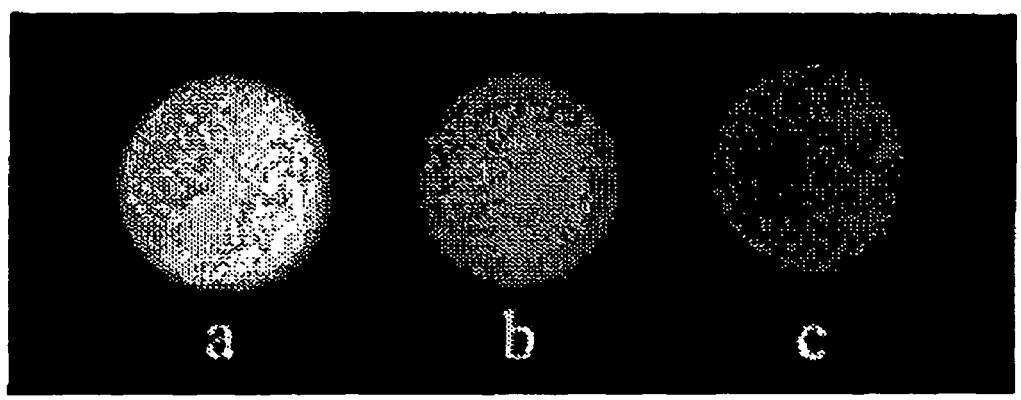
FIG. 3. MRI image of three simulated tumor samples. Here, (a) is the control and (b) and (c) are the samples containing a ferritin increase of 2.7 and 4, respectively. Contrast among these samples is readily apparent in this $T_2$-weighted image. Images were acquired simultaneously using a Bruker 7-Tesla MRI system with TE/TR=45/2000 ms, 128×128 image points, and a 1 mm-thick slice. The pellet size was approximately 4 mm in diameter.

Ferritin over-expression in the simulated tumors is readily visualized using MRI. FIG. 3 shows a M image slice through three pellets used in the NMR experiments. In this image, contrast is predominately $T_2$-weighted. In FIG. 3, (a) is the control, and (b)-(c) are the samples containing a ferritin increase of 2.7 and 4, respectively (see FIG. 1). Images were acquired simultaneously using a Bruker 7-Tesla MRI system with TE/TR=45/2000 ms, 128×128 image points, and a 1 mm-thick slice. The pellet size was approximately 4 mm in diameter.

Example 4

MRI Studies of Cells Comprising Recombinant Ferritin

Figure 4:
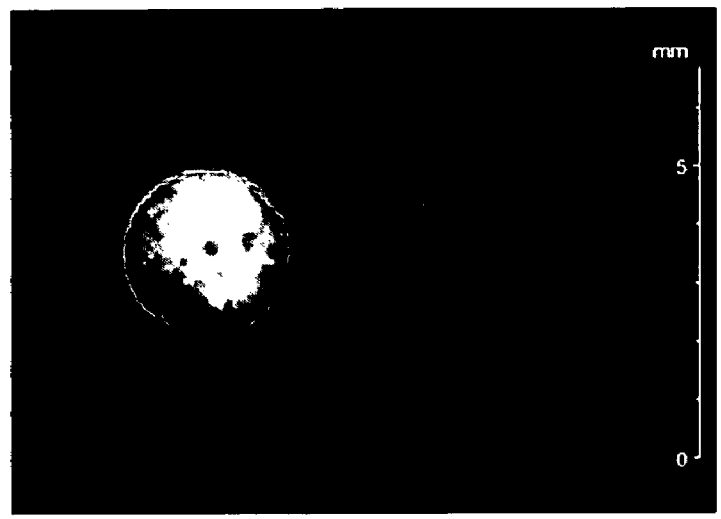
FIG. 4. MRI image through pelleted 9 L glioma cells transfected with contrast proteins light (LF) and heavy (HF) chain ferritin. The sample on the left is the control (no DNA added during incubation). Image contrast is readily apparent between the two pellets. Expression of the reporter turns cells dark in the MR image. This image was acquired using an 11.7 Tesla MRI system with a standard $T_2$-weighted 2 DFT pulse sequence. This image was acquired at 4° C.
Figure 5:
FIG. 5. MRI image through pelleted 9 L cells infected with contrast proteins light (LF) and heavy (HF) chain ferritin via an adenovirus. The sample on the left is the control (uninfected cells). Image contrast is readily apparent between the two pellets. (Note that the intense dark spots in the pellets are bubble artifacts.) This image was acquired using an 11.7 Tesla MRI system and a standard $T_2$-weighted 2 DFT pulse sequence. This image was acquired at 4° C.

Both the light and heavy ferritin transgenes, denoted LF and HF, respectively, were introduced into variety of cell lines (e.g. K562 and Rat 9 L gliosarcoma) using lipid-based transfection methods and by using viruses. The results were analyzed using ELISA, NMR, and MRI. Typical results are shown in FIGS. 4 and 5. Human light and heavy chain ferritin cDNA having defective iron regulatory elements were used. Using standard molecular biology techniques both transgenes were placed under the control of the immediate early promoter of the CMV. The integrity of the transgenes was confirmed by electrophoresis of DNA fragments following digestion with various restriction enzymes and by DNA sequencing.

Introduction of Ferritin Via Transfection

9 L cells (Fischer 344 rat gliosarcoma) were incubated in DMEM supplemented with 10% fetal bovine serum (FBS), penicillin, streptomycin, and glutamine. Cells were plated in 24-well plates one day before transfection to achieve 60-80% confluence. The cells were rinsed with serum-free DMEM and then covered with the same solution. A DNA mixture was prepared as follows. The reagent Lipofectamine™ (Invitrogen, Carlsbad, Calif.) was combined with equal amounts of LF and HF DNA in serum-free DMEM. The reagent Plus™ (Invitrogen, Carlsbad, Calif.) was added to the DNA solution to increase transfection efficiency. The DNA mixture was added to the cells, and then incubated for 3 hours at 37° C., after which DMEM containing 10% FBS was added. Cells were collected 48 or 96 hours post-transfection and counted. In addition, control samples were prepared by incubating 9 L cells under identical conditions as above, except that no DNA was added to the Lipofectamine™—Plus™—DMEM mixture. Upon harvesting after 48 or 96 hours no significant differences in cell numbers were observed between samples incubated with the DNA reporters and the control samples. Thus, there was no apparent toxicity associated with the contrast proteins.

To assay the ferritin increase after transfection, 9 L cells were prepared as described above. The intracellular proteins were extracted using the M-PER™ extraction Reagent (Pierce Biotechnology, Mountain View, Calif.) and the ferritin content was assayed using an ELISA kit (Alpha diagnostics, San Antonio, Tex.). The results typically showed a ferritin concentration ~3 ng/ml in the transfected cells and a negligible (~0.0 ng/ml) amount of human ferritin in the non-transfected cells. (The 9 L cell line is from rat, and the antibody used in the ELISA detects only human ferritin with no cross-reactivity.)

The intracellular iron content was measured in transfected and control cells to confirm an increased iron-uptake with transgene expression. For these experiments 20×$10^6$ cells were plated and transfected using the methods described above. Control cells were also prepared as described above with no DNA added to the incubation solution. Cells were collected 96 hours post transfection and counted. Using standard methods [2001 Blood 97(9), 2863] cells were washed in PBS, and pellets were dissolved in an acid solution and treated with a batophenantroline sulconate solution. The light absorption of the solution was read at 535 nm using a spectrophotometer and the iron concentration was calculated. The results indicate a factor of ~1.5 increase in the net iron content of the transfected cells compared control.

Measurement of $1/T_2$ in pellets of transfected cells was performed. Cells ($20 \times 10^6$) were transfected with the transgenes as described above. Cells were collected 96 hours post-transfection, washed twice with PBS, and transferred to a 0.2 ml micro-centrifuge tubes. Cells were again centrifuged and the supernatant discarded. NMR measurements were performed on the pellets at 4° C. using a 20 MHz Bruker Minispec NMR analyzer (Bruker Instruments, Billerica, Mass.). The results typically show a factor of 15% increase in $1/T_2$ in the transfected cells over control.

Using the same cell pellets that were prepared for the above NMR experiments, we confirmed that the $1/T_2$ changes due to the expression of the contrast proteins provided satisfactory contrast in MR images. The micro-centrifuge tubes containing the pellets were placed in an MRI apparatus and imaged using a standard $T_2$-weighted two-dimensional Fourier transform (2 DFT) spin-echo pulse sequence. FIG. 4 displays typical data and shows a high-resolution MRI slice through two pellets acquired simultaneously; the left pellet is the control and the pellet on the right contains cells expressing the contrast proteins. Image contrast is clearly apparent between the two samples.

Introduction of Ferritin Via a Viral Vector

Contrast proteins have also been introduced into cells via a viral vector. Infected cells were characterized using ELISA, NMR, and MRI. The MRI data shows distinct contrast between cells infected with the contrast proteins and uninfected (control) cells. For these experiments the LF and HF transgenes were each incorporated into separate replication defective adenoviruses. These viruses were constructed using the commercially available Adeno-X™ expression system (Clontech, Palo Alto, Calif.) following the manufacture's instructions. The transgene expression was controlled using the CMV promoter. A HEK-293 cell line was used for production of viral stocks. When the cytopathic effect was evident in the HEK-293 cells due to viral production, cells were collected, lysed, and the supernatants were collected. These supernatants are adenovirus-rich and were used to infect mammalian cells to demonstrate MRI contrasting effects. 9 L cells were incubated in DMEM supplemented with 10% FBS, penicillin, streptomycin, and glutamine. Cells (~$20 \times 10^6$) were plated in 24-well plates one day before infection to achieve 60-80% confluence. The cells were then rinsed with serum-free DMEM and then covered with the same solution. Equal volumes of both the LF and HF adenovirus from each of the respective supernatants were added to the 9 L cells. The virus and cells were incubated in serum-free media for 0.5 hour, and then FBS was added to the DMEM to give 10% FBS. After a 48 hours incubation the cells were harvested, rinsed, and the effects of the contrast genes were assayed. FIG. 5 shows typical MRI data of two pellets, infected and uninfected (control), 9 L cells. These data were acquired using a $T_2$-weighted 2 DFT spin-echo sequence in a similar manner as the transfection experiments above. The left pellet is the control and the right pellet contains cells infected with LF and HF transgenes. Image contrast is clearly apparent between the two samples.

Example 5

Introduction of a Nucleic Acid Encoding a Contrast Protein In Vivo

This experiment is designed to demonstrate the delivery of contrast agent of the invention in vivo.

In this example, two tumor samples are transplanted onto a nude mouse. An HSV delivery is engineered to contain a nucleic acid construct comprising the coding sequences for the human ferritins represented in SEQ ID Nos: 2 and 4. One tumor sample is injected with the HSV+ferritin vector, while the other tumor sample is injected with an "empty" HSV vector. The mouse is subjected to MRI, and the contrast between the HSV+ferritin sample and the "empty" HSV sample is compared.

Example 6

In Vivo Imaging Studies

In this example we present a novel approach that uses MRI to visualize transgene expression in vivo via a gene transfer vector encoding a ferritin marker gene. This approach yields robust image contrast and is widely applicable to mammalian systems. Due to the crystalline ferrihydrite core, FT has an anomalously-high superparamagnetism (Bulte, J. W. et al. *J. Magn. Reson. Imaging* 4, 497-505 (1994)) and a marked effect on solvent NMR relaxation rates (Bulte, J. W. et al. *J. Magn. Reson. Imaging* 4, 497-505 (1994); Gottesfeld, Z. et al. T. *Magn. Reson. Med.* 35, 514-20 (1996); Vymazal, J., et al. *Magn. Reson. Med.* 36, 61-65 (1996); Vymazal, J., et al. *J. Inorg. Biochem.* 71, 153-157 (1998)). Thus, FT is an ideal molecule to express for in vivo MRI studies. In this example we introduced an MRI reporter gene coding for metalloproteins from the FT family into specific tissues of a living subject using a replication-defective adenovirus (AdV). The vector encoded reporter is made superparamagnetic as the cell sequesters endogenous Fe from the organism. No exogenously-provided, bulky-metal complex is required, thereby simplifying intracellular delivery.

We initially characterized the biological effects of reporter expression in a series of in vitro assays. For in vivo experiments, we delivered the AdV-ferritin vector (AdV-FT) into the brain of C57B1/6J mice via stereotaxic injection. The virus-transduced neurons and glia displayed robust image contrast. We longitudinally monitored the contrast enhancement for up to 5 weeks, the endpoint of our study. A lacZ expressing AdV control vector (AdV-lacZ) injected into the contralateral side showed no MRI contrast, but histology revealed a similar transduction pattern as the AdV-FT vector. Moreover, immunohistochemical detection of the FT transgenes corroborated the pattern shown by MRI.

Overall, this technology can be adapted to examine gene expression in many tissue types, therefore an immense number of preclinical in vivo applications exist. Examples include preclinical testing of gene therapeutics to assess dosage protocols and visualizing gene expression in transgenic animals.

Results

In Vitro Studies

Figure 28:
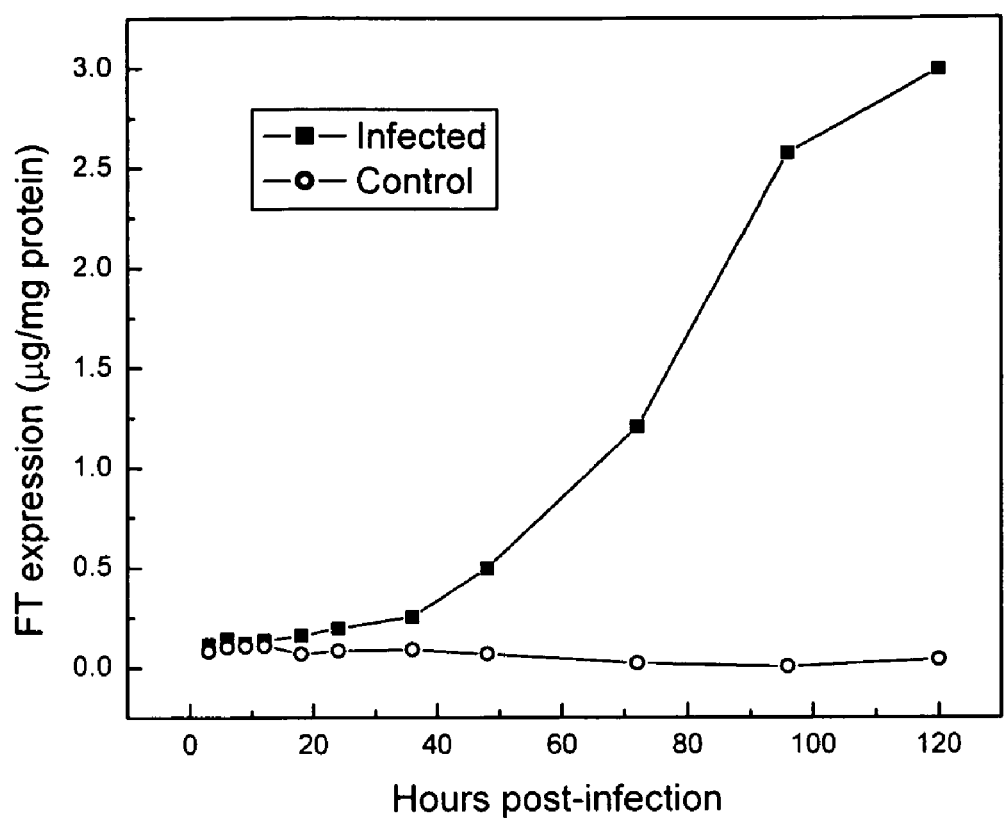
FIG. 28. Time course of AdV-FT expression in A549 cells. Intracellular LF content was measured by ELISA (μg per mg of total protein) in control (open circles) and vector-transduced cells (closed squares). Values are the mean for n=3, and the standard error of the mean (SEM) is within the data symbols.

To investigate the function, cytotoxicity, and MRI-efficacy of the AdV-FT reporter, we conducted in vitro studies using a common cell line (A549). We transduced the cells with two separate AdV vectors containing transgenes for the light and heavy FT subunits (AdV-LF and AdV-HF, respectively). The ratio of the two vectors was 1:1, with a total multiplicity of infection (MOI) of 100. We first characterized the reporter expression kinetics in vitro in A549 cells. After transduction, we collected the intracellular proteins at various time points and determined the FT content by ELISA. The FT production showed a time course of gene expression consistent with known CMV promoter activity (FIG. 28). AdV-FT transduced cells showed detectable transgene expression at 18 hours post-transduction, and by 120 hours transgene expression was ~60 times higher than background FT levels (FIG. 28).

Figure 29:
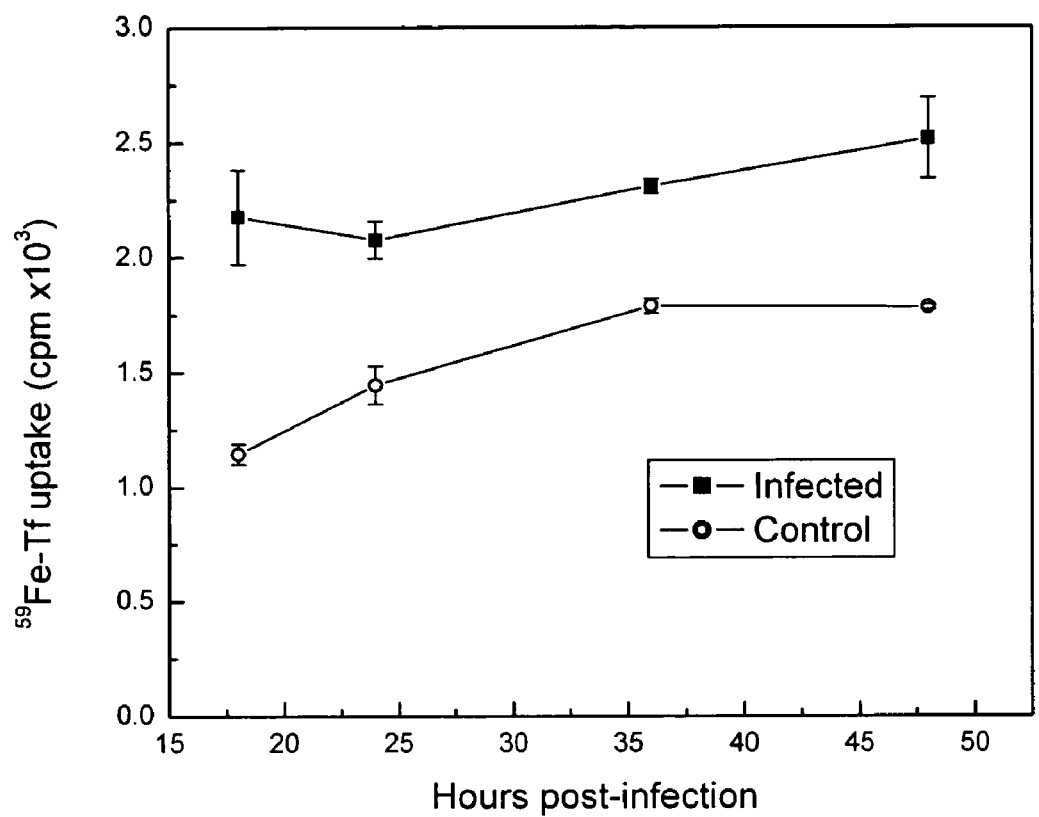
FIG. 29. In vitro uptake kinetics of $^{59}$Fe-enriched human transferrin in A549 cells. Cells were transduced with AdV-LF and AdV-HF. $^{59}$Fe-enriched holo-transferrin was added to the medium at various time points, and $^{59}$Fe uptake was assayed by scintillation. The transduced cells consistently show increased counts per minute (cpm) over controls by ~51%. Additionally, both transduced and control cells display a similar monotonic increase in Fe uptake over time. This observation is consistent with a steady increase in cell number in culture that is not impaired by reporter transduction or the transgene expression, which suggests that the vector-mediated expression of FT and iron sequestration is not overtly toxic to A549 cells in vitro. Data shown are the mean±SEM for n=3.

FT over-expression should trigger an increase in the cell's ability to internalize and store Fe. At various time points post-transduction, we tested this by adding $^{59}$Fe-enriched transferrin to the cultured cells for one hour in serum-free medium. After washing and lysing the cells we assayed $^{59}$Fe uptake. The transduced cells consistently showed an increased counts per minute over controls by ~50%, indicative of greater iron uptake and storage capacity (FIG. 29).

Figure 30:
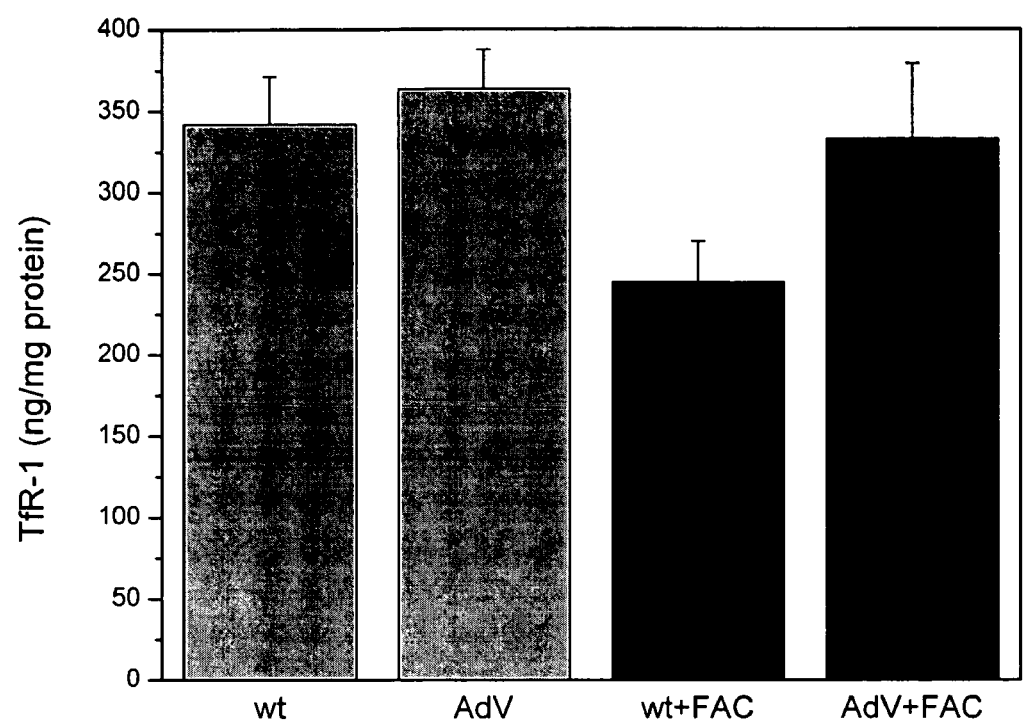
FIG. 30. TfR-1 levels in AdV-FT transduced and control A549 cells. ELISA was used to measure TfR-1 levels in cells at 120 hours post-transduction (AdV) and in non-transduced control (wt) cells. Results are shown without and with FAC supplementation (gray and black bars, respectively). Shown are mean values±SEM for n=3. A small increase in TfR-1 (~6%) is observed in transduced cells that had been incubated in low-iron medium (i.e. containing 2% FBS), although this is within the standard error of the mean. When FAC is added, a statistically significant increase (~36%) in TfR-1 levels is observed. These data suggest that with FAC supplementation the increase in the LIP is buffered by the extra Fe storage capacity provided by the up regulation of FT and thus does not impact TfR-1 expression. In the control, with low endogenous FT levels, the LIP is increased and TfR-1 is down regulated.

FT and transferrin receptor production is tightly regulated in response to the labile iron pool (LIP) level. Thus, it is expected that FT over-expression will increase Fe storage capacity and reduce the LIP, which in turn would lead to an upregulation of transferrin receptor (Welch, S. Transferrin: The Iron Carrier (CRC Press, Boca Raton, Fla., 1992)). To test whether the reporter could induce these effects, we assayed the transferrin receptor-1 (TfR-1) levels in transduced and control (i.e. mock-transduced) cells by ELISA. We observed a statistically significant increase, ~36%, in TfR-1 levels in transduced cells compared to control cells (FIG. 30) in the presence of iron supplement (ferric ammonium citrate, FAC).

Figure 31:
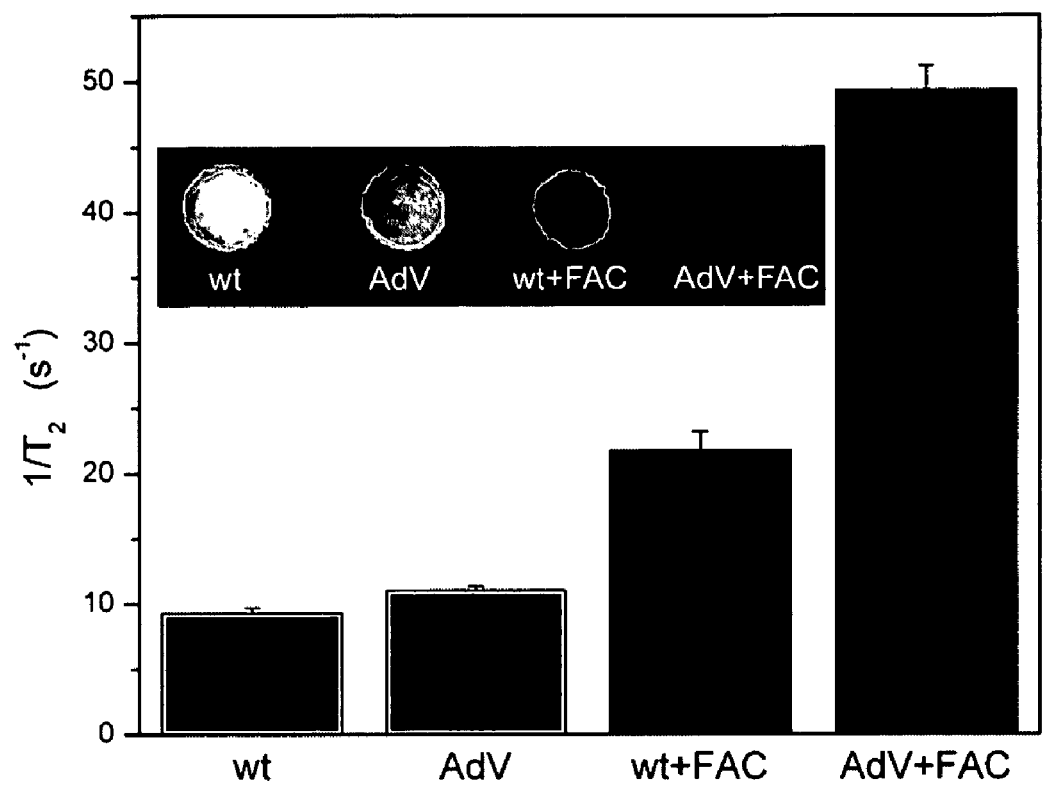
FIG. 31. In vitro $1/T_2$ in pelleted A549 cells. Results for AdV-FT transduced cells (AdV) 120 hours post-transduction and non-transduced control cells (wt) both with and without FAC supplementation (black and gray bars, respectively) are shown. The NMR results are the mean±SEM for n=3. The inset shows a $T_2$-weighted MR image of representative A549 pellets from the four experimental groups.

The impact of reporter expression on the spin-spin NMR relaxation rate ($1/T_2$) is a function of both the intracellular FT concentration and the amount of Fe loaded into the FT cores (Vymazal, J., et al. Magn. Reson. Med. 36, 61-65 (1996)). To detect relative Fe loading in transduced cells in vitro, we measured $1/T_2$ in pelleted A549 cells at 120 hours post-transduction. Transduced cells incubated with 2% FBS as the only Fe source showed only a minimal increase in $1/T_2$ compared to the control cells (FIG. 31). Incubating cells with an Fe supplement (FAC) significantly enhanced $1/T_2$ by approximately 2.5-fold in transduced compared to control cells (FIG. 31). This $1/T_2$ behavior is consistent with a scenario where FT shells are abundant following transduction (FIG. 28), but only minimally loaded with paramagnetic Fe. There is 'excess' Fe storage capacity inside the FT that cannot be filled under low Fe (i.e. FAC-negative) conditions. We also measured the spin-lattice relaxation rate ($1/T_1$), but it showed no statistically significant differences across all samples.

By performing $T_2$-weighted MRI on the pellets, we confirmed that the $1/T_2$ changes due to FT transgene expression correlate with detectable image contrast (FIG. 31, inset). Contrast is easily discernable between transduced and control cells incubated in FAC, but not for cells incubated in low-Fe conditions (FIG. 31, inset). Thus, the MRI is in qualitative agreement with the $1/T_2$ NMR measurements.

Figure 32:
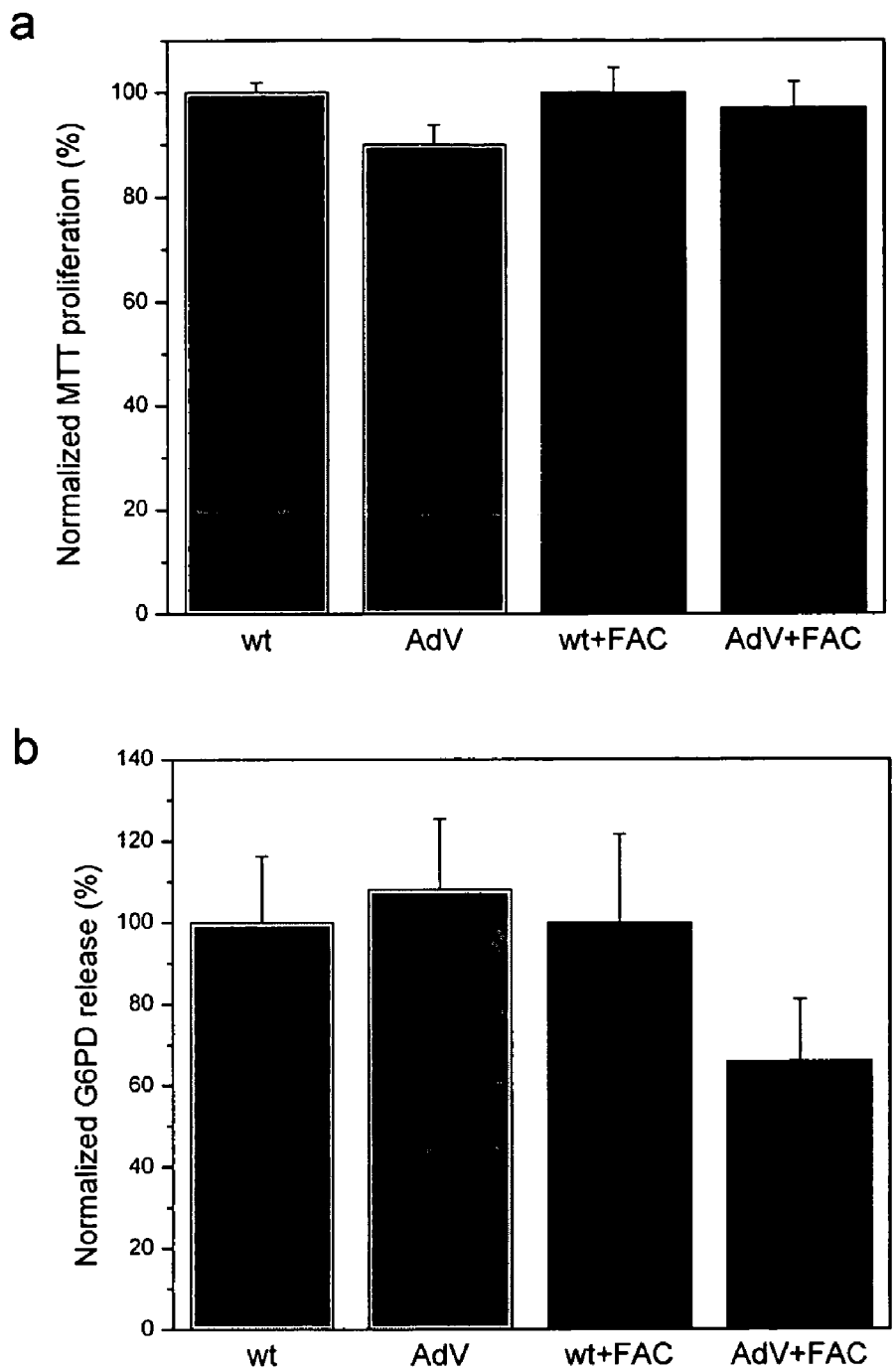
FIG. 32. In vitro cytotoxicity assays in A549 cells show no adverse effects due to AdV-FT expression. Data for AdV transduced cells and control cells (wt) are shown, both with and without FAC supplementation (black and gray bars, respectively). a, MTT proliferation assay. b, G6PD cytotoxicity assay. In b, data are normalized to wt, defined as 100%; higher G6PD release indicates increased toxicity. Values are mean±SEM for n=8.

Next we examined whether FT transgene expression could be detrimental to cell viability. To investigate cellular proliferation, we used a methyl thiazole tetrazolium (MTT) assay that measures mitochondrial activity. AdV-FT-transduced and control cells showed no statistically significant difference in viability at 48 hours post-transduction (FIG. 32a). Thus, FT transgene expression did not appear to impair cell proliferation, even in the presence of FAC (FIG. 32a).

We also measured potential cytotoxicity caused by FT vector transduction by assaying the release of the enzyme glucose-6 phosphate dehydrogenase (G6PD) into the medium. We observed no significant increase in enzyme release (i.e., toxicity) in the FT-transduced cells compared to control cells after 48 hours in the absence of FAC (FIG. 32b). Interestingly, with the Fe supplement the AdV-FT-transduced cells showed a small significant decrease in toxicity (by 34%) compared to control cells suggesting a protective role of FT over-expression. Overall, A549 cells showed no overt viability changes due to reporter expression.

In Vivo Studies

Figure 33:
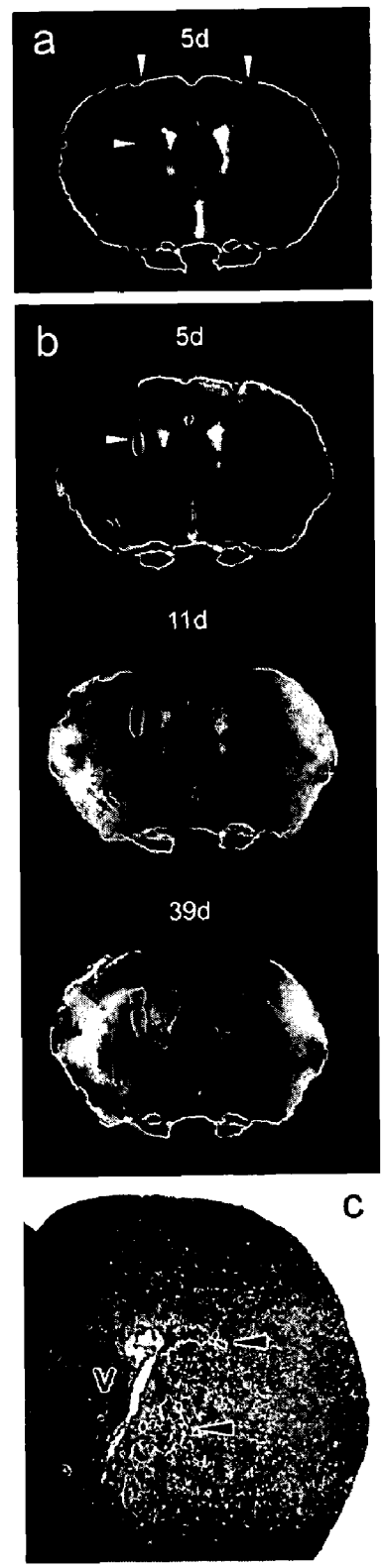
FIG. 33. In vivo longitudinal results of MRI reporter expression in the mouse brain. Adenovirus containing the MRI reporter was inoculated into the striatum. a, $T_2$-weighted image 5 days post-injection showing the inoculated sites (arrows, MRI reporter left, AdV-lacZ control right). b, Time-lapse $T_2$*-weighted images in the same mouse at day 5, 11, and 39 post-injection. c, X-gal stained AdV-lacZ transduction pattern at 5 days post-inoculation. In c, the staining pattern, similar to the MRI, is predominately in white matter (top arrow) and striatum (bottom arrow), where v denotes ventricle. Images were acquired at 11.7 T with a 0.75 mm slice thickness and an in-plane resolution of 102 μm.

To evaluate the true potential of this transgene imaging approach in vivo, we visualized MRI reporter expression in the mouse brain. We injected adenovirus containing the MRI reporter stereotactically into the striatum and then imaged the mice (n=5) at 5, 11, and 39 days post-inoculation. After 5 days, transduced cells displayed robust contrast in both $T_2$- and $T_2^*$-weighted images (left arrows, FIG. 33a, b). We calculated the contrast-to-noise ratio (CNR) from the mean intensities of 24 voxels in hypointense MRI reporter transduced regions and in nearby unaffected parenchyma. We obtained a CNR enhancement at 5 days post-inoculation of 6.6±1.7 and 16.2±1.6 in $T_2$- and $T_2^*$-weighted images, respectively. The uncertainty represents the standard error of the mean for n=5. The transduced cells were highly localized within a single 0.75 mm-thick slice. We did not detect any statistically significant MRI contrast on the contralateral side injected with the AdV-lacZ control vector (right arrows, FIG. 33). The MRI showed no visible signs of tissue damage, inflammation, or hematoma at the injection sites (FIG. 33a-b). Image contrast from the MRI reporter persisted for all time points measured (FIG. 33b), consistent with CMV promoter activity.

Figure 34:
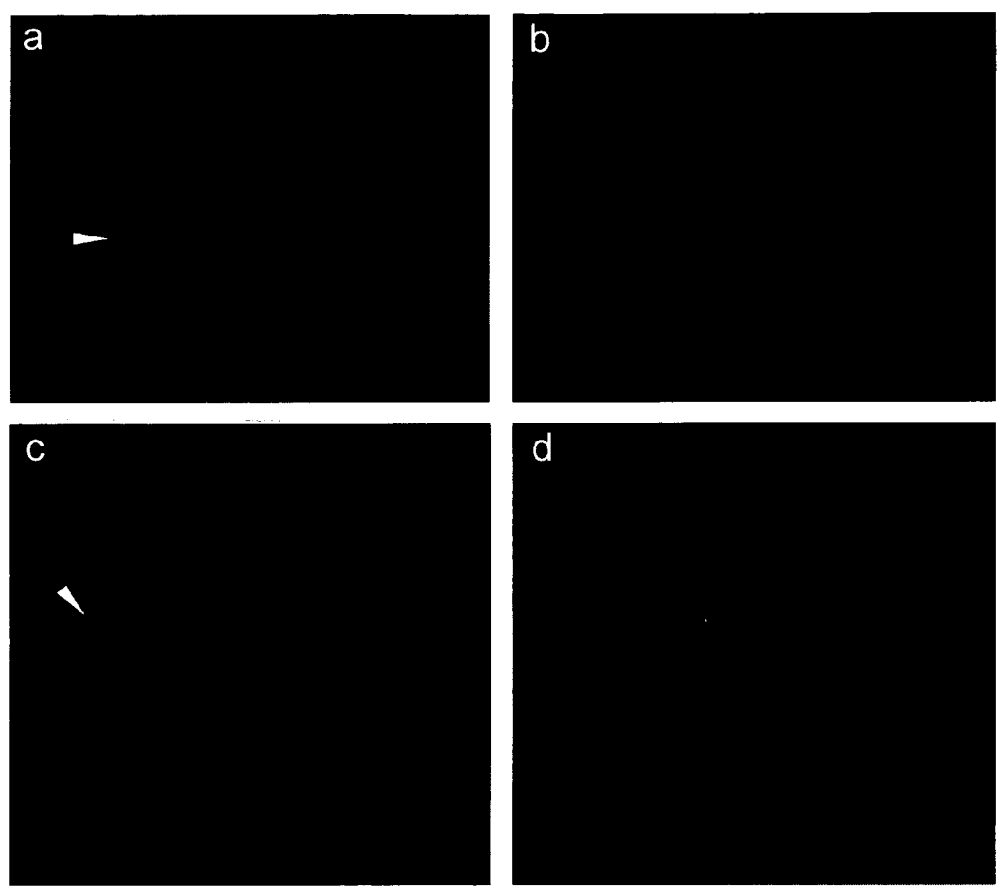
FIG. 34. Immunohistochemistry results showing FT expression in mouse brain. Adenovirus containing the MRI reporter was inoculated into the left striatum, and AdV-lacZ was injected into the contralateral side. Immunohistochemistry using antibodies for human LF and HF detected MRI reporter expression in the left striatum only (arrow) at 24 hours post-transduction for (a) HF and (b) LF. MRI reporter expression was increased by 5 days post-transduction (arrow) using antibodies for (c) HF and (d) LF. Panel pairs a-b and c-d are adjacent slices, and each pair is from a different mouse.

At 5 days post-transduction, we performed histology in selected brains. The X-gal staining pattern of the AdV-lacZ inoculation mimicked the AdV-FT-induced MRI contrast (FIG. 33c). We also performed immunohistochemistry to detect vector-mediated LF and HF ferritin subunit expression in the striatum at 1 and 5 days post-inoculation (FIG. 34). Both human HF (FIG. 34a,c) and LF (FIG. 34b,d) gene products were detected proximal to the inoculation site. Expression levels increased from 1 to 5 days in the inoculated regions (FIG. 34). The temporal/spatial pattern of recombinant protein expression was consistent with the MRI. At 1 day post-inoculation the MRI reporter contrast was minimal, however by day 5 the contrast was robust (FIG. 33). At 39 days post inoculation, we examined the cell specific markers GFAP (glial fibrillary acidic protein) and neurofilament by immunohistochemistry to assess for neuronal damage or gliosis caused by the MRI reporter expression. The GFAP and neurofilament stained sections showed no anomalous astrocyte proliferation or cell loss in regions of MRI reporter expression compared to the contralateral regions inoculated with AdV-lacZ.

Methods

Cell Culture. Human lung adenocarcinoma (A549) cells (ATCC #CCL185, Manassas, Va.) were cultured according to the vendor's specifications (except where noted). For experiments requiring Fe supplementation, 2 μmol of FAC with 16.5% iron content (Sigma, St. Louis, Mo.) was added 24 or 96 hours post-transduction and cultured for an additional 24 hours.

Expression Vectors. cDNAs encoding the human HF and LF were obtained from Paolo Arosio, Universita di Brescia, Italy. These cDNAs were devoid of the iron-response elements (Cozzi, A. et al. J. Biol. Chem. 275, 25122-25129 (2000)). Adenoviruses were generated using the Adeno-X expression system (Clontech, Palo Alto, Calif.) according to the manufacturer's instructions. Separate viral stocks were constructed for the HF, LF, and lacZ transgenes. All transgenes were under the control of the CMV immediate-early promoter. Titers were determined via endpoint dilution assays on A549 cells.

ELISA. To assay the time course of FT expression, A549 cells ($1\times10^6$) were transduced in serum-free DMEM at 50 MOI each for AdV-LF and AdV-HF. Cells were then incubated in DMEM supplemented with 2% FBS and harvested at various times post-transduction; extracts were evaluated for overall protein content by the BCA method (Pierce, Rockford, Ill.) and for LF content using an ELISA (ICN, Orangeburg, N.Y.). To assay transferrin receptor-1 (TfR-1) levels, $10^6$ A549 cells were transduced as described above and incubated in DMEM with 2% FBS for 120 hours. Membrane proteins were extracted, quantified, and the TfR-1 content was analyzed by ELISA (Ramco Labs Inc, Stafford, Tex.).

$^{59}$Fe Uptake. A549 cells were transduced as outlined above and then cultured in DMEM with 2% FBS. At various time points post-transduction cells were incubated with $^{59}$Fe-enriched human transferring (Klausner, R. D. et al. *J. Biol. Chem.* 258, 4715-24. (1983)). Radiolabeled cells were then washed, lysed, and cellular $^{59}$Fe was measured (n=3) by scintillation.

In Vitro NMR/MRI. NMR relaxation times $T_1$ and $T_2$ were used as a relative measure of Fe uptake. A549 ($3 \times 10^6$) cells were transduced as described above. Cells were then incubated for 120 hours in DMEM containing 2% FBS with or without FAC supplement. For supplemented cells, FAC was added at 96 hours. Cells were washed, fixed, pelleted, and the supernatant discarded. The $T_1$ and $T_2$ were measured for n=3 pellets from each experimental group at 30° C. using a 500 MHz NMR spectrometer (Bruker Instruments, Billerica, Mass.). After NMR, four representative samples were imaged simultaneously using an 11.7 T Bruker micro-imaging system. A $T_2$-weighted spin-echo sequence was used with TR/TE=3000/55 ms, 117 μm in-plane resolution, and a 0.75 mm-thick slice thickness.

Cell Viability. A549 cells ($2 \times 10^3$ cells/well) were transduced as described above and incubated in DMEM containing 2% FBS. FAC was added to a subset of the wells after 24 hours. At 48 hours post-transduction, the MTT assay was performed according to the vendor's specifications (ATCC). To assay cytotoxicity, cells were transduced as described above. At 48 hours post-transduction, cytotoxicity was measured by detecting glucose-6-phosphate dehydrogenase (G6PD) released into the medium according to the manufacturer's instructions (Molecular Probes Inc., Eugene, Oreg.). For both the MTT and G6PD assays n=8 wells were measured per condition.

In Vivo Studies. Experiments were performed in accordance with the Carnegie Mellon Institutional Animal Care and Use Committee (IACUC) guidelines and the National Institutes of Health Guide for the Care and Use of Laboratory Animals. Adult 20 g female C57B1/6J mice (Harlan, Indianapolis, Ind.) were anesthetized using an intraperitoneal cocktail of ketamine/xylazine and placed in a head stereotaxic device. Animals were injected with a 1:1 mixture of AdV-HF and AdV-LF ($1.6 \times 10^9$ pfu total) in the right striatum with a 32-gauge needle. The AdV-lacZ control vector was injected into the contralateral hemisphere. Animals were monitored until recovered and housed with food and water ad libitum. Mice were imaged longitudinally 5, 11, and 39 days post-injection. Images were acquired on anesthetized mice in an 11.7 T, 89 mm vertical-bore Bruker micro-imaging system. Coronal slices were acquired at the injection site using $T_2$-weighted spin-echo (SE) and $T_2^*$-weighted gradient-echo (GE) sequences. The parameters were TR/TE=1200/35 ms and TR/TE=1200/6.7 ms for the SE and GE sequences, respectively. All images were acquired with 256×256 image points, a 2.6 cm field of view, and a 0.75 mm slice thickness. The in-plane resolution was 98 μm. A total of n=5 mice were used.

Histology/Immunohistochemistry. Five days after adenoviral injection selected mice were sacrificed, and the brains were cryostat sectioned at a thickness of 14 μm and processed by X-gal staining according to the manufacturer's instructions (Sigma). For human LF and HF immunostaining, at 1 and 5 days post-injection mice were sacrificed and the brains were cryostat sectioned at a thickness of 10 μm. For detection of human HF and LF, the rH02 antibody (Cozzi, A. et al. *J. Biol. Chem.* 275, 25122-25129 (2000)) and a monoclonal mouse anti-human antibody (Alpha Diagnostics) were used, respectively. A rhodamine conjugated secondary antibody was used.

Example 7

Transferrin Receptor as an MRI Reporter

We demonstrate that a transgene encoding the transferrin-receptor-1 (TfR-1) can be used as an MRI reporter. In this example we show that the introduction of a TfR-1 transgene via a viral vector promotes upregulation of endogenous ferritin (FT), an iron loading phenotype, and elicits MRI contrast. These effects have been observed using cell culture studies and in vivo studies in the mouse brain (FIGS. 35 and 36, respectively).

Figure 35:
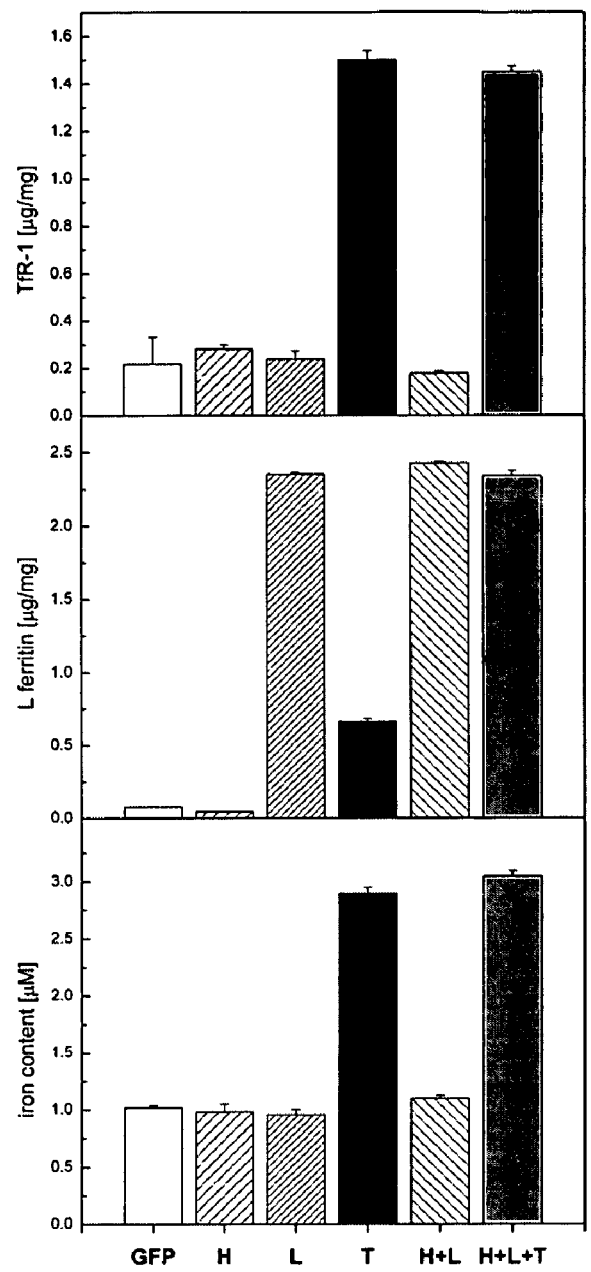
FIG. 35. In vitro characterization of human transferrin receptor-1 (TfR-1) with and without FT MRI reporters.

In the experiments shown in FIG. 35, the transgenes, delivered using adenoviruses, were: GFP=green fluorescent protein; H=heavy chain of human ferritin; L=light chain of human ferritin; T=TfR-1. Cells were also transduced with a mixture of transgenes as indicated (e.g., H+L=cells multiply transduced with a mixture of H and L vectors). FIG. 35 shows that cells transduced with T (black bars) have substantial iron loading, upregulation of endogenous (L) ferritin, and significant Tf R-1 transgene expression compared to the GFP control (open bars). Combining T with the H and L transgenes (H+L+T, gray bar) gives the largest overall iron loading effect, suggesting that this combination may also provide the most sensitive and robust MRI contrast in vivo. In all of these experiments cells (HEK293) were transduced with a multiplicity of infection of 3 for each adenovirus (AdV) encoding the transgenes. At 48 hours post-transduction, cells were assayed. To measure iron content, cells were harvested and disrupted in guanidinium and the total iron was assayed using the Ferene-S reagent and spectrophotometric absorbance at 600 nm. Iron content was calculated from a standard curve and normalized to a sample representative of $10^6$ cells/sample. For the ELISAs, cells were harvested, pelleted, and suspended in detergent solution. The L content was determined using the ICN Ferritin ELISA kit according to manufacturer's instructions (ICN Pharmaceuticals, Orangeburg, N.Y.). The TfR-1 content was determined using a human transferrin receptor ELISA kit (Ramco Laboratories, Stafford, Tex.), as prescribed by the manufacturer. Total protein was determined by using the Pierce BCA protein assay kit following the manufacturer's instructions (Pierce, Rockford, Ill.). The L and TfR-1 levels were normalized to the total protein content. The error bars are the standard error calculated from triplicate (n=3) samples.

In the experiments shown in FIG. 36, the transferrin receptor-based MRI reporter produces detectable MRI contrast (left panel, arrow) and immunohistochemistry shows the TfR-1 transgene expression (right panel, top) and an upregulation of endogenouse ferritin (right panel, bottom). Mice were inoculated in the striatum using stereotaxy with AdV vectors carrying a transgene encoding for human TfR-1 in right hemisphere, and the β-galactosidase (lacZ) control vector was injected into the left hemisphere. At five days post-inoculation, MR imaging was performed. The left panel of FIG. 36 shows typical MRI results. This T2-weighted coronal image slice through the injection site was acquired using identical imaging methods as described in Example 6

(above). Image contrast induced by the TfR-1 reporters is clearly seen in the right striatum. No significant MRI contrast is seen on the contralateral (left) side where the lacZ control virus was injected. The panels on the right side show immunohistochemistry in the same brain after MRI. After MRI the mouse was sacrificed, and the brain was removed and frozen in OTC embedding media. Slices were then cut through the brain at 14 µm thickness, mounted, fixed, and probed for human TfR-1 using anti-CD71 mAb (α-TfR, top right panel) (Ancell, Bayport, Minn., cat#: 223-020). Adjacent sections were also probed for endogenous, murine-specific, light-chain ferritin using Rabbit anti-Mo LFt sera F17 [Santambrogio, P. et al. Protein Expression And Purification, 19(1): p. 212-218 (2000)] (α-Mo-LFt, bottom right panel). For the immunohistochemistry a rhodamine-conjugated secondary antibody was used (Jackson ImmunoResearch Laboratories, West Grove, Pa.).

Example 8

Single-Chain Chimeric Ferritin (sc-Ft) Reporter

Figure 37:
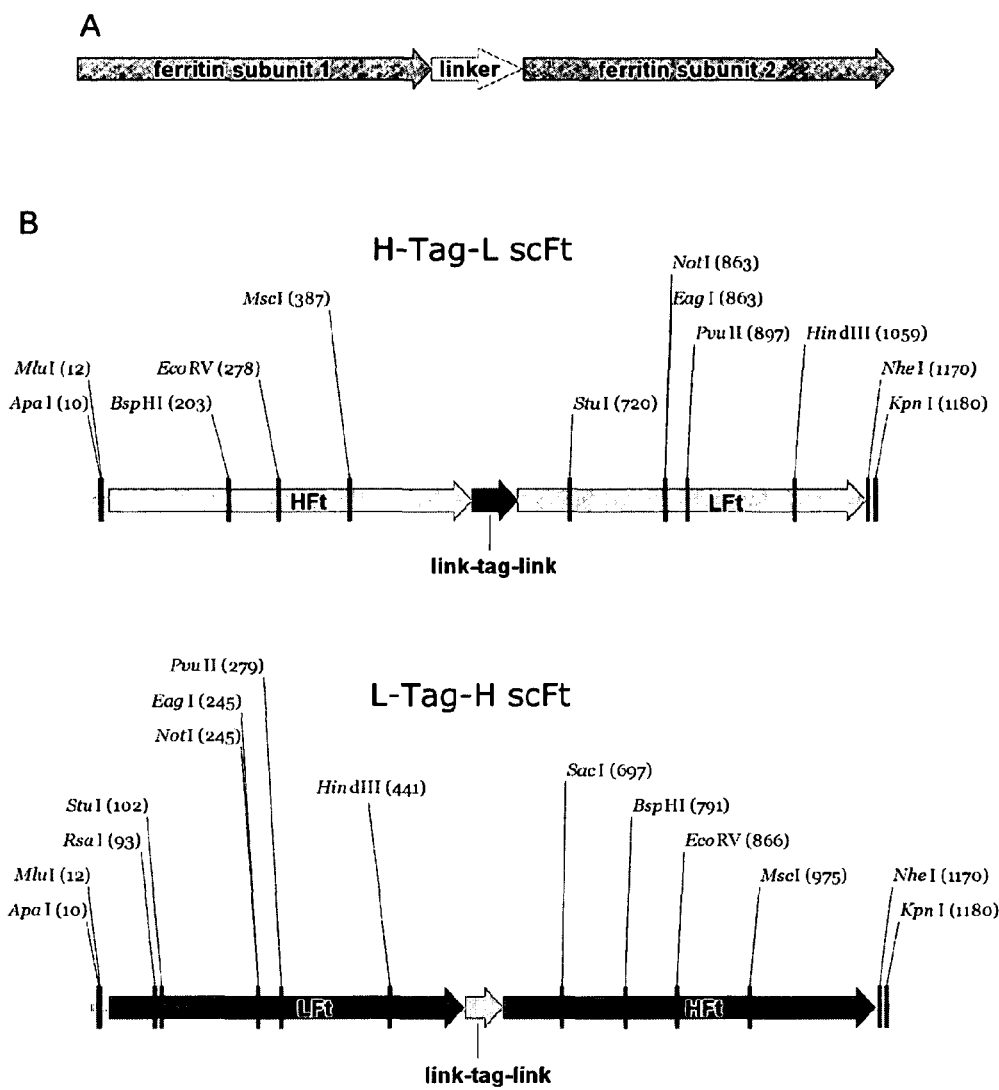
FIG. 37. In silico representations of sc-Ft reporters. A, Generic representation of ferritin-based MRI reporter constructed as a protein fusion containing different FT subunits tethered by a linker polypeptide. B, In silico generated construction of two example single-chain ferritin cDNA molecules. The individual components comprising the open reading frame are indicated by the colored arrows. The linker, "link-tag-link", fuses the subunit genes resulting in the expression of a single polypeptide. The H-Tag-L construct has the H and L subunits positioned as N-terminal and C-terminal components, respectively, whereas the L-Tag-H construct has these subunits fused in the reverse orientation.

Previous studies indicate that efficient iron uptake occurs in heteropolymeric ferritin [Corsi, B. et al., Biochem. J., 330: p. 315-320 (1998)]., and that FT heteropolymers with a specific heavy (H) and light (L) subunit ratio incorporate iron more effectively [Santambrogio, P. et al., Journal of Biological Chemistry, 268(17): p. 12744-12748 (1993)]. Thus, we have designed and evaluated single cistrons encoding synthetic single-chain FT chimeric duplex molecules that are composed of both the H and L FT subunits expressed as a single polypeptide (FIG. 37). These single chain chimeric ferritins have a fixed stoichiometry of the subunits (e.g., 1:1 ratio) when expressed in cells. Between the subunits we introduce a flexible linker polypeptide (FIG. 37A) which permits the subunits to fold with respect to each other and form functional ferritin shells.

The linker polypeptide can impart a variety of functions to the sc-Ft. For example, these linkers could encode a unique epitope tag (e.g., the HA-epitope, YPYDVPDYA; His, HHH-HHH; c-MYC, EQKLISEEDL; VSV-G, YTDIEMNRLGK; HSV, QPELAPEDPED; V5 GKPIPNPLLGLDST). These epitope tags can easily be detected using immunohistochemistry using highly selective antibodies, thus facilitating histological examination of the cells and tissues expressing the sc-Ft reporter, for example, after MRI examination. Alternatively, these epitope tags can be used to biochemically isolate the recombinant sc-Ft proteins from a cell lysate using immunopurification or other affinity reagents. Additionally, functional markers such as fluorescent proteins (examples are variants of GFP or DS-red) or enzymes (such as β-galactosidase, GST or HRP) could also be incorporated into the linker and be used to simultaneously ligate and label the two FT subunits; the linker can then be detected using fluorescence microscopy, histology, or biochemistry techniques. Furthermore, the linker polypeptide can be designed to target specific proteins within the cell, i.e., the linker may contain subcellular localization signals. For example, the linker may provide signals for modification by ubiquitinating enzymes, which in turn could be used promote cellular degradation of the sc-Ft reporter. In this way one could designate a degradation pathway for the reporter, which might be a useful feature when rapid turn-on and turn-off kinetics of the MRI reporter activity is desirable, or if the MRI reporter does not degrade and clear on its own in a particular cell type.

The linker polypeptide can also be used to modify the MRI contrasting function and stability of the sc-Ft reporter. The final structure of the ferritin shell formed from the single chain chimeric duplex molecules can depend on the flexibility, length, chemical properties (e.g., hydrobicity and charge distribution) and steric filling of the linker polypeptide. Thus via linker design one can engineer new ferritin molecules with modified structures, stabilities in vivo, and enhanced functional properties (i.e., enhanced NMR relaxivity). For example, increasing the steric volume, length, or rigidity of the linker polypeptide may increase the overall size of the fully formed ferritin shell and consequently facilitate greater iron loading capacity. Additionally, other changes in structure may increase iron loading kinetics into the shells. Furthermore, the linker may modify the shell's structure in such a way that its stability and turnover rate in the cell is affected, and this can be used as an additional means to control MRI reporter turn-on and turn-off in cells.

Figure 38:
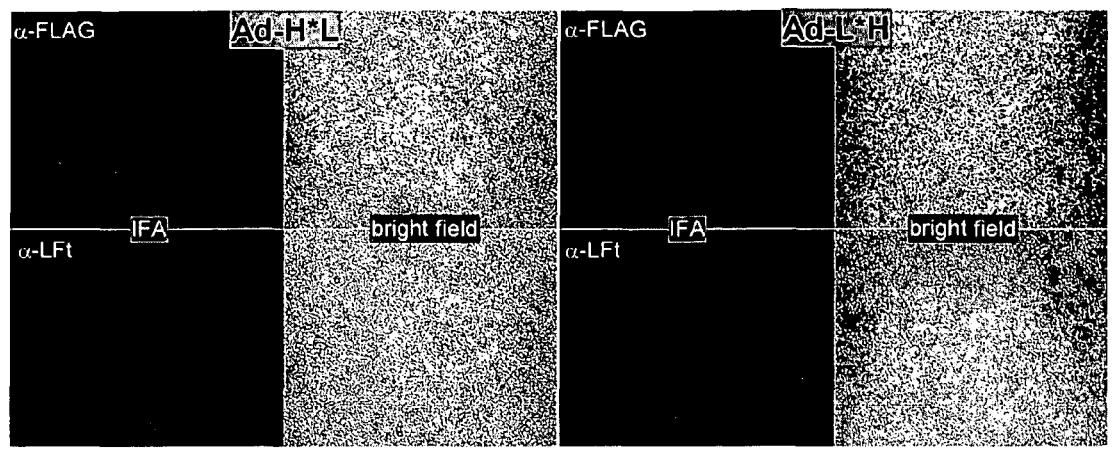
FIG. 38. Expression of single-chain ferritin (sc-Ft) chimeras. Immunofluorescent detection assays (IFA) were performed on HEK293 cells transduced with adenovirus containing either the H-Tag-L (Ad-H*L) or L-Tag-H (Ad-L*H) transgenes (FIG. 37) at a multiplicity of approximately 0.02. The cells were then fixed at 40 hours post-transduction and probed using anti-L (α-LFt) mAb (#FERT12-M, Alpha Diagnostics, Inc.) or anti-FLAG (α-FLAG) mAb (M2, Sigma, #F-3165), followed by a rhodamine-conjugated secondary antibody (Jackson ImmunoResearch). The corresponding bright field images of the cells are also shown.
Figure 39:
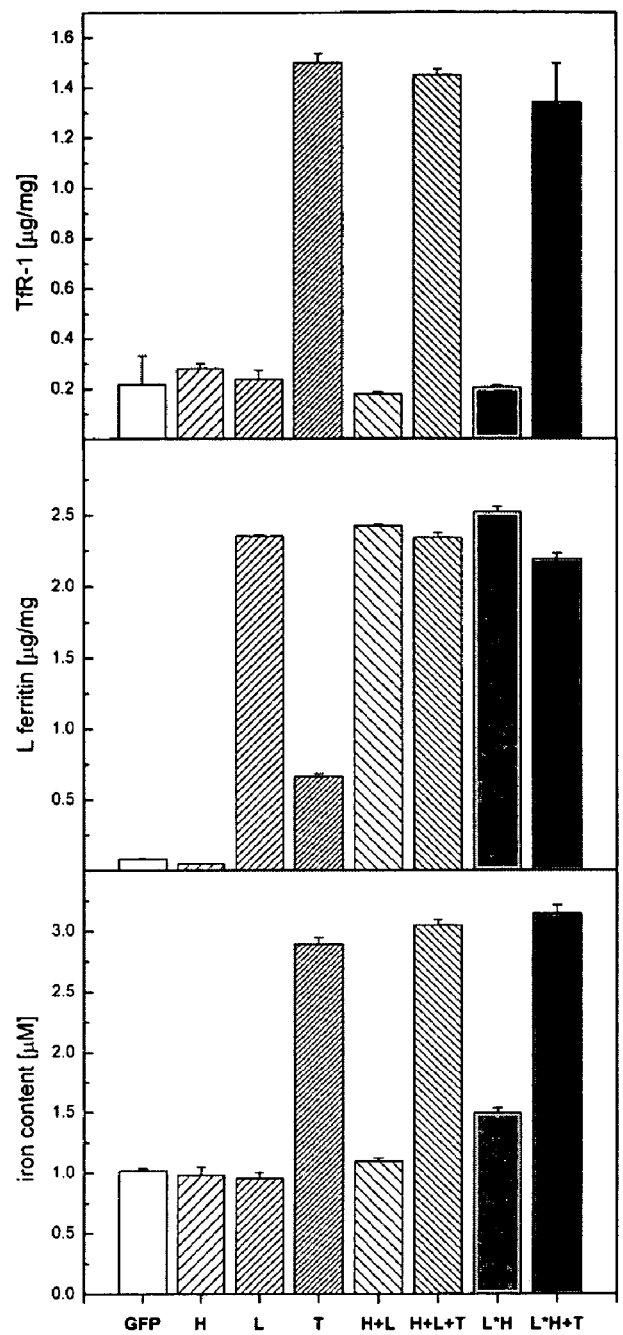
FIG. 39. In vitro levels of iron, L-chain and TfR-1 in sc-Ft chimera MRI reporter-transduced cells.
Figure 40:
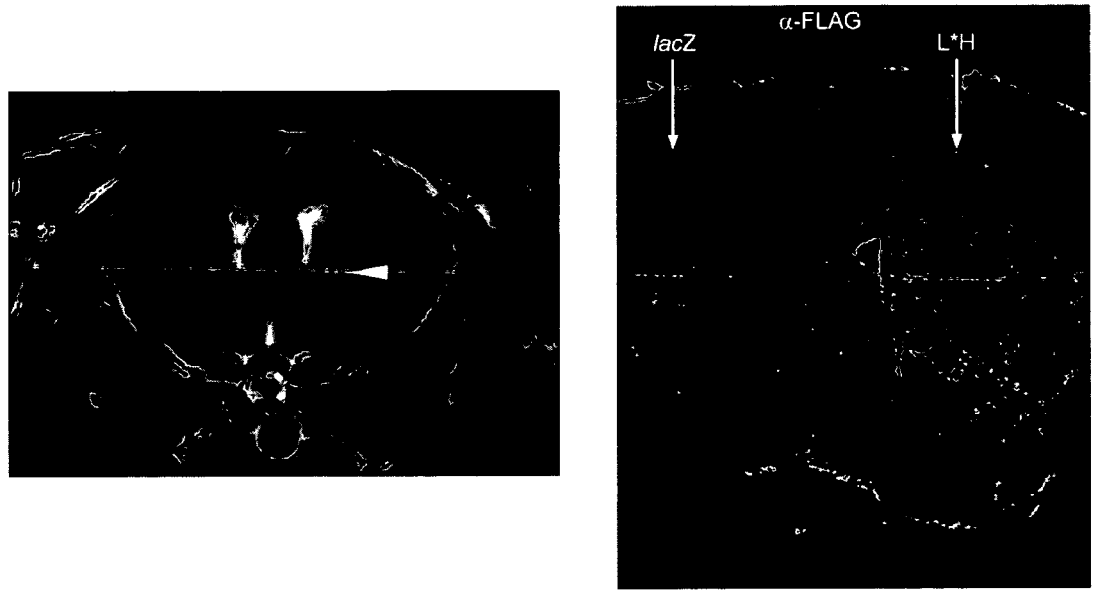
FIG. 40. In vivo application of the sc-Ft-based reporter expression in mouse brain. The sc-FT MRI reporter produces detectable MRI contrast (left panel, arrow) and immunohistochemistry in the same brain shows the presence of the FLAG epitope (right panel).

In order to test this scheme, single-chain ferritin (sc-Ft) chimeras were constructed that were composed of both the H and L chains (FIG. 37). We used oligonucleotide-directed PCR-mediated mutagenesis to introduce: i) unique restriction sites for cloning, ii) a Kozak consensus signal for optimal translational initiation, and iii) codon substitutions at the 5' start of the C-terminal gene and at the 3' stop of the N-terminal gene for the translational fusion. Also, we used synthetic DNAs to introduce linkers connecting the modified gene amplicons. The linkers fuse the two FT cDNAs in-frame and encode a FLAG epitope (amino acid sequence DYKD-DDDK) for use as a unique marker for immunodetection of the proteins. In vitro and in vivo characterizations of the sc-FT reporters are shown in FIGS. 38 through 40.

Representative sequences of the synthetic oligonucleotides that are used to join the ferritin subunits are shown below. When these DNAs are annealed and then ligated with subunit genes, they encode for flexible poly-glycine-serine domains flanking a central FLAG epitope (underlined), KSRGGGS DYKDDDDKGGGGSGAP.

```
"G4SFLAG-Fwd"-Coding strand:
AAATCTAGAGGCGGGGGCGGCAGCGATTACAAGGACGATGACGATAAGGG
CGGCGGGGCTCCGGCGCGCCAAA "G4SFLAG-Rev"-Noncoding strand:
TTTGGCGCGCCGGAGCCCCCGCCGCCCTTATCGTCATCGTCCTTGTAATC
GCTGCCGCCCCGCCTCTAGATTT The mutagenic oligonucleotides used to generate
the two different chimeric FT cDNAs are:

"HFt 3' Nhe-Kpn Rev"
ATTTGGTACCGCTAGCTTAGCTTTCATTATCACTGTCTCCCAGG

"HFt 5' Apa-Mlu-Kz Fwd"
AAATGGGCCCACGCGTGCCACCATGGCGACCGCGTCCACCTCGCAGGTG

"HFt C-term 5'-Mlu Fwd"
TTTACGCGTCATGACGACCGCGTCCACCTCGCAG

"HFt N-term 3'-Nhe Rev"
ATTGCTAGCGCTTTCATTATCACTGTCTCCCAGG

"LFt 3' Nhe-Kpn Rev"
ATTTGGTACCGCTAGCTTAGTCGTGCTTGAGAGTGAGCCTTTCG

"LFt 5' Apa-Mlu-Kz Fwd"
AAATGGGCCCACGCGTGCCACCATGGGCTCCCAGATTCGTCAGAAT
TATTCC

"LFt C-term 5'-Mlu Fwd"
TTTACGCGTCAATGAGCTCCCAGATTCGTCAG

"LFt N-term 3'-Nhe Rev"
AAAGCTAGCGTCGTGCTTGAGAGTGAG
```

The DNA sequences of the open reading frames (ORF) encoding the sc-Ft molecules are as follows:

```
DNA sequence of H*L chimera ORF:
ATGGCGACCGCGTCCACCTCGCAGGTGCGCCAGAACTACCACCAGGACTCAGAGGC
CGCCATCAACCGCCAGATCAACCTGGAGCTCTACGCCTCCTACGTTTACCTGTCCAT
GTCTTACTACTTTGACCGCGATGATGTGGCTTTGAAGAACTTTGCCAAATACTTTCTT
CACCAATCTCATGAGGAGAGGGAACATGCTGAGAAACTGATGAAGCTGCAGAACCA
ACGAGGTGGCCGAATCTTCCTTCAGGATATCAAGAAACCAGACTGTGATGACTGGG
AGAGCGGGCTGAATGCAATGGAGTGTGCATTACATTTGGAAAAAAATGTGAATCAG
TCACTACTGGAACTGCACAAACTGGCCACTGACAAAAATGACCCCCATTTGTGTGAC
TTCATTGAGACACATTACCTGAATGAGCAGGTGAAAGCCATCAAAGAATTGGGTGA
CCACGTGACCAACTTGCGCAAGATGGGAGCGCCCGAATCTGGCTTGGCGGAATATC
TCTTTGACAAGCACACCCTGGGAGACAGTGATAATGAAAGCGCTAGAGGCGGGGC
GGCAGCGATTACAAGGACGATGACGATAAGGGCGGCGGGGGCTCCGGCGCGTCAAT
GAGCTCCCAGATTCGTCAGAATTATTCCACCGACGTGGAGGCAGCCGTCAACAGCCT
GGTCAATTTGTACCTGCAGGCCTCCTACACCTACCTCTCTCTGGGCTTCTATTTCGAC
CGCGATGATGTGGCTCTGGAAGGCGTGAGCCACTTCTTCCGCGAACTGGCCGAGGA
GAAGCGCGAGGGCTACGAGCGTCTCCTGAAGATGCAAAACCAGCGTGGCGGCCGCG
CTCTCTTCCAGGACATCAAGAAGCCAGCTGAAGATGAGTGGGGTAAAACCCCAGAC
GCCATGAAAGCTGCCATGGCCCTGGAGAAAAAGCTGAACCAGGCCCTTTTGGATCTT
CATGCCCTGGGTTCTGCCCGCACGGACCCCCATCTCTGTGACTTCCTGGAGACTCAC
TTCCTAGATGAGGAAGTGAAGCTTATCAAGAAGATGGGTGACCACCTGACCAACCT
CCACAGGCTGGGTGGCCCGGAGGCTGGGCTGGGCGAGTATCTCTTCGAAAGGCTCA
CTCTCAAGCACGAC DNA sequence of L*H chimera ORF:
ATGGGCTCCCAGATTCGTCAGAATTATTCCACCGACGTGGAGGCAGCCGTCAACAG
CCTGGTCAATTTGTACCTGCAGGCCTCCTACACCTACCTCTCTCTGGGCTTCTATTTC
GACCGCGATGATGTGGCTCTGGAAGGCGTGAGCCACTTCTTCCGCGAACTGGCCGA
GGAGAAGCGCGAGGGCTACGAGCGTCTCCTGAAGATGCAAAACCAGCGTGGCGGCC
GCGCTCTCTTCCAGGACATCAAGAAGCCAGCTGAAGATGAGTGGGGTAAAACCCCA
GACGCCATGAAAGCTGCCATGGCCCTGGAGAAAAAGCTGAACCAGGCCCTTTTGGA
TCTTCATGCCCTGGGTTCTGCCCGCACGGACCCCCATCTCTGTGACTTCCTGGAGACT
CACTTCCTAGATGAGGAAGTGAAGCTTATCAAGAAGATGGGTGACCACCTGACCAA
CCTCCACAGGCTGGGTGGCCCGGAGGCTGGGCTGGGCGAGTATCTCTTCGAAAGGC
TCACTCTCAAGCACGACGCTAGAGGCGGGGCGGCAGCGATTACAAGGACGATGAC
GATAAGGGCGGCGGGGGCTCCGGCATGACGACCGCGTCCACCTCGCAGGTGCGCCA
GAACTACCACCAGGACTCAGAGGCCGCCATCAACCGCCAGATCAACCTGGAGCTCT
ACGCCTCCTACGTTTACCTGTCCATGTCTTACTACTTTGACCGCGATGATGTGGCTTT
GAAGAACTTTGCCAAATACTTTCTTCACCAATCTCATGAGGAGAGGGAACATGCTGA
GAAACTGATGAAGCTGCAGAACCAACGAGGTGGCCGAATCTTCCTTCAGGATATCA
AGAAACCAGACTGTGATGACTGGGAGAGCGGGCTGAATGCAATGGAGTGTGCATTA
CATTTGGAAAAAAATGTGAATCAGTCACTACTGGAACTGCACAAACTGGCCACTGA
CAAAAATGACCCCCATTTGTGTGACTTCATTGAGACACATTACCTGAATGAGCAGGT
GAAAGCCATCAAAGAATTGGGTGACCACGTGACCAACTTGCGCAAGATGGGAGCGC
CCGAATCTGGCTTGGCGGAATATCTCTTTGACAAGCACACCCTGGGAGACAGTGATA
ATGAAAGC
```

In vitro levels of iron, L-chain and TfR-1 in sc-Ft chimera MRI reporter-transduced cells are shown in FIG. 39. In these experiments, the transgenes are: GFP=green fluorescent protein; H; L; T=TfR-1; L*H=L-Tag-H chimera (FIG. 37B). Cells multiply transduced by a mixture of vectors are denoted as A+B, where A and B are the transgenes components. The L-Tag-H chimera (L*H) shows a strong iron-loading phenotype in transduced cells. Additionally, the L*H appears to sequester iron at a significantly higher efficiency than cells transduced with an equivalent amount of both the H and L transgenes. Cells co-expressing the L*H chimera with TfR-1 sequesters three times the amount of iron compared to H+L expressing cells. These data suggest that the synthetic single-chain chimera may exhibit considerably stronger effects on NMR relaxation rates than "wild-type" FT molecules; which in turn translates into more robust MRI contrast at lower infectious doses. Cells (HEK293) were transduced with a multiplicity of 3 using each of the AdV encoding the transgenes. Following transduction, the cultures were incubated in low-serum media supplemented with 1 mg/ml purified holotransferrin. At 48 hours post-transduction, cells were assayed using the methods described in Example 6. ELISAs were used to assay L and TfR-1 content, and the data shown are normalized to the total protein content as measured by the BCA method (see Example 6 for additional details). Iron determination was calculated from a standard curve and normalized to a sample representative of $10^6$ cells/sample. The standard error bars are calculated from triplicate samples.

In vivo application of the sc-Ft-based reporter expression in mouse brain is shown in FIG. 40. The sc-FT MRI reporter produces detectable MRI contrast (left panel, arrow) and immunohistochemistry in the same brain shows the presence of the FLAG epitope (right panel). Mice were inoculated in the striatum using stereotaxy, where AdV vectors carrying a transgene encoding for L-Tag-H (FIG. 37B) were injected into the right hemisphere, and the β-galactosidase (lacZ) control vector was injected into the left hemisphere. At five days post-inoculation, MR imaging was performed. The left panel above shows typical MRI results. This T2-weighted coronal image slice through the injection site was acquired using identical imaging methods as described in Example 6 (above). Image contrast induced by the L-Tag-H reporter is clearly seen in the right striatum. No significant MRI contrast is seen on the contralateral (left) side where the lacZ control virus was injected. The panels on the right side show immunohistochemistry in the same brain after MRI. After MRI the mouse was sacrificed, and the brain was removed and frozen in OTC embedding media. Slices were then cut through the brain at 14 μm thickness, mounted, fixed, and probed for sc-Ft using the α-FLAG mAb (M2, Sigma, F-3165), followed by a rhodamine-conjugated secondary antibody (Jackson ImmunoResearch).

Example 9

MRI Reporter Activity in the Brain Under Stimuli- and Tissue-Specific Promoter Specific sets of genes can be used as markers to examine differential cellular activity in tissues. For example, the immediate early genes (IEGs), including c-fos, c-jun, and egr-1, encode for transcription factors that are transcriptionally regulated by an array of intracellular signaling pathways, and effect the transcriptional activity of downstream late genes. A variety of extracellular or physiological stimuli provide the switch that activates these cell signaling pathways. The activation of these IEGs results in a transcriptional cascade activating downstream genes that comprises the genetic circuitry for cells to respond to signals in their environment. For example, these signals may be induced in neurons by hormonal stimuli, sensory stimuli, stimulation of the motor cortex or other motor behaviors, and by various drugs and toxins that act on a variety of neurotransmitter systems. Because the IEGs can be transiently activated in an elegant tissue-specific manner, the transcriptional promoters of the IEGs used in conjunction with MRI reporters are ideal systems for studying the metabolic activation of tissues noninvasively.

Figure 41:
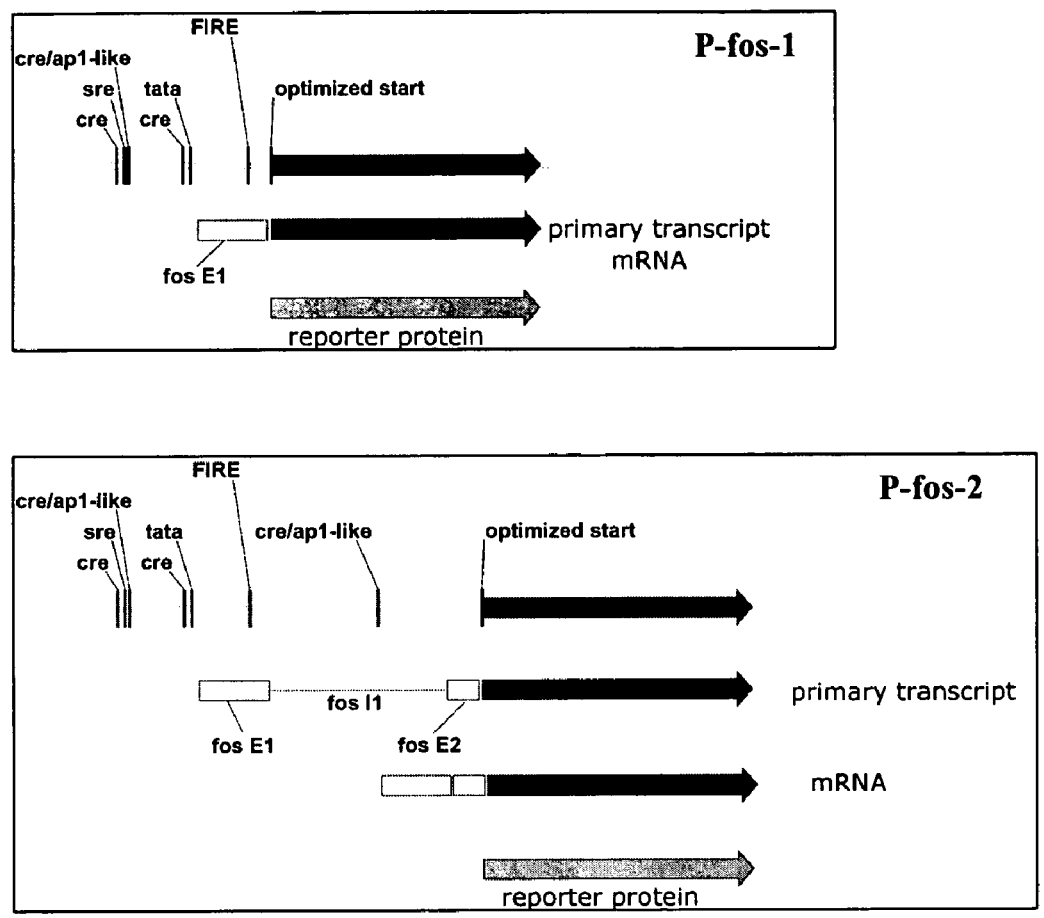
FIG. 41. Murine c-fos DNA promoter constructs and transcripts resulting in reporter expression. P-fos-1 (top) was constructed to retain all but one regulatory element found in the native c-fos gene. P-fos-2 (bottom) retains all known regulatory elements, including the intragenic cre/apl-like element, and also includes the fos intron-1 (fosI1). All potential translational start codons in fos exon-1 (fos E1) and exon-2 (fos E2) have been mutated, and thus these regions of the transcript will behave as a 5' untranslated region (UTR) and allow for proper reporter expression.

Previous reports demonstrated the utility of c-Fos protein fusions using the reporters β-gal and GFP for reading-out tissue-specific transcriptional activity of the native c-fos promoter. See for example: Barth, A. L., et al. Journal Of Neuroscience, 24(29): p. 6466-6475 (2004); Wilson, Y., N. et al. Proceedings Of The National Academy Of Sciences Of The United States Of America, 99(5): p. 3252-3257 (2002); Schilling, K. et al., Proceedings Of The National Academy Of Sciences Of The United States Of America, 88(13): p. 5665-5669 (1991). However, fos-β-gal and fos-GFP fusion reporters target to the nucleus via the inclusion of the fos nuclear localization signal. For MRI reporters, nuclear localization may not optimal for reporter activity. Thus, examples of engineered c-fos promoters are described in FIG. 41 that provide stimuli-dependent and cytoplasmic expression of the MRI reporters. The first example, P-fos-1 (FIG. 41), contains the minimal fos promoter, and the second version, P-fos-2 (FIG. 41), contains the c-fos exons 1 and 2 and includes intron 1. In both promoter constructs, authentic and potential ATG start codons found in the fos transcript have been mutated. By removing these, the modified sequences will serve as a 5' UTR in both constructs. The modified exon-1/intron-1/exon-2 region, as in the P-fos-2 construct, will facilitate RNA processing and enhance transgene expression. Those skilled in the art can devise many other variations of the schemes outlined in FIG. 41.

The designs described herein incorporating the MRI reporters can be used to non-invasively monitor endogenous gene activity in the central nervous system (CNS). For example, one can utilize the promoter components of the immediate early gene c-fos as a prototype marker to probe for cellular activation in the CNS, which can be visualized using the MRI reporters. In addition, promoter modules derived from other IEGs could also be used to drive stimuli- and tissue-specific reporter expression. These types of systems can be useful for studying developmental gene regulation, neuronal plasticity, and gene activity in learning circuits of the brain. Additionally, this reporter system can be used to visualize how pharmaceuticals affect gene regulation in different brain regions via the contrasting effects produced by the MRI reporters. The MRI reporters allow one to view c-fos or IEG activity in a longitudinal fashion.

```
DNA sequence of a P-fos-2 promoter construct
expressing a sc-Ft reporter:
TTGCTTCTCCTAATACCAGAGACTCAAAAAAAAAAAAAAGTTCCAGATTGCTGGA

CAATGACCCGGGTCTCATCCCTTGACCCTGGGAACCGGGTCCACATTGAATCAGGTG

CGAATGTTCGCTCGCCTTCTCTGCCTTTCCCGCCTCCCCTCCCCGGCCGCGGCCCCG

GTTCCCCCCCTGCGCTGCACCCTCAGAGTTGGCTGCAGCCGGCGAGCTGTTCCCGTC

AATCCCTCCCTCCTTTACACAGGATGTCCATATTAGGACATCTGCGTCAGCAGGTTTC

CACGGCCGGTCQCTGTTGTTCTGGGGGGGGGACCATCTCCGAAATCCTACACGCGGA

AGGTCTAGGAGACCCCCTAAGATCCCAAATGTGAACACTCATAGGTGAAAGATGTA

TGCCAAGACGGGGGTTGAAAGCCTGGGGCGTAGAGTTGACGACAGAGCGCCCGCAG

AGGGCCTTGGGGCGCGCTTCCCCCCCCTTCCAGTTCCGCCCAGTGACGTAGGAAGTC

CATCCATTCACAGCGCTTCTATAAAGGCGCCAGCTGAGGCGCCTACTACTCCAACCG

CGACTGCAGCGAGCAACTGAGAAGACTGGATAGAGCCGGCGGTTCCGCGAACGAGC

AGTGACCGCGCTCCCACCCAGCTCTGCTCTGCAGCTCCCACCAGTGTCTACCCCTGG

ACCCCTTGCCGGGCTTTCCCCAAACTTCGACCTTGATATTCACGCGTTTCAACGCCG

ACTACGAGGCGTCATCCTCCCGCTGCAGTAGCGCCTCCCCGGCCGGGGACAGCCTTT

CCTACTACCATTCCCCAGCCGACTCCTTCTCCAGCTTAAGCTCTCCTGTCAACACACA

GGTGAGTTTGGCTTTGTGTAGCCGCCAGGTCCGCGCTGAGGGTCGCCGTGGAGGAG

ACACTGGGGTGTGACTCGCAGGGGCGGGGGGTCTTCCTTTTTCGCTCTGGAGGGAG

ACTGGCGCGGTCAGAGCAGCCTTAGCCTGGGAACCCAGGACTTGTCTGAGCGCGTG
```

```
-continued
CACACTTGTCATAGTAAGACTTAGTGACCCCTTCCCGCGCGGCAGGTTTATTCTGAG

TGGCCTGCCTGCATTCTTCTCTCGGCCGACTTGTTTCTGAGATCAGCCGGGGCCAAC

AAGTCTCGAGCAAAGAGTCGCTAACTAGAGTTTGGGAGGCGGCAAACCGCGGCAAT

CCCCCCTCCCGGGGCAGCCTGGAGCAGGGAGGAGGGAGGAGGGAGGAGGGTGCTG

CGGGCGGGTGTGTAAGGCAGTTTCATTGATAAAAAGCGAGTTCATTCTGGAGACTCC

GGAGCAGCGCCTGCGTCAGCGCAGACGTCAGGGATATTTATAACAAACCCCCTTTC

GAGCGAGTGATGCCGAAGGGATAACGGGAACGCAGCAGTAGGATGGAGGAGAAAG

GCTGCGCTGCGGAATTCAAGGGAGGATATTGGGAGAGCTTTTATCTCCGATGAGGTG

CATACAGGAAGACATAAGCAGTCTCTGACCGGAATGCTTCTCTCTCCCTGCTTCATG

CGACACTAGGGCCACTTGCTCCACCTGTGTCTGGAACCTCCTCGCTCACCTCCGCTTT

CCTCTTTTTGTTTTGTTTCAGGACTTTTGCGCAGATCTGTCCGTCTCTAGTGCCAACTT

TATCCCCACGGTGACAGCCATCTCCACCAGCCCAGACCTGCAGTGGCTGGTGCAGCC

CACTCTGGTCTCCTCCGTGGCCCCATCGCAGACCAGGGCCCACGCGTGCCACCATGG

CGACCGCGTCCACCTCGCAGGTGCGCCAGAACTACCACCAGGACTCAGAGGCCGCC

ATCAACCGCCAGATCAACCTGGAGCTCTACGCCTCCTACGTTTACCTGTCCATGTCTT

ACTACTTTGACCGCGATGATGTGGCTTTGAAGAACTTTGCCAAATACTTTCTTCACCA

ATCTCATGAGGAGAGGGAACATGCTGAGAAACTGATGAAGCTGCAGAACCAACGAG

GTGGCCGAATCTTCCTTCAGGATATCAAGAAACCAGACTGTGATGACTGGGAGAGC

GGGCTGAATGCAATGGAGTGTGCATTACATTTGGAAAAAAATGTGAATCAGTCACT

ACTGGAACTGCACAAACTGGCCACTGACAAAAATGACCCCCATTTGTGTGACTTCAT

TGAGACACATTACCTGAATGAGCAGGTGAAAGCCATCAAAGAATTGGGTGACCACG

TGACCAACTTGCGCAAGATGGGAGCGCCCGAATCTGGCTTGGCGGAATATCTCTTTG

ACAAGCACACCCTGGGAGACAGTGATAATGAAAGCGCTAGAGGCGGGGCGGCAG

CGATTACAAGGACGATGACGATAAGGGCGGCGGGGGCTCCGGCGCGTCAATGAGCT

CCCAGATTCGTCAGAATTATTCCACCGACGTGGAGGCAGCCGTCAACAGCCTGGTCA

ATTTGTACCTGCAGGCCTCCTACACCTACCTCTCTCTGGGCTTCTATTTCGACCGCGA

TGATGTGGCTCTGGAAGGCGTGAGCCACTTCTTCCGCGAACTGGCCGAGGAGAAGC

GCGAGGGCTACGAGCGTCTCCTGAAGATGCAAAACCAGCGTGGCGGCCGCGCTCTC

TTCCAGGACATCAAGAAGCCAGCTGAAGATGAGTGGGGTAAAACCCCAGACGCCAT

GAAAGCTGCCATGGCCCTGGAGAAAAAGCTGAACCAGGCCCTTTTGGATCTTCATGC

CCTGGGTTCTGCCCGCACGGACCCCCATCTCTGTGACTTCCTGGAGACTCACTTCCTA

GATGAGGAAGTGAAGCTTATCAAGAAGATGGGTGACCACCTGACCAACCTCCACAG

GCTGGGTGGCCCGGAGGCTGGGCTGGGCGAGTATCTCTTCGAAAGGCTCACTCTCAA

GCACGACTAAGCTAGCGGTACCAAAT
```

The DNA sequence of the P-fos-1 promoter construct is generated simply by obtaining the 724 base-pair 5' MluI fragment that is wave-underlined in the above sequence.

INCORPORATION BY REFERENCE

All of the patents, publications and sequence database entries cited herein are hereby incorporated by reference. Also incorporated by reference are the following: Trinder et al., Int. J. Biochem. & Cell Biol., 35: 292-296 (2003); Fleming et al., Proc. Natl. Acad. Sci. USA 99: 10653-10658 (2002); Fleming et al., Proc. Natl. Acad. Sci. USA 97: 2214-2219 (2000); U.S. patent Publication Nos. 2004/0194161; 2004/0205846; and 2004/0205847.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. An isolated fusion protein comprising a ferritin heavy chain subunit having SEQ ID NO: 2 and a ferritin light chain subunit having SEQ ID NO: 4, wherein the ferritin heavy chain subunit is positioned C-terminal to the light chain subunit, wherein the isolated fusion protein is a metal-binding protein, and wherein expression of said fusion protein in cells results in increased iron loading compared to expression of wild-type ferritin.

2. The fusion protein of claim 1, wherein a linker connects the ferritin heavy chain subunit to the ferritin light chain subunit.

3. An isolated nucleic acid encoding the fusion protein of claim 1.

4. A vector for transfection and expression of a ferritin fusion protein in a multicellular organism for imaging or diagnostic purposes comprising a recombinant nucleic acid encoding a fusion protein of claim 1, wherein the vector is a viral vector.

5. The vector of claim 4, wherein the viral vector is derived from one or more of the viruses selected from the group consisting of: an adenovirus, an adenovirus-associated virus, a herpes simplex virus, a retrovirus, an alphavirus, a poxvirus, an arena virus, a vaccinia virus, an influenza virus and a polio virus.

6. The fusion protein of claim 1, further comprising a bound superparamagnetic iron complex.

* * * * *

SEQUENCE LISTING

<160> NUMBER OF SEQ ID NOS: 22

<210> SEQ ID NO 1
<211> LENGTH: 955
<212> TYPE: DNA
<213> ORGANISM: Homo sapiens

<400> SEQUENCE: 1

```
ggggagacgt tcttcgccga gagtcgtcgg ggtttcctgc ttcaacagtg cttggacgga      60
acccggcgct cgttcccac cccggccggc cgcccatagc cagccctccg tcacctcttc     120
accgcaccct cggactgccc caaggccccc gccgccgctc cagcgccgcg cagccaccgc     180
cgccgccgcc gcctctcctt agtcgccgcc atgacgaccg cgtccacctc gcaggtgcgc     240
cagaactacc accaggactc agaggccgcc atcaaccgcc agatcaacct ggagctctac     300
gcctcctacg tttacctgtc catgtcttac tactttgacc gcgatgatgt ggcttttgaag     360
aactttgcca atactttct tcaccaatct catgaggaga gggaacatgc tgagaaactg     420
atgaagctgc agaaccaacg aggtggccga atcttccttc aggatatcaa gaaaccagac     480
tgtgatgact gggagagcgg gctgaatgca atggagtgtg cattacattt ggaaaaaaat     540
gtgaatcagt cactactgga actgcacaaa ctggccactg acaaaaatga ccccatttg     600
tgtgacttca ttgagacaca ttacctgaat gagcaggtga agccatcaa agaattgggt     660
gaccacgtga ccaacttgcg caagatggga gcgcccgaat ctggcttggc ggaatatctc     720
tttgacaagc acaccctggg agacagtgat aatgaaagct aagcctcggg ctaatttccc     780
catagccgtg gggtgacttc cctggtcacc aaggcagtgc atgcatgttg gggtttcctt     840
tacctttct ataagttgta ccaaaacatc cacttaagtt ctttgatttg taccattcct     900
tcaaataaag aaatttggta ccctcaaaaa aaaaaaaaaa aaaaaaaaaa aaaaa          955
```

<210> SEQ ID NO 2
<211> LENGTH: 183
<212> TYPE: PRT
<213> ORGANISM: Homo sapiens

<400> SEQUENCE: 2

Met Thr Thr Ala Ser Thr Ser Gln Val Arg Gln Asn Tyr His Gln Asp
  1               5                  10                  15

Ser Glu Ala Ala Ile Asn Arg Gln Ile Asn Leu Glu Leu Tyr Ala Ser
                 20                  25                  30

Tyr Val Tyr Leu Ser Met Ser Tyr Tyr Phe Asp Arg Asp Asp Val Ala
             35                  40                  45

Leu Lys Asn Phe Ala Lys Tyr Phe Leu His Gln Ser His Glu Glu Arg
         50                  55                  60

Glu His Ala Glu Lys Leu Met Lys Leu Gln Asn Gln Arg Gly Gly Arg
 65                  70                  75                  80

Ile Phe Leu Gln Asp Ile Lys Lys Pro Asp Cys Asp Asp Trp Glu Ser
                 85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly

```
                145                 150                 155                 160
Ala Pro Glu Ser Gly Leu Ala Glu Tyr Leu Phe Asp Lys His Thr Leu
                    165                 170                 175

Gly Asp Ser Asp Asn Glu Ser
                180

<210> SEQ ID NO 3
<211> LENGTH: 860
<212> TYPE: DNA
<213> ORGANISM: Homo sapiens

<400> SEQUENCE: 3
tgcatcaaaa agctttattt ccatttggtc caaggcttgt taggatagtt aagaaagctg      60
cctattggct ggagggagag cttaggcag aagccctatt actttgcaag gggcccttca     120
gaagtcgctg ggctcagaag gctcttagtc gtgcttgaga gtgagccttt cgaagagata    180
ctcgcccagc ccagcctccg ggccacccag cctgtggagg ttggtcaggt ggtcacccat    240
cttcttgata agcttcactt cctcatctag gaagtgagtc tccaggaagt cacagagatg    300
ggggtccgtg cgggcagaac caggggcatg aagatccaaa agggcctggt tcagcttttt    360
ctccagggcc atggcagctt tcatggcgtc tggggtttta ccccactcat cttcagctgg    420
cttcttgatg tcctggaaga gagcgcggcc gccacgctgg ttttgcatct tcaggagacg    480
ctcgtagccc tcgcgcttct cctcggccaa ttcgcggaag aagtggctca cgccttccag    540
agccacatca tcgcggtcga aatagaagcc cagagagagg taggtgtagg aggcctgcag    600
gtacaaattg accaggctgt tgacggctgc ctccacgtcg gtggaataat tctgacgaat    660
ctgggagctc atggttggtt ggcaagaagg agctaaccac aaaaacggtg ctggcaggtc    720
ccagaagcag gagatggccg agaagatggt cccggaggtt gcaagcggag aggaaatcgg    780
agggcggtcg gaggctggaa gagagtcccc ggatctgttc cgtccaaaca ctgttgaagc    840
aagagacaga cccgcgggac                                                860

<210> SEQ ID NO 4
<211> LENGTH: 132
<212> TYPE: PRT
<213> ORGANISM: Homo sapiens

<400> SEQUENCE: 4

Met Gly Val Arg Ala Gly Arg Thr Gln Gly Met Lys Ile Gln Lys Gly
  1               5                  10                  15

Leu Val Gln Leu Phe Leu Gln Gly His Gly Ser Phe His Gly Val Trp
                 20                  25                  30

Gly Phe Thr Pro Leu Ile Phe Ser Trp Leu Leu Asp Val Leu Glu Glu
             35                  40                  45

Ser Ala Ala Ala Thr Leu Val Leu His Leu Gln Glu Thr Leu Val Ala
         50                  55                  60

Leu Ala Leu Leu Leu Gly Gln Phe Ala Glu Glu Val Ala His Ala Phe
     65                  70                  75                  80

Gln Ser His Ile Ile Ala Val Glu Ile Glu Ala Gln Arg Glu Val Gly
                 85                  90                  95

Val Gly Gly Leu Gln Val Gln Ile Asp Gln Ala Val Asp Gly Cys Leu
            100                 105                 110

His Val Gly Gly Ile Ile Leu Thr Asn Leu Gly Ala His Gly Trp Leu
        115                 120                 125

Ala Arg Arg Ser
        130
```

<210> SEQ ID NO 5
<211> LENGTH: 866
<212> TYPE: DNA
<213> ORGANISM: Mus musculus

<400> SEQUENCE: 5

```
cagacgttct cgcccagagt cgccgcggtt tcctgcttca acagtgcttg aacggaaccc      60
ggtgctcgac ccctccgacc cccgccggcc gcttcgagcc tgagcccttt gcaacttcgt     120
cgttccgccg ctccagcgtc gccaccgcgc ctcgccccgc cgccaccatg accaccgcgt     180
ctccctcgca agtgcgccag aactaccacc aggacgcgga ggctgccatc aaccgccaga     240
tcaacctgga gttgtatgcc tcctacgtct atctgtctat gtcttgttat tttgaccgag     300
atgatgtggc tctgaagaac tttgccaaat actttctcca ccaatctcat gaggagaggg     360
agcatgccga gaaactgatg aagctgcaga accagcgagg tggccgaatc ttcctgcagg     420
atataaagaa accagaccgt gatgactggg agagcgggct gaatgcaatg gagtgtgcac     480
tgcacttgga aaagagtgtg aatcagtcac tactggaact gcacaaactg ctactgaca      540
agaatgatcc ccactatgt gacttcattg agacgtatta tctgagtgaa caggtgaaat      600
ccattaaaga actgggtgac cacgtgacca acttacgcaa gatgggtgcc cctgaagctg     660
gcatggcaga tatctctttt gacaagcaca ccctgggaca cggtgatgag agctaagctg     720
acttccccaa agccacgtga ctttactggt cactgaggca gtgcatgcat gtcaggctgc     780
cttcatcttt tctataagtt gcaccaaaac atctgcttaa gttctttaat ttgtaccatt     840
tcttcaaata aagaattttg gtaccc                                          866
```

<210> SEQ ID NO 6
<211> LENGTH: 182
<212> TYPE: PRT
<213> ORGANISM: Mus musculus

<400> SEQUENCE: 6

```
Met Thr Thr Ala Ser Pro Ser Gln Val Arg Gln Asn Tyr His Gln Asp
  1               5                  10                  15

Ala Glu Ala Ala Ile Asn Arg Gln Ile Asn Leu Glu Leu Tyr Ala Ser
             20                  25                  30

Tyr Val Tyr Leu Ser Met Ser Cys Tyr Phe Asp Arg Asp Asp Val Ala
         35                  40                  45

Leu Lys Asn Phe Ala Lys Tyr Phe Leu His Gln Ser His Glu Glu Arg
     50                  55                  60

Glu His Ala Glu Lys Leu Met Lys Leu Gln Asn Gln Arg Gly Gly Arg
 65                  70                  75                  80

Ile Phe Leu Gln Asp Ile Lys Lys Pro Asp Arg Asp Asp Trp Glu Ser
                 85                  90                  95

Gly Leu Asn Ala Met Glu Cys Ala Leu His Leu Glu Lys Ser Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr Tyr Tyr Leu Ser Glu Gln Val Lys
    130                 135                 140

Ser Ile Lys Glu Leu Gly Asp His Val Thr Asn Leu Arg Lys Met Gly
145                 150                 155                 160

Ala Pro Glu Ala Gly Met Ala Glu Tyr Leu Phe Asp Lys His Thr Leu
                165                 170                 175
```

Gly His Gly Asp Glu Ser
            180

<210> SEQ ID NO 7
<211> LENGTH: 920
<212> TYPE: DNA
<213> ORGANISM: Mus musculus

<400> SEQUENCE: 7

| | | |
|---|---|---|
| cagcgccttg gaggtcccgt ggatctgtgt acttgcttca acagtgtttg aacggaacag | 60 |
| acccggggat tcccactgta ctcgcttcca ccgccttta caagtctctc cagtcgcagc | 120 |
| ctccgggacc atctcctcgc tgccttcagc tcctaggacc agtctgcacc gtctcttcgc | 180 |
| ggttagctcc tactccggat cagccatgac ctctcagatt cgtcagaatt attccaccga | 240 |
| ggtggaagct gccgtgaacc gcctggtcaa cttgcacctg cgggcctcct acacctacct | 300 |
| ctctctgggc ttcttttttg atcgggatga cgtggctctg gaaggcgtag gccacttctt | 360 |
| ccgcgaattg gccgaggaga agcgcgaggg cgcggagcgt ctcctcgagt ttcagaacga | 420 |
| tcgcgggggc cgtgcactct ccaggatgt gcagaagcca tctcaagatg aatgggtaa | 480 |
| aacccaggag gccatggaag ctgccttggc catggagaag aacctgaatc aggccctctt | 540 |
| ggatctgcat gccctgggtt ctgcccgcac ggaccctcat ctctgtgact tcctggaaag | 600 |
| ccactatctg gataaggagg tgaaactcat caagaagatg ggcaaccatc tgaccaacct | 660 |
| ccgcagggtg gcggggccac aaccagcgca gactggcgcg ccccaggggt ctctgggcga | 720 |
| gtatctcttt gagcgcctca ctctcaagca cgactaggag gcctctgtac cttccaaggg | 780 |
| gctccccct ctgctctgca ccagcccgcc ctgggacctc cacctgaatg aacctctcaa | 840 |
| gccactaggc agctttgtaa ccgtcctcca gcctctgtca agtcttggac caagtaaaaa | 900 |
| taaagctttt tgagaccccg | 920 |

<210> SEQ ID NO 8
<211> LENGTH: 183
<212> TYPE: PRT
<213> ORGANISM: Mus musculus

<400> SEQUENCE: 8

Met Thr Ser Gln Ile Arg Gln Asn Tyr Ser Thr Glu Val Glu Ala Ala
 1               5                  10                  15

Val Asn Arg Leu Val Asn Leu His Leu Arg Ala Ser Tyr Thr Tyr Leu
            20                  25                  30

Ser Leu Gly Phe Phe Asp Arg Asp Asp Val Ala Leu Glu Gly Val
        35                  40                  45

Gly His Phe Phe Arg Glu Leu Ala Glu Glu Lys Arg Glu Gly Ala Glu
    50                  55                  60

Arg Leu Leu Glu Phe Gln Asn Asp Arg Gly Gly Arg Ala Leu Phe Gln
65                  70                  75                  80

Asp Val Gln Lys Pro Ser Gln Asp Glu Trp Gly Lys Thr Gln Glu Ala
                85                  90                  95

Met Glu Ala Ala Leu Ala Met Glu Lys Asn Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Ser His Tyr Leu Asp Lys Glu Val Lys Leu Ile Lys Lys
    130                 135                 140

Met Gly Asn His Leu Thr Asn Leu Arg Arg Val Ala Gly Pro Gln Pro
145                 150                 155                 160

Ala Gln Thr Gly Ala Pro Gln Gly Ser Leu Gly Glu Tyr Leu Phe Glu
                165                 170                 175

Arg Leu Thr Leu Lys His Asp
            180

<210> SEQ ID NO 9
<211> LENGTH: 869
<212> TYPE: DNA
<213> ORGANISM: Mus musculus

<400> SEQUENCE: 9
ggaagactgt aaaagtcttg tcattttgtt cagtgaagtc ccctcattca catcaccaag     60
gatgatgaca gtctctccag tcgccgcagc ctccgggacc atctccttgc cgccttccgg    120
tcctaggacc agccagcccc gtcttcgcgg ttagctccat actccggatc agccatgacc    180
tctcagattc gtcagaatta ttccaccgaa gtggaagctg ccgtgaaccg cctggtcaac    240
ttgcacctgc gggcctctta cacctacctc tctctgggct tcttttttga tcgggatgac    300
gtggctttgg aaggcgtagg ccacttcttc cgcgaattgg ccgaggagaa gcgcgagggc    360
gcggagcgtc tcctcaagtt gcagaacgaa cgcgggggcc gtgcactctt ccaggatgtg    420
cagaagccat ctcaagatga gtggggtaaa accctggagg ccatccaagc tgccttgcgc    480
ctggagaaga acctgaacca ggccctcttg gatctgcacg ccctgggctc tgcccgcaca    540
gaccctcacc tctgtgactt cttggaaagc cacttcctgg ataaggaggt gaagctcatc    600
aagaagatgg gcaaccacct gaccaacctc cgtagggtgg cagggccaca accagtgcag    660
actggcgtgg cccaggcatc tctgggcgag tatctctttg agcgcctcac tctgaagcac    720
gactaggcct ctgtgccttc caaggggctc cctcctctgc tctgcaccga ccgcctcagc    780
acctccaccc gaatgaacct ctaaagccac taggcagctt tgtaaccgcc ctggagcctc    840
tcccaagtct tggaccaagt aaaaataaa                                     869

<210> SEQ ID NO 10
<211> LENGTH: 183
<212> TYPE: PRT
<213> ORGANISM: Mus musculus

<400> SEQUENCE: 10

Met Thr Ser Gln Ile Arg Gln Asn Tyr Ser Thr Glu Val Glu Ala Ala
  1               5                  10                  15

Val Asn Arg Leu Val Asn Leu His Leu Arg Ala Ser Tyr Thr Tyr Leu
                20                  25                  30

Ser Leu Gly Phe Phe Phe Asp Arg Asp Asp Val Ala Leu Glu Gly Val
            35                  40                  45

Gly His Phe Phe Arg Glu Leu Ala Glu Glu Lys Arg Glu Gly Ala Glu
        50                  55                  60

Arg Leu Leu Lys Leu Gln Asn Glu Arg Gly Gly Arg Ala Leu Phe Gln
 65                  70                  75                  80

Asp Val Gln Lys Pro Ser Gln Asp Glu Trp Gly Lys Thr Leu Glu Ala
                85                  90                  95

Ile Gln Ala Ala Leu Arg Leu Glu Lys Asn Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Ser His Phe Leu Asp Lys Glu Val Lys Leu Ile Lys Lys
    130                 135                 140

Met Gly Asn His Leu Thr Asn Leu Arg Arg Val Ala Gly Pro Gln Pro
145                 150                 155                 160

Val Gln Thr Gly Val Ala Gln Ala Ser Leu Gly Glu Tyr Leu Phe Glu
                165                 170                 175

Arg Leu Thr Leu Lys His Asp
            180

<210> SEQ ID NO 11
<211> LENGTH: 830
<212> TYPE: DNA
<213> ORGANISM: Rattus norvegicus

<400> SEQUENCE: 11

```
cgacagtgct tgaacggaac ccggtgctcg acccctccga ccccgccgg ccgctttgag     60
cctgagccct ttgcaacttc gtcgctccgc cgctccagcg tcgcctccgc gcctcgccca    120
gccgccatca tgaccaccgc gtctccctcg caagtgcgcc agaactacca ccaggactcg    180
gaggctgcca tcaaccgcca gatcaacctg gagttgtatg cctcctacgt ctatctgtcc    240
atgtcttgtt attttgaccg ggatgatgtg gccctgaaga actttgccaa atactttctc    300
catcaatctc atgaagagag ggaacatgct gagaaactga tgaagctgca gaaccagcga    360
ggtggacgaa tcttcctgca ggatataaag aaacctgacc gtgatgactg ggagagcggg    420
ctgaatgcaa tggagtgtgc actgcacttg aaaagagtg tgaatcagtc actactggaa    480
cttcacaaac tggctactga caagaatgat ccccacttat gtgacttcat tgagacgcat    540
tacctgaatg agcaggtgaa atccattaaa gaactgggtg accacgtgac caacttacgc    600
aagatgggag cccctgaatc tggcatggca gaatatctct ttgacaagca caccctggga    660
cacggtgatg agagctaagc tgacgtcccc aaggccatgt gactttactg gtcactgagg    720
cagtgcatgc atgtcaggct gcctttatct tttctataag ttgcaccaaa acatctgctt    780
aaaagttctt taatttgtac catttcttca aataaagaat tttggtaccc                830
```

<210> SEQ ID NO 12
<211> LENGTH: 182
<212> TYPE: PRT
<213> ORGANISM: Rattus norvegicus

<400> SEQUENCE: 12

Met Thr Thr Ala Ser Pro Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Cys Tyr Phe Asp Arg Asp Asp Val Ala
            35                  40                  45

Leu Lys Asn Phe Ala Lys Tyr Phe Leu His Gln Ser His Glu Glu Arg
        50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Arg Asp Asp Trp Glu Ser
                85                  90                  95

Gly Leu Asn Ala Met Glu Cys Ala Leu His Leu Glu Lys Ser Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

```
Ser Ile Lys Glu Leu Gly Asp His Val Thr Asn Leu Arg Lys Met Gly
145                 150                 155                 160

Ala Pro Glu Ser Gly Met Ala Glu Tyr Leu Phe Asp Lys His Thr Leu
                165                 170                 175

Gly His Gly Asp Glu Ser
            180

<210> SEQ ID NO 13
<211> LENGTH: 552
<212> TYPE: DNA
<213> ORGANISM: Rattus norvegicus

<400> SEQUENCE: 13
atgacctctc agattcgtca gaattattcc accgaagtgg aagctgccgt gaaccgcctg      60
gtcaacttgc acctgcgggc ctcttacacc tacctctctc tgggcttctt ttttgatcgg     120
gatgacgtgg ctttggaagg cgtaggccac ttcttccgcg aattggccga ggagaagcgc     180
gagggcgcca gcgtctcct caagttgcag aacgaacgcg ggggccgtgc actcttccag      240
gatgtgcaga agccatctca agatgagtgg ggtaaaaccc tggaggccat ggaagctgcc     300
ttggccctgg agaagaacct gaaccaggcc ctcttggatc tgcacgccct gggctctgcc     360
cgcacagacc ctcacctctg tgacttcttg gaaagccact tcctggataa ggaggtgaag     420
ctcatcaaga gatgggcaa ccacctgacc aacctccgta gggtgcaggg cccacaacca     480
gcgcagactg gcgtggccca ggcatctctg ggcgagtatc tctttgagcg cctcactctg     540
aagcacgact ag                                                         552

<210> SEQ ID NO 14
<211> LENGTH: 183
<212> TYPE: PRT
<213> ORGANISM: Rattus norvegicus

<400> SEQUENCE: 14

Met Thr Ser Gln Ile Arg Gln Asn Tyr Ser Thr Glu Val Glu Ala Ala
  1               5                  10                  15

Val Asn Arg Leu Val Asn Leu His Leu Arg Ala Ser Tyr Thr Tyr Leu
             20                  25                  30

Ser Leu Gly Phe Phe Phe Asp Arg Asp Asp Val Ala Leu Glu Gly Val
         35                  40                  45

Gly His Phe Phe Arg Glu Leu Ala Glu Glu Lys Arg Glu Gly Ala Glu
     50                  55                  60

Arg Leu Leu Lys Leu Gln Asn Glu Arg Gly Gly Arg Ala Leu Phe Gln
 65                  70                  75                  80

Asp Val Gln Lys Pro Ser Gln Asp Glu Trp Gly Lys Thr Leu Glu Ala
                 85                  90                  95

Met Glu Ala Ala Leu Ala Leu Glu Lys Asn Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Ser His Phe Leu Asp Lys Glu Val Lys Leu Ile Lys Lys
    130                 135                 140

Met Gly Asn His Leu Thr Asn Leu Arg Arg Val Gln Gly Pro Gln Pro
145                 150                 155                 160

Ala Gln Thr Gly Val Ala Gln Ala Ser Leu Gly Glu Tyr Leu Phe Glu
                165                 170                 175

Arg Leu Thr Leu Lys His Asp
            180
```

<210> SEQ ID NO 15
<211> LENGTH: 5010
<212> TYPE: DNA
<213> ORGANISM: Homo sapiens

<400> SEQUENCE: 15

| | | | | | |
|---|---|---|---|---|---|
| ggcggctcgg | gacggaggac | gcgctagtgt | gagtgcgggc | ttctagaact | acaccgaccc | 60 |
| tcgtgtcctc | ccttcatcct | gcggggctgg | ctggagcggc | cgctccggtg | ctgtccagca | 120 |
| gccataggga | gccgcacggg | gagcgggaaa | gcggtcgcgg | ccccaggcgg | ggcggccggg | 180 |
| atggagcggg | gccgcgagcc | tgtggggaag | gggctgtggc | ggcgcctcga | gcggctgcag | 240 |
| gttcttctgt | gtggcagttc | agaatgatgg | atcaagctag | atcagcattc | tctaacttgt | 300 |
| ttggtggaga | accattgtca | tatacccggt | tcagcctggc | tcggcaagta | gatggcgata | 360 |
| acagtcatgt | ggagatgaaa | cttgctgtag | atgaagaaga | aaatgctgac | aataacacaa | 420 |
| aggccaatgt | cacaaaacca | aaaggtgta | gtggaagtat | ctgctatggg | actattgctg | 480 |
| tgatcgtctt | tttcttgatt | ggatttatga | ttggctactt | gggctattgt | aaaggggtag | 540 |
| aaccaaaaac | tgagtgtgag | agactggcag | gaaccgagtc | tccagtgagg | gaggagccag | 600 |
| gagaggactt | ccctgcagca | cgtcgcttat | attgggatga | cctgaagaga | aagttgtcgg | 660 |
| agaaactgga | cagcacagac | ttcaccagca | ccatcaagct | gctgaatgaa | aattcatatg | 720 |
| tccctcgtga | ggctggatct | caaaaagatg | aaaatcttgc | gttgtatgtt | gaaaatcaat | 780 |
| ttcgtgaatt | taaactcagc | aaagtctggc | gtgatcaaca | ttttgttaag | attcaggtca | 840 |
| aagacagcgc | tcaaaactcg | gtgatcatag | ttgataagaa | cggtagactt | gtttacctgg | 900 |
| tggagaatcc | tggggttat | gtggcgtata | gtaaggctgc | aacagttact | ggtaaactgg | 960 |
| tccatgctaa | ttttggtact | aaaaaagatt | ttgaggattt | atacactcct | gtgaatggat | 1020 |
| ctatagtgat | tgtcagagca | gggaaaatca | cctttgcaga | aaaggttgca | aatgctgaaa | 1080 |
| gcttaaatgc | aattggtgtg | ttgatataca | tggaccagac | taaatttccc | attgttaacg | 1140 |
| cagaactttc | attctttgga | catgctcatc | tggggacagg | tgaccttac | acacctggat | 1200 |
| tccccttcctt | caatcacact | cagtttccac | catctcggtc | atcaggattg | cctaatatac | 1260 |
| ctgtccagac | aatctccaga | gctgctgcag | aaaagctgtt | tgggaatatg | aaggagact | 1320 |
| gtccctctga | ctggaaaaca | gactctacat | gtaggatggt | aacctcagaa | agcaagaatg | 1380 |
| tgaagctcac | tgtgagcaat | gtgctgaaag | agataaaaat | tcttaacatc | tttggagtta | 1440 |
| ttaaaggctt | tgtagaacca | gatcactatg | ttgtagttgg | ggcccagaga | gatgcatggg | 1500 |
| gccctggagc | tgcaaaatcc | ggtgtaggca | cagctctcct | attgaaactt | gcccagatgt | 1560 |
| tctcagatat | ggtcttaaaa | gatgggtttc | agcccagcag | aagcattatc | tttgccagtt | 1620 |
| ggagtgctgg | agactttgga | tcggttggtg | ccactgaatg | gctagaggga | tacctttcgt | 1680 |
| ccctgcattt | aaaggctttc | acttatatta | atctggataa | agcggttctt | ggtaccagca | 1740 |
| acttcaaggt | ttctgccagc | ccactgtttgt | atacgcttat | tgagaaaaca | atgcaaaatg | 1800 |
| tgaagcatcc | ggttactggg | caatttctat | atcaggacag | caactgggcc | agcaaagttg | 1860 |
| agaaactcac | tttagacaat | gctgcttttc | ctttccttgc | atattctgga | atcccagcag | 1920 |
| tttctttctg | ttttttgcgag | gacacagatt | atccttattt | gggtaccacc | atggacacct | 1980 |
| ataaggaact | gattgagagg | attcctgagt | tgaacaaagt | ggcacgagca | gctgcagagg | 2040 |
| tcgctggtca | gttcgtgatt | aaactaaccc | atgatgttga | attgaacctg | gactatgaga | 2100 |
| ggtacaacag | ccaactgctt | tcatttgtga | gggatctgaa | ccaatacaga | gcagacataa | 2160 |

```
aggaaatggg cctgagttta cagtggctgt attctgctcg tggagacttc ttccgtgcta    2220
cttccagact aacaacagat ttcgggaatg ctgagaaaac agacagattt gtcatgaaga    2280
aactcaatga tcgtgtcatg agagtggagt atcacttcct ctctccctac gtatctccaa    2340
aagagtctcc tttccgacat gtcttctggg gctccggctc tcacacgctg ccagctttac    2400
tggagaactt gaaactgcgt aaacaaaata acggtgcttt taatgaaacg ctgttcagaa    2460
accagttggc tctagctact tggactattc agggagctgc aaatgccctc tctggtgacg    2520
tttgggacat tgacaatgag ttttaaatgt gatacccata gcttccatga gaacagcagg    2580
gtagtctggt ttctagactt gtgctgatcg tgctaaattt tcagtagggc tacaaaacct    2640
gatgttaaaa ttccatccca tcatcttggt actactagat gtctttaggc agcagctttt    2700
aatacagggt agataacctg tacttcaagt taaagtgaat aaccacttaa aaaatgtcca    2760
tgatggaata ttcccctatc tctagaattt taagtgcttt gtaatgggaa ctgcctcttt    2820
cctgttgttg ttaatgaaaa tgtcagaaac cagttatgtg aatgatctct ctgaatccta    2880
agggctggtc tctgctgaag gttgtaagtg gttcgcttac tttgagtgat cctccaactt    2940
catttgatgc taaataggag ataccaggtt gaaagacctc tccaaatgag atctaagcct    3000
ttccataagg aatgtagcag gtttcctcat tcctgaaaga aacagttaac tttcagaaga    3060
gatgggcttg ttttcttgcc aatgaggtct gaaatggagg tccttctgct ggataaaatg    3120
aggttcaact gttgattgca ggaataaggc cttaatatgt taacctcagt gtcatttatg    3180
aaaagagggg accagaagcc aaagacttag tatattttct tttcctctgt cccttccccc    3240
ataagcctcc atttagttct ttgttatttt tgtttcttcc aaagcacatt gaaagagaac    3300
cagtttcagt tgtttagttg cagactcagt ttgtcagact ttaaagaata atatgctgcc    3360
aaattttggc caaagtgtta atcttagggg agagcttttct gtccttttgg cactgagata    3420
tttattgttt atttatcagt gacagagttc actataaatg gtgtttttttt aatagaatat    3480 aattatcgga agcagtgcct tccataatta tgacagttat actgtcggtt tttttttaaat    3540 aaaagcagca tctgctaata aaacccaaca gatactggaa gttttgcatt tatggtcaac    3600
acttaagggt tttagaaaac agccgtcagc caaatgtaat tgaataaagt tgaagctaag    3660
atttagagat gaattaaatt taattagggg ttgctaagaa gcgagcactg accagataag    3720
aatgctggtt ttcctaaatg cagtgaattg tgaccaagtt ataaatcaat gtcacttaaa    3780
ggctgtggta gtactcctgc aaaattttat agctcagttt atccaaggtg taactctaat    3840
tcccatttgc aaaatttcca gtacctttgt cacaatccta acacattatc gggagcagtg    3900
tcttccataa tgtataaaga acaaggtagt ttttacctac cacagtgtct gtatcggaga    3960
cagtgatctc catatgttac actaagggtg taagtaatta tcgggaacag tgtttcccat    4020
aattttcttc atgcaatgac atcttcaaag cttgaagatc gttagtatct aacatgtatc    4080
ccaactccta taattcccta tctttttagtt ttagttgcag aaacattttg tggtcattaa    4140
gcattgggtg ggtaaaattca accactgtaa aatgaaatta ctacaaaatt tgaaatttag    4200
cttgggtttt tgttaccttt atggtttctc caggtcctct acttaatgag atagcagcat    4260
acatttataa tgtttgctat tgacaagtca ttttaattta tcacattatt tgcatgttac    4320
ctcctataaa cttagtgcgg acaagtttta atccagaatt gacctttga cttaaagcag    4380 agggactttg tatagaaggt ttgggggctg tggggaagga gagtcccctg aaggtctgac    4440
acgtctgcct acccattcgt ggtgatcaat taaatgtagg tatgaataag ttcgaagctc    4500
cgtgagtgaa ccatcatata aacgtgtagt acagctgttt gtcataggge agttggaaac    4560
```

-continued

```
ggcctcctag ggaaaagttc atagggtctc ttcaggttct tagtgtcact tacctagatt    4620
tacagcctca cttgaatgtg tcactactca cagtctcttt aatcttcagt tttatcttta    4680
atctcctctt ttatcttgga ctgacattta gcgtagctaa gtgaaaaggt catagctgag    4740
attcctggtt cgggtgttac gcacacgtac ttaaatgaaa gcatgtggca tgttcatcgt    4800
ataacacaat atgaatacag gcatgcatt ttgcagcagt gagtctcttc agaaaacccct    4860 tttctacagt tagggttgag ttacttccta tcaagccagt acgtgctaac aggctcaata    4920
ttcctgaatg aaatatcaga ctagtgacaa gctcctggtc ttgagatgtc ttctcgttaa    4980
ggagtagggc cttttggagg taaaggtata                                      5010
```

<210> SEQ ID NO 16
<211> LENGTH: 760
<212> TYPE: PRT
<213> ORGANISM: Homo sapiens

<400> SEQUENCE: 16

```
Met Met Asp Gln Ala Arg Ser Ala Phe Ser Asn Leu Phe Gly Gly Glu
  1               5                  10                  15

Pro Leu Ser Tyr Thr Arg Phe Ser Leu Ala Arg Gln Val Asp Gly Asp
             20                  25                  30

Asn Ser His Val Glu Met Lys Leu Ala Val Asp Glu Glu Asn Ala
         35                  40                  45

Asp Asn Asn Thr Lys Ala Asn Val Thr Lys Pro Lys Arg Cys Ser Gly
     50                  55                  60

Ser Ile Cys Tyr Gly Thr Ile Ala Val Ile Val Phe Phe Leu Ile Gly
 65                  70                  75                  80

Phe Met Ile Gly Tyr Leu Gly Tyr Cys Lys Gly Val Glu Pro Lys Thr
                 85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Ser Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
```

```
            290                 295                 300
Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
                340                 345                 350

Cys Pro Ser Asp Trp Lys Thr Asp Ser Thr Cys Arg Met Val Thr Ser
                355                 360                 365

Glu Ser Lys Asn Val Lys Leu Thr Val Ser Asn Val Leu Lys Glu Ile
370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Lys Leu Ala Gln Met
                420                 425                 430

Phe Ser Asp Met Val Leu Lys Asp Gly Phe Gln Pro Ser Arg Ser Ile
                435                 440                 445

Ile Phe Ala Ser Trp Ser Ala Gly Asp Phe Gly Ser Val Gly Ala Thr
                450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
                500                 505                 510

Val Lys His Pro Val Thr Gly Gln Phe Leu Tyr Gln Asp Ser Asn Trp
                515                 520                 525

Ala Ser Lys Val Glu Lys Leu Thr Leu Asp Asn Ala Ala Phe Pro Phe
530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
                580                 585                 590

Val Ala Gly Gln Phe Val Ile Lys Leu Thr His Asp Val Glu Leu Asn
                595                 600                 605

Leu Asp Tyr Glu Arg Tyr Asn Ser Gln Leu Leu Ser Phe Val Arg Asp
610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
                660                 665                 670

Lys Leu Asn Asp Arg Val Met Arg Val Glu Tyr His Phe Leu Ser Pro
                675                 680                 685

Tyr Val Ser Pro Lys Glu Ser Pro Phe Arg His Val Phe Trp Gly Ser
                690                 695                 700

Gly Ser His Thr Leu Pro Ala Leu Leu Glu Asn Leu Lys Leu Arg Lys
705                 710                 715                 720
```

```
Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 17
<211> LENGTH: 2513
<212> TYPE: DNA
<213> ORGANISM: Homo sapiens

<400> SEQUENCE: 17
```

| | | | | | |
|---|---|---|---|---|---|
| ctgcaggctt | caggagggga | cacaagcatg | gagcggcttt | ggggtctatt | ccagagagcg | 60 |
| caacaactgt | ccccaagatc | ctctcagacc | gtctaccagc | gtgtggaagg | ccccggaaa | 120 |
| gggcacctgg | aggaggaaga | ggaagacggg | gaggaggggg | cggagacatt | ggcccacttc | 180 |
| tgccccatgg | agctgagggg | ccctgagccc | ctgggctcta | gacccaggca | gccaaacctc | 240 |
| attccctggg | cggcagcagg | acggagggct | gccccctacc | tggtcctgac | ggccctgctg | 300 |
| atcttcactg | gggccttcct | actgggctac | gtcgccttcc | gagggtcctg | ccaggcgtgc | 360 |
| ggagactctg | tgttggtggt | cagtgaggat | gtcaactatg | agcctgacct | ggatttccac | 420 |
| cagggcagac | tctactggag | cgacctccag | gccatgttcc | tgcagttcct | ggggagggg | 480 |
| cgcctggagg | acaccatcag | gcaaaccagc | cttcgggaac | gggtggcagg | ctcggccggg | 540 |
| atggccgctc | tgactcagga | cattcgcgcg | gcgctctccc | gccagaagct | ggaccacgtg | 600 |
| tggaccgaca | cgcactacgt | ggggctgcaa | ttcccggatc | cggctcaccc | caacaccctg | 660 |
| cactgggtcg | atgaggccgg | gaaggtcgga | gagcagctgc | cgctggagga | ccctgacgtc | 720 |
| tactgcccct | acagcgccat | cggcaacgtc | acgggagagc | tggtgtacgc | ccactacggg | 780 |
| cggcccgaag | acctgcagga | cctgcgggcc | aggggcgtgg | atccagtggg | ccgcctgctg | 840 |
| ctggtgcgcg | tggggtgat | cagcttcgcc | cagaaggtga | ccaatgctca | ggacttcggg | 900 |
| gctcaaggag | tgctcatata | cccagagcca | gcggacttct | cccaggaccc | acccaagcca | 960 |
| agcctgtcca | gccagcaggc | agtgtatgga | catgtgcacc | tgggaactgg | agacccctac | 1020 |
| acacctggct | tcccttcctt | caatcaaacc | cagaagctca | aaggccctgt | ggccccccaa | 1080 |
| gaatggcagg | ggagcctcct | aggctcccct | tatcacctgg | gccccgggcc | acgactgcgg | 1140 |
| ctagtggtca | caatcacag | gacctccacc | cccatcaaca | acatcttcgg | ctgcatcgaa | 1200 |
| ggccgctcag | agccagatca | ctacgttgtc | atcggggccc | agagggatgc | atggggccca | 1260 |
| ggagcagcta | aatccgctgt | ggggacggct | atactcctgg | agctggtgcg | gaccttttcc | 1320 |
| tccatggtga | gcaacggctt | ccggccccgc | agaagtctcc | tcttcatcag | ctgggacggt | 1380 |
| ggtgactttg | gaagcgtggg | ctccacggag | tggctagagg | gctacctcag | cgtgctgcac | 1440 |
| ctcaaagccg | tagtgtacgt | gagcctggac | aacgcagtgc | tggggatga | caagtttcat | 1500 |
| gccaagacca | ccccccttct | gacaagtctc | attgagagtg | tcctgaagca | ggtggattct | 1560 |
| cccaaccaca | gtgggcagac | tctctatgaa | caggtggtgt | tcaccaatcc | cagctgggat | 1620 |
| gctgaggtga | tccggccccc | tacccatggaa | agcagtgcct | attccttcac | ggcctttgtg | 1680 |
| ggagtccctg | ccgtcgagtt | ctcctttatg | gaggacgacc | aggcctaccc | attcctgcac | 1740 |
| acaaaggagg | acacttatga | gaacctgcat | aaggtgctgc | aaggccgcct | gccgccgtg | 1800 |
| gcccaggcca | tgcccagct | cgcagggcag | ctcctcatcc | ggctcagcca | cgatcgcctg | 1860 |
| ctgcccctcg | acttcggccg | ctacggggac | gtcgtcctca | ggcacatcgg | gaacctcaac | 1920 |

```
gagttctctg gggacctcaa ggcccgcggg ctgaccctgc agtgggtgta ctcggcgcgg     1980
ggggactaca tccgggcggc ggaaaagctg cggcaggaga tctacagctc ggaggagaga     2040
gacgagcgac tgacacgcat gtacaacgtg cgcataatgc ggatccccct ctctgcgcag     2100
gtggagttct acttcctttc ccagtacgtg tcgccagccg actcccgtt ccgccacatc      2160 ttcatgggcc gtggagacca cacgctgggc gccctgctgg accacctgcg gctgctgcgc     2220
tccaacagct ccgggacccc cggggccacc tcctccactg gcttccagga gagccgtttc     2280
cggcgtcagc tagccctgct cacctggacg ctgcaagggg cagccaatgc gcttagcggg     2340
gatgtctgga acattgataa caacttctga ggccctgggg atcctcacat ccccgtcccc     2400
cagtcaagag ctcctctgct cctcgcttga atgattcagg gtcagggagg tggctcagag     2460
tccacctctc attgctgatc aatttctcat taccccctaca catctctcca cgg            2513
```

<210> SEQ ID NO 18
<211> LENGTH: 780
<212> TYPE: PRT
<213> ORGANISM: Homo sapiens

<400> SEQUENCE: 18

```
Met Glu Arg Leu Trp Gly Leu Phe Gln Arg Ala Gln Gln Leu Ser Pro
 1               5                  10                  15

Arg Ser Ser Gln Thr Val Tyr Gln Arg Val Glu Gly Pro Arg Lys Gly
                20                  25                  30

His Leu Glu Glu Glu Glu Asp Gly Glu Glu Gly Ala Glu Thr Leu
            35                  40                  45

Ala His Phe Cys Pro Met Glu Leu Arg Gly Pro Glu Pro Leu Gly Ser
        50                  55                  60

Arg Pro Arg Gln Pro Asn Leu Ile Pro Trp Ala Ala Gly Arg Arg
 65                  70                  75                  80

Ala Ala Pro Tyr Leu Val Leu Thr Ala Leu Leu Ile Phe Thr Gly Ala
                85                  90                  95

Phe Leu Leu Gly Tyr Val Ala Phe Arg Gly Ser Cys Gln Ala Cys Gly
            100                 105                 110

Asp Ser Val Leu Val Val Ser Glu Asp Val Asn Tyr Glu Pro Asp Leu
        115                 120                 125

Asp Phe His Gln Gly Arg Leu Tyr Trp Ser Asp Leu Gln Ala Met Phe
    130                 135                 140

Leu Gln Phe Leu Gly Glu Gly Arg Leu Glu Asp Thr Ile Arg Gln Thr
145                 150                 155                 160

Ser Leu Arg Glu Arg Val Ala Gly Ser Ala Gly Met Ala Ala Leu Thr
                165                 170                 175

Gln Asp Ile Arg Ala Ala Leu Ser Arg Gln Lys Leu Asp His Val Trp
            180                 185                 190

Thr Asp Thr His Tyr Val Gly Leu Gln Phe Pro Asp Pro Ala His Pro
        195                 200                 205

Asn Thr Leu His Trp Val Asp Glu Ala Gly Lys Val Gly Glu Gln Leu
    210                 215                 220

Pro Leu Glu Asp Pro Asp Val Tyr Cys Pro Tyr Ser Ala Ile Gly Asn
225                 230                 235                 240

Val Thr Gly Glu Leu Val Tyr Ala His Tyr Gly Arg Pro Glu Asp Leu
                245                 250                 255

Gln Asp Leu Arg Ala Arg Gly Val Asp Pro Val Gly Arg Leu Leu Leu
            260                 265                 270
```

-continued

```
Val Arg Val Gly Val Ile Ser Phe Ala Gln Lys Val Thr Asn Ala Gln
        275                 280                 285

Asp Phe Gly Ala Gln Gly Val Leu Ile Tyr Pro Glu Pro Ala Asp Phe
    290                 295                 300

Ser Gln Asp Pro Pro Lys Pro Ser Leu Ser Ser Gln Gln Ala Val Tyr
305                 310                 315                 320

Gly His Val His Leu Gly Thr Gly Asp Pro Tyr Thr Pro Gly Phe Pro
                325                 330                 335

Ser Phe Asn Gln Thr Gln Lys Leu Lys Gly Pro Val Ala Pro Gln Glu
                    340                 345                 350

Trp Gln Gly Ser Leu Leu Gly Ser Pro Tyr His Leu Gly Pro Gly Pro
                355                 360                 365

Arg Leu Arg Leu Val Val Asn Asn His Arg Thr Ser Thr Pro Ile Asn
    370                 375                 380

Asn Ile Phe Gly Cys Ile Glu Gly Arg Ser Glu Pro Asp His Tyr Val
385                 390                 395                 400

Val Ile Gly Ala Gln Arg Asp Ala Trp Gly Pro Gly Ala Ala Lys Ser
                405                 410                 415

Ala Val Gly Thr Ala Ile Leu Leu Glu Leu Val Arg Thr Phe Ser Ser
                420                 425                 430

Met Val Ser Asn Gly Phe Arg Pro Arg Arg Ser Leu Leu Phe Ile Ser
                435                 440                 445

Trp Asp Gly Gly Asp Phe Gly Ser Val Gly Ser Thr Glu Trp Leu Glu
    450                 455                 460

Gly Tyr Leu Ser Val Leu His Leu Lys Ala Val Val Tyr Val Ser Leu
465                 470                 475                 480

Asp Asn Ala Val Leu Gly Asp Asp Lys Phe His Ala Lys Thr Ser Pro
                485                 490                 495

Leu Leu Thr Ser Leu Ile Glu Ser Val Leu Lys Gln Val Asp Ser Pro
                500                 505                 510

Asn His Ser Gly Gln Thr Leu Tyr Glu Gln Val Val Phe Thr Asn Pro
    515                 520                 525

Ser Trp Asp Ala Glu Val Ile Arg Pro Leu Pro Met Asp Ser Ser Ala
530                 535                 540

Tyr Ser Phe Thr Ala Phe Val Gly Val Pro Ala Val Glu Phe Ser Phe
545                 550                 555                 560

Met Glu Asp Asp Gln Ala Tyr Pro Phe Leu His Thr Lys Glu Asp Thr
                565                 570                 575

Tyr Glu Asn Leu His Lys Val Leu Gln Gly Arg Leu Pro Ala Val Ala
                580                 585                 590

Gln Ala Val Ala Gln Leu Ala Gly Gln Leu Leu Ile Arg Leu Ser His
                595                 600                 605

Asp Arg Leu Leu Pro Leu Asp Phe Gly Arg Tyr Gly Asp Val Val Leu
    610                 615                 620

Arg His Ile Gly Asn Leu Asn Glu Phe Ser Gly Asp Leu Lys Ala Arg
625                 630                 635                 640

Gly Leu Thr Leu Gln Trp Val Tyr Ser Ala Arg Gly Asp Tyr Ile Arg
                645                 650                 655

Ala Ala Glu Lys Leu Arg Gln Glu Ile Tyr Ser Ser Glu Glu Arg Asp
                660                 665                 670

Glu Arg Leu Thr Arg Met Tyr Asn Val Arg Ile Met Arg Ile Pro Leu
    675                 680                 685

Ser Ala Gln Val Glu Phe Tyr Phe Leu Ser Gln Tyr Val Ser Pro Ala
690                 695                 700
```

Asp Ser Pro Phe Arg His Ile Phe Met Gly Arg Gly Asp His Thr Leu
705                 710                 715                 720

Gly Ala Leu Leu Asp His Leu Arg Leu Leu Arg Ser Asn Ser Ser Gly
            725                 730                 735

Thr Pro Gly Ala Thr Ser Ser Thr Gly Phe Gln Glu Ser Arg Phe Arg
        740                 745                 750

Arg Gln Leu Ala Leu Leu Thr Trp Thr Leu Gln Gly Ala Ala Asn Ala
    755                 760                 765

Leu Ser Gly Asp Val Trp Asn Ile Asp Asn Asn Phe
770                 775                 780

<210> SEQ ID NO 19
<211> LENGTH: 2292
<212> TYPE: DNA
<213> ORGANISM: Mus musculus

<400> SEQUENCE: 19

| | | | | | |
|---|---|---|---|---|---|
| atgatggatc | aagccagatc | agcattctct | aacttgtttg | gtggggaacc | attgtcatac | 60 |
| acccggttta | gccttgctcg | gcaagtagat | ggagataaca | gtcatgtgga | gatgaaactg | 120 |
| gctgcagatg | aagaagaaaa | tgccgacaat | aacatgaagg | ctagtgtcag | aaacccaag | 180 |
| aggtttaatg | aagactctg | cttttgcagct | attgcactag | tcattttctt | cttgattgga | 240 |
| ttcatgagtg | gctacctggg | ctattgtaag | cgtgtagaac | aaaaagagga | gtgtgtgaaa | 300 |
| ctggctgaaa | cggaggagac | agacaagtca | gaaaccatgg | aaacagagga | tgttcctaca | 360 |
| tcatctcgct | tatattgggc | agacctcaaa | acactgttgt | cagagaagtt | gaactccata | 420 |
| gagtttgctg | acaccatcaa | gcagctgagc | cagaatacat | acactcctcg | tgaggctgga | 480 |
| tctcaaaaag | atgaaagtct | tgcctattat | attgaaaatc | agttccatga | atttaaattc | 540 |
| agcaaagtct | ggcgagatga | acactatgtg | aagattcaag | tgaaaagcag | cattggtcaa | 600 |
| aacatggtga | ccatagtgca | gtcaaatggt | aacttagacc | cagtggagtc | tcccgagggt | 660 |
| tatgtggcat | tcagtaaacc | tacagaagtt | tctggtaaac | tggtccatgc | taattttggc | 720 |
| actaaaaagg | actttgaaga | actaagttat | tctgtgaatg | gatctttagt | gattgttaga | 780 |
| gcagggaaa | ttacttttgc | agaaaaggtt | gcaaatgccc | aaagctttaa | tgcaattggt | 840 |
| gtcctcatat | acatggacaa | gaataaattc | cccgttgttg | aggcagacct | tgcactcttt | 900 |
| ggacatgctc | atctaggaac | tggtgatcca | tacacacctg | gctttccttc | tttcaatcat | 960 |
| actcagtttc | cgccatctca | gtcatcaggg | ttgcctaata | tacctgtgca | aacaatctca | 1020 |
| agagctgctg | cagaaaagct | atttggaaaa | atggaaggaa | gctgtcctgc | tagatggaac | 1080 |
| atagattctt | catgtaagct | ggaactttca | cagaatcaaa | atgtgaagct | cattgtgaaa | 1140 |
| aacgtactga | agaaagaag | aatacttaac | atctttggag | ttattaaagg | ttatgaggaa | 1200 |
| ccagaccgtt | atgttgtagt | aggagcccag | agagacgctt | gggtgctgg | tgttgcggcg | 1260 |
| aagtccagtg | tgggaacagg | tcttctgttg | aaacttgccc | aagtattctc | agatatgatt | 1320 |
| tcaaaagatg | gatttagacc | cagcagaagt | ataatctttg | ccagctggac | tgcaggcgac | 1380 |
| tttggagctg | ttggtgccac | tgagtggttg | gagggatacc | tttcatcttt | gcatttaaaa | 1440 |
| gctttcactt | atattaattt | ggataaagtt | gtccttggta | ctagtaactt | caaagtttct | 1500 |
| gccagccct | tattatatac | acttatggga | aagataatgc | aagatgtaaa | gcatccagtt | 1560 |
| gatggaaaat | ctctatatag | agacagcaat | tggattagca | agttgagaa | actttccttt | 1620 |
| gacaatgctg | catatccttt | ccttgcatat | tctggaatcc | cagcagtttc | ttttttgtttt | 1680 |

```
tgtgaggatg cagactatcc ttatttgggc actagattgg ataccctatga ggcattgact    1740 cagaaagttc ctcagctcaa ccaaatggtt cgtacagcag cggaagtggc tggtcagctc    1800
attattaaac ttacccatga cgttgaattg aacctggact atgagatgta acagcaaa     1860 ctactgtcat ttatgaagga tctgaaccag ttcaaaacag atatcaggga tatgggtcta    1920
agtctacagt ggctgtattc cgctcgtgga gactacttcc gtgctacttc tagactaaca    1980
actgattttc ataatgctga gaaacaaac agatttgtca tgagggaaat caatgatcgt     2040
attatgaaag tggagtatca cttcctgtcg ccctatgtat ctccaagaga gtctcctttc    2100
cgacatatct tctggggctc tggctctcac actctctcag ctttagtgga aacttgaag     2160 cttcgtcaaa aaatattac tgcttttaat gaaaccctct tcagaaacca gttggccctg    2220
gctacttgga ctattcaggg agtcgcaaat gccctctctg gtgacatttg gaatattgac    2280
aatgagtttt aa                                                        2292

<210> SEQ ID NO 20
<211> LENGTH: 763
<212> TYPE: PRT
<213> ORGANISM: Mus musculus

<400> SEQUENCE: 20

Met Met Asp Gln Ala Arg Ser Ala Phe Ser Asn Leu Phe Gly Gly Glu
  1               5                  10                  15

Pro Leu Ser Tyr Thr Arg Phe Ser Leu Ala Arg Gln Val Asp Gly Asp
                 20                  25                  30

Asn Ser His Val Glu Met Lys Leu Ala Ala Asp Glu Glu Asn Ala
             35                  40                  45

Asp Asn Asn Met Lys Ala Ser Val Arg Lys Pro Lys Arg Phe Asn Gly
         50                  55                  60

Arg Leu Cys Phe Ala Ala Ile Ala Leu Val Ile Phe Phe Leu Ile Gly
 65                  70                  75                  80

Phe Met Ser Gly Tyr Leu Gly Tyr Cys Lys Arg Val Glu Gln Lys Glu
                 85                  90                  95

Glu Cys Val Lys Leu Ala Glu Thr Glu Thr Asp Lys Ser Glu Thr
            100                 105                 110

Met Glu Thr Glu Asp Val Pro Thr Ser Ser Arg Leu Tyr Trp Ala Asp
            115                 120                 125

Leu Lys Thr Leu Leu Ser Glu Lys Leu Asn Ser Ile Glu Phe Ala Asp
        130                 135                 140

Thr Ile Lys Gln Leu Ser Gln Asn Thr Tyr Thr Pro Arg Glu Ala Gly
145                 150                 155                 160

Ser Gln Lys Asp Glu Ser Leu Ala Tyr Tyr Ile Glu Asn Gln Phe His
                165                 170                 175

Glu Phe Lys Phe Ser Lys Val Trp Arg Asp Glu His Tyr Val Lys Ile
            180                 185                 190

Gln Val Lys Ser Ser Ile Gly Gln Asn Met Val Thr Ile Val Gln Ser
        195                 200                 205

Asn Gly Asn Leu Asp Pro Val Glu Ser Pro Glu Gly Tyr Val Ala Phe
    210                 215                 220

Ser Lys Pro Thr Glu Val Ser Gly Lys Leu Val His Ala Asn Phe Gly
225                 230                 235                 240

Thr Lys Lys Asp Phe Glu Glu Leu Ser Tyr Ser Val Asn Gly Ser Leu
                245                 250                 255

Val Ile Val Arg Ala Gly Glu Ile Thr Phe Ala Glu Lys Val Ala Asn
            260                 265                 270
```

```
Ala Gln Ser Phe Asn Ala Ile Gly Val Leu Ile Tyr Met Asp Lys Asn
        275                 280                 285

Lys Phe Pro Val Val Glu Ala Asp Leu Ala Leu Phe Gly His Ala His
        290                 295                 300

Leu Gly Thr Gly Asp Pro Tyr Thr Pro Gly Phe Pro Ser Phe Asn His
305                     310                 315                 320

Thr Gln Phe Pro Pro Ser Gln Ser Ser Gly Leu Pro Asn Ile Pro Val
                325                 330                 335

Gln Thr Ile Ser Arg Ala Ala Glu Lys Leu Phe Gly Lys Met Glu
        340                 345                 350

Gly Ser Cys Pro Ala Arg Trp Asn Ile Asp Ser Ser Cys Lys Leu Glu
        355                 360                 365

Leu Ser Gln Asn Gln Asn Val Lys Leu Ile Val Lys Asn Val Leu Lys
        370                 375                 380

Glu Arg Arg Ile Leu Asn Ile Phe Gly Val Ile Lys Gly Tyr Glu Glu
385                     390                 395                 400

Pro Asp Arg Tyr Val Val Gly Ala Gln Arg Asp Ala Leu Gly Ala
                405                 410                 415

Gly Val Ala Ala Lys Ser Ser Val Gly Thr Gly Leu Leu Leu Lys Leu
        420                 425                 430

Ala Gln Val Phe Ser Asp Met Ile Ser Lys Asp Gly Phe Arg Pro Ser
        435                 440                 445

Arg Ser Ile Ile Phe Ala Ser Trp Thr Ala Gly Asp Phe Gly Ala Val
        450                 455                 460

Gly Ala Thr Glu Trp Leu Glu Gly Tyr Leu Ser Ser Leu His Leu Lys
465                     470                 475                 480

Ala Phe Thr Tyr Ile Asn Leu Asp Lys Val Val Leu Gly Thr Ser Asn
                485                 490                 495

Phe Lys Val Ser Ala Ser Pro Leu Leu Tyr Thr Leu Met Gly Lys Ile
        500                 505                 510

Met Gln Asp Val Lys His Pro Val Asp Gly Lys Ser Leu Tyr Arg Asp
        515                 520                 525

Ser Asn Trp Ile Ser Lys Val Glu Lys Leu Ser Phe Asp Asn Ala Ala
        530                 535                 540

Tyr Pro Phe Leu Ala Tyr Ser Gly Ile Pro Ala Val Ser Phe Cys Phe
545                     550                 555                 560

Cys Glu Asp Ala Asp Tyr Pro Tyr Leu Gly Thr Arg Leu Asp Thr Tyr
                565                 570                 575

Glu Ala Leu Thr Gln Lys Val Pro Gln Leu Asn Gln Met Val Arg Thr
        580                 585                 590

Ala Ala Glu Val Ala Gly Gln Leu Ile Ile Lys Leu Thr His Asp Val
        595                 600                 605

Glu Leu Asn Leu Asp Tyr Glu Met Tyr Asn Ser Lys Leu Leu Ser Phe
610                     615                 620

Met Lys Asp Leu Asn Gln Phe Lys Thr Asp Ile Arg Asp Met Gly Leu
625                     630                 635                 640

Ser Leu Gln Trp Leu Tyr Ser Ala Arg Gly Asp Tyr Phe Arg Ala Thr
                645                 650                 655

Ser Arg Leu Thr Thr Asp Phe His Asn Ala Glu Lys Thr Asn Arg Phe
        660                 665                 670

Val Met Arg Glu Ile Asn Asp Arg Ile Met Lys Val Glu Tyr His Phe
        675                 680                 685

Leu Ser Pro Tyr Val Ser Pro Arg Glu Ser Pro Phe Arg His Ile Phe
```

```
                690             695             700
Trp Gly Ser Gly Ser His Thr Leu Ser Ala Leu Val Glu Asn Leu Lys
705                 710                 715                 720

Leu Arg Gln Lys Asn Ile Thr Ala Phe Asn Glu Thr Leu Phe Arg Asn
                725                 730                 735

Gln Leu Ala Leu Ala Thr Trp Thr Ile Gln Gly Val Ala Asn Ala Leu
            740                 745                 750

Ser Gly Asp Ile Trp Asn Ile Asp Asn Glu Phe
            755                 760

<210> SEQ ID NO 21
<211> LENGTH: 2859
<212> TYPE: DNA
<213> ORGANISM: Mus musculus

<400> SEQUENCE: 21
```

| | | | | | |
|---|---|---|---|---|---|
| aaaaaaaaaa | attgattgtt | ttgcagtctg | cccgcaacag | tggggtttgt | ggaaagattg | 60 |
| agttcaggag | ggggcacaag | catggagcaa | cgttggggtc | tacttcggag | agtgcaacag | 120 |
| tggtccccaa | gaccctctca | gaccatctac | agacgcgtgg | aaggccctca | gctgagcac | 180 |
| ctggaggagg | aagacaggga | ggaaggggcg | gagcttcctg | cccagttctg | ccccatggaa | 240 |
| ctcaaaggcc | ctgagcactt | aggctcctgt | cccgggaggt | caattcccat | accctgggct | 300 |
| gcagcaggtc | gaaaggctgc | ccctatctg | gtcctgatca | ccctgctaat | cttcactggg | 360 |
| gccttcctcc | taggctacgt | ggcctttcga | gggtcctgcc | aggcgtgtgg | ggactccgtg | 420 |
| ttggtggtcg | atgaagatgt | caaccctgag | gactccggcc | ggaccacgtt | gtactggagc | 480 |
| gacctccagg | ccatgtttct | ccggttcctt | ggggaggggc | gcatggaaga | caccatcagg | 540 |
| ctgaccagcc | tccgggaacg | cgtggctggc | tcagccagaa | tggccaccct | ggtccaagat | 600 |
| atcctcgata | gctctcgcg | ccagaagctg | gaccacgtgt | ggactgacac | gcactacgtg | 660 |
| ggacttcagt | tcccagatcc | ggctcacgct | aacaccctgc | actgggtgga | tgcagacggg | 720 |
| agcgtccagg | agcagctacc | gctggaggat | ccggaagtct | actgtcccta | cagcgccacc | 780 |
| ggcaacgcca | cgggcaagct | ggtgtacgcc | cactacgggc | ggtcgaggga | cctacaggac | 840 |
| ctaaaagcca | agggcgtgga | gctggccggc | agcctcctgc | tagtgcgagt | tggaattact | 900 |
| agcttcgccc | agaaggtagc | cgttgcccag | gactttgggg | ctcaaggagt | gctgatatac | 960 |
| cctgacccat | cagacttctc | ccaggatccc | cacaagccag | gcctgtctag | ccaccaggct | 1020 |
| gtgtacggac | atgtgcacct | gggaactgga | gaccccttaca | cacctggctt | cccgtccttc | 1080 |
| aatcaaaccc | agttccctcc | agtagaatca | tcaggccttc | ccagcatccc | cgcccagccc | 1140 |
| atcagtgctg | acattgctga | tcaattgctc | aggaaaactca | caggcccgt | ggctccccag | 1200 |
| gagtggaaag | gtcacctctc | aggctctcct | tatcggctgg | gacctgggcc | cgacttacgc | 1260 |
| cttgtggtca | caaccacag | agtctctacc | cccatcagta | acatctttgc | gtgcatcgag | 1320 |
| ggctttgcag | agccagatca | ctatgttgtc | attggggccc | agagggatgc | atggggccca | 1380 |
| ggagcagcca | agtctgcagt | ggggactgcc | atcctgctgg | agctggttcg | gaccttctct | 1440 |
| tccatggtca | gcaatgggtt | cagacctcga | agaagtcttt | tgttcattag | ctgggacgga | 1500 |
| ggtgactttg | gcagcgtggg | agccacagag | tggttgagg | gctacctcag | cgtgctacac | 1560 |
| ctcaaagctg | ttgtgtacgt | gagcctggac | aactccgtgt | gggagatgg | caaattccat | 1620 |
| gctaagacca | gccccttcct | cgtcagcctc | attgagaata | tcttgaagca | ggtggactcc | 1680 |
| cctaaccata | gtgacagac | cctctatgaa | caagtggcac | tcacccaccc | cagctgggat | 1740 |

```
gctgaagtga ttcagcccct gcccatggac agcagtgcat attccttcac agcctttgcg    1800
ggggtcccag ctgtggagtt ctccttcatg gaggatgatc gggtgtaccc attcctgcac    1860
acggaggagg acacatatga gaatctgcac aagatgctgc gaggtcgcct gccgccgtg     1920 gtccaggcag tggctcagct cgcgggccag ctcctcatcc gactgagcca cgatcaccta    1980
ctgccgctag acttcggccg ctatggagac gtggttctca ggcacatcgg caacctcaat    2040
gagttctctg ggaccctcaa ggagcgcggg ctgaccctgc agtgggtgta ctctgcaagg    2100
ggggactaca tccgtgcggc ggaaaagctg cggaaggaga tctacagctc ggagcggaac    2160
gatgagcgtc tgatgcgcat gtacaacgtg cgcatcatga gggtggagtt ctacttcctg    2220
tcccagtatg tgtcgccagc cgactcccca ttccgccaca ttttcctagg ccaaggcgac    2280
cacactttgg gtgccctggt agaccacctg cggatgctgc gcgccgatgg ctcaggagcc    2340
gcctcttccc ggttgacagc aggtctgggc ttccaggaga gtcgcttccg gcgccagctg    2400
gcgctgctca cctggacact gcaggggca gccaacgctc tcagtggcga cgtttggaac     2460
attgacaata acttttgaag ccaaaagccc tccatgggcc cacgtgatt ctccttctc      2520 cctctttgag tggtgcaggc aaaggaggtg cctgagattg taacctattc ttaacaccct    2580
tggtcctgca atgctggtgc gccatatttt ctcagtgtgg ttgtcatgcc gttgcttacc    2640
cagaaagcgg ttttcttccc atcacaggcc cttctgtctt caggagcaaa gttccccata    2700
tctagagact atctagatgc tgggatctga tcagctctct tagagagtga gatggacagc    2760
gtcattattt tatgacacat gagctacggt atgtgagcag cccaagggga ttagatgtca    2820
ataaaccaat tgtaaccca aaaaaaaaaa aaaaaaaa                             2859
```

<210> SEQ ID NO 22  
<211> LENGTH: 798  
<212> TYPE: PRT  
<213> ORGANISM: Mus musculus

<400> SEQUENCE: 22

```
Met Glu Gln Arg Trp Gly Leu Leu Arg Arg Val Gln Gln Trp Ser Pro
 1               5                  10                  15

Arg Pro Ser Gln Thr Ile Tyr Arg Arg Val Glu Gly Pro Gln Leu Glu
            20                  25                  30

His Leu Glu Glu Glu Asp Arg Glu Gly Ala Glu Leu Pro Ala Gln
        35                  40                  45

Phe Cys Pro Met Glu Leu Lys Gly Pro Glu His Leu Gly Ser Cys Pro
    50                  55                  60

Gly Arg Ser Ile Pro Ile Pro Trp Ala Ala Ala Gly Arg Lys Ala Ala
65                  70                  75                  80

Pro Tyr Leu Val Leu Ile Thr Leu Leu Ile Phe Thr Gly Ala Phe Leu
                85                  90                  95

Leu Gly Tyr Val Ala Phe Arg Gly Ser Cys Gln Ala Cys Gly Asp Ser
            100                 105                 110

Val Leu Val Val Asp Glu Asp Val Asn Pro Glu Asp Ser Gly Arg Thr
        115                 120                 125

Thr Leu Tyr Trp Ser Asp Leu Gln Ala Met Phe Leu Arg Phe Leu Gly
    130                 135                 140

Glu Gly Arg Met Glu Asp Thr Ile Arg Leu Thr Ser Leu Arg Glu Arg
145                 150                 155                 160

Val Ala Gly Ser Ala Arg Met Ala Thr Leu Val Gln Asp Ile Leu Asp
                165                 170                 175

Lys Leu Ser Arg Gln Lys Leu Asp His Val Trp Thr Asp Thr His Tyr
```

```
                180             185             190
Val Gly Leu Gln Phe Pro Asp Pro Ala His Ala Asn Thr Leu His Trp
        195                 200                 205
Val Asp Ala Asp Gly Ser Val Gln Glu Gln Leu Pro Leu Glu Asp Pro
        210                 215                 220
Glu Val Tyr Cys Pro Tyr Ser Ala Thr Gly Asn Ala Thr Gly Lys Leu
225                 230                 235                 240
Val Tyr Ala His Tyr Gly Arg Ser Glu Asp Leu Gln Asp Leu Lys Ala
                245                 250                 255
Lys Gly Val Glu Leu Ala Gly Ser Leu Leu Leu Val Arg Val Gly Ile
                260                 265                 270
Thr Ser Phe Ala Gln Lys Val Ala Val Ala Gln Asp Phe Gly Ala Gln
            275                 280                 285
Gly Val Leu Ile Tyr Pro Asp Pro Ser Asp Phe Ser Gln Asp Pro His
        290                 295                 300
Lys Pro Gly Leu Ser Ser His Gln Ala Val Tyr Gly His Val His Leu
305                 310                 315                 320
Gly Thr Gly Asp Pro Tyr Thr Pro Gly Phe Pro Ser Phe Asn Gln Thr
                325                 330                 335
Gln Phe Pro Pro Val Glu Ser Ser Gly Leu Pro Ser Ile Pro Ala Gln
                340                 345                 350
Pro Ile Ser Ala Asp Ile Ala Asp Gln Leu Leu Arg Lys Leu Thr Gly
            355                 360                 365
Pro Val Ala Pro Gln Glu Trp Lys Gly His Leu Ser Gly Ser Pro Tyr
        370                 375                 380
Arg Leu Gly Pro Gly Pro Asp Leu Arg Leu Val Val Asn Asn His Arg
385                 390                 395                 400
Val Ser Thr Pro Ile Ser Asn Ile Phe Ala Cys Ile Glu Gly Phe Ala
                405                 410                 415
Glu Pro Asp His Tyr Val Val Ile Gly Ala Gln Arg Asp Ala Trp Gly
                420                 425                 430
Pro Gly Ala Ala Lys Ser Ala Val Gly Thr Ala Ile Leu Leu Glu Leu
        435                 440                 445
Val Arg Thr Phe Ser Ser Met Val Ser Asn Gly Phe Arg Pro Arg Arg
        450                 455                 460
Ser Leu Leu Phe Ile Ser Trp Asp Gly Gly Asp Phe Gly Ser Val Gly
465                 470                 475                 480
Ala Thr Glu Trp Leu Glu Gly Tyr Leu Ser Val Leu His Leu Lys Ala
                485                 490                 495
Val Val Tyr Val Ser Leu Asp Asn Ser Val Leu Gly Asp Gly Lys Phe
            500                 505                 510
His Ala Lys Thr Ser Pro Leu Leu Val Ser Leu Ile Glu Asn Ile Leu
        515                 520                 525
Lys Gln Val Asp Ser Pro Asn His Ser Gly Gln Thr Leu Tyr Glu Gln
        530                 535                 540
Val Ala Leu Thr His Pro Ser Trp Asp Ala Glu Val Ile Gln Pro Leu
545                 550                 555                 560
Pro Met Asp Ser Ser Ala Tyr Ser Phe Thr Ala Phe Ala Gly Val Pro
                565                 570                 575
Ala Val Glu Phe Ser Phe Met Glu Asp Asp Arg Val Tyr Pro Phe Leu
                580                 585                 590
His Thr Glu Glu Asp Thr Tyr Glu Asn Leu His Lys Met Leu Arg Gly
            595                 600                 605
```

```
Arg Leu Pro Ala Val Val Gln Ala Val Ala Gln Leu Ala Gly Gln Leu
    610                 615                 620

Leu Ile Arg Leu Ser His Asp His Leu Leu Pro Leu Asp Phe Gly Arg
625                 630                 635                 640

Tyr Gly Asp Val Val Leu Arg His Ile Gly Asn Leu Asn Glu Phe Ser
                645                 650                 655

Gly Asp Leu Lys Glu Arg Gly Leu Thr Leu Gln Trp Val Tyr Ser Ala
            660                 665                 670

Arg Gly Asp Tyr Ile Arg Ala Ala Glu Lys Leu Arg Lys Glu Ile Tyr
        675                 680                 685

Ser Ser Glu Arg Asn Asp Glu Arg Leu Met Arg Met Tyr Asn Val Arg
    690                 695                 700

Ile Met Arg Val Glu Phe Tyr Phe Leu Ser Gln Tyr Val Ser Pro Ala
705                 710                 715                 720

Asp Ser Pro Phe Arg His Ile Phe Leu Gly Gln Gly Asp His Thr Leu
                725                 730                 735

Gly Ala Leu Val Asp His Leu Arg Met Leu Arg Ala Asp Gly Ser Gly
            740                 745                 750

Ala Ala Ser Ser Arg Leu Thr Ala Gly Leu Gly Phe Gln Glu Ser Arg
            755                 760                 765

Phe Arg Arg Gln Leu Ala Leu Leu Thr Trp Thr Leu Gln Gly Ala Ala
        770                 775                 780

Asn Ala Leu Ser Gly Asp Val Trp Asn Ile Asp Asn Asn Phe
785                 790                 795
```